(12) United States Patent
Slingluff, Jr. et al.

(10) Patent No.: US 11,633,458 B2
(45) Date of Patent: Apr. 25, 2023

(54) COMPOSITIONS AND METHODS FOR TREATING MELANOMA

(71) Applicant: University of Virginia Patent Foundation, Charlottesville, VA (US)

(72) Inventors: Craig L. Slingluff, Jr., Charlottesville, VA (US); Ileana S. Mauldin, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 787 days.

(21) Appl. No.: 15/035,015

(22) PCT Filed: Nov. 7, 2014

(86) PCT No.: PCT/US2014/064578
§ 371 (c)(1),
(2) Date: May 6, 2016

(87) PCT Pub. No.: WO2015/070031
PCT Pub. Date: May 14, 2015

(65) Prior Publication Data
US 2016/0331810 A1    Nov. 17, 2016

Related U.S. Application Data

(60) Provisional application No. 61/901,525, filed on Nov. 8, 2013.

(51) Int. Cl.
| | | |
|---|---|---|
| *A61P 37/04* | (2006.01) | |
| *A61K 38/21* | (2006.01) | |
| *A61K 38/08* | (2019.01) | |
| *A61K 31/353* | (2006.01) | |
| *A61K 45/06* | (2006.01) | |
| *A61K 31/7084* | (2006.01) | |
| *A61K 31/352* | (2006.01) | |
| *A61K 9/00* | (2006.01) | |
| *A61K 38/10* | (2006.01) | |
| *A61K 47/12* | (2006.01) | |

(52) U.S. Cl.
CPC .......... *A61K 38/217* (2013.01); *A61K 9/0014* (2013.01); *A61K 9/0019* (2013.01); *A61K 31/352* (2013.01); *A61K 31/353* (2013.01); *A61K 31/7084* (2013.01); *A61K 38/08* (2013.01); *A61K 38/10* (2013.01); *A61K 45/06* (2013.01); *A61K 47/12* (2013.01)

(58) Field of Classification Search
CPC .............................. A61K 38/217; A61P 37/04
See application file for complete search history.

(56) References Cited

U.S. PATENT DOCUMENTS

| | | | |
|---|---|---|---|
| 4,554,101 A | 11/1985 | Hopp | |
| 5,789,543 A | 8/1998 | Ingham et al. | |
| 6,207,718 B1 | 3/2001 | Papadimitriou | |
| 2007/0203185 A1* | 8/2007 | Muhlradt | A61K 35/15 514/324 |
| 2011/0218239 A1 | 9/2011 | Vogel et al. | |
| 2011/0287089 A1 | 11/2011 | Rittner | |
| 2012/0064035 A1* | 3/2012 | Hadden | A61K 38/164 424/85.2 |
| 2012/0288515 A1 | 11/2012 | Robbins et al. | |

FOREIGN PATENT DOCUMENTS

| | | |
|---|---|---|
| EP | 1484064 A1 | 12/2004 |
| EP | 1641474 | 3/2010 |
| EP | 3065829 B1 | 5/2021 |
| WO | WO 2012096631 | 7/2012 |

OTHER PUBLICATIONS

Kiura, K., et al. The synthetic analogue of mycoplasmal lipoprotein FSL-1 induces dendritic cell maturation through Toll-like receptor 2. FEMS Immunol. Med. Microbiol., 2006, vol. 46, p. 78-84.*
Wang, L-C S., et al Induction of tumour necrosis factor and interferon-gamma in cultured murine splenocytes by the antivascular agent DMXAA and its metabolites. Biochemical Pharmacology, 2004, vol. 67, p. 937-945.*
Mauldin, I.S., et al. TLR2/6 agonists and interferon-gamma induce human melanoma cells to produce CXCL10. Int. J. Cancer, 2015, 137(6):1386-1396.*
Mauldin, I.S., et al. Intratumoral interferon-gamma increases chemokine production but fails to increase T-cell infiltration of human melanoma metastases. Cancer Immunol. Immunother., 2016, 65(10):1189-1199.*
Menaa F. "Latest approved therapies for metastatic melanoma: what comes next?" J Skin Cancer 2013;2013:735282.

(Continued)

*Primary Examiner* — Gyan Chandra
(74) *Attorney, Agent, or Firm* — Jenkins, Wilson, Taylor & Hunt, P.A.

(57) ABSTRACT

Toll-like receptor (TLR) agonists can induce chemokine production. We find that TLR2 and TLR6 are widely expressed on human melanoma cells, and that TLR2/6 agonists (MALP-2 or FSL-1) synergize with interferon-gamma (IFNγ) to induce production of CXCL10 from melanoma cells. Furthermore, melanoma cells and immune cells freshly isolated from surgical specimens also respond to TLR2/6 agonists +IFNγ by upregulating CXCL10 production, compared to treatment with either agent alone. It is also disclosed herein that these compounds are useful in inducing CLXL10 in other types of cancer. Collectively, these data identify a novel synergy of TLR2/6 agonists +IFNγ for inducing CXCL10 production directly from melanoma cells, raising the possibility that intratumoral administration of these agents may improve immune signatures in melanoma and have value in combination with other immune therapies, by supporting T-cell migration into melanoma metastases.

23 Claims, 39 Drawing Sheets

(56) References Cited

OTHER PUBLICATIONS

Dengel LT, Norrod AG, Gregory BL, Clancy-Thompson E, Burdick MD, Strieter RM, Slingluff CL, Jr., Mullins DW. "Interferons induce CXCR3-cognate chemokine production by human metastatic melanoma". J Immunother Nov. 2010;33(9):965-74.

Erdag G, Schaefer JT, Smolkin ME, Deacon DH, Shea SM, Dengel LT, Patterson JW, Slingluff CL, Jr. "Immunotype and immunohistologic characteristics of tumor-infiltrating immune cells are associated with clinical outcome in metastatic melanoma". Cancer Res Mar. 1, 2012;72(5):1070-80.

Hong M, Puaux AL, Huang C, Loumagne L, Tow C, Mackay C, Kato M, Prevost-Blondel A, Avril MF, Nardin A, Abastado JP. "Chemotherapy induces intratumoral expression of chemokines in cutaneous melanoma, favoring T-cell infiltration and tumor control". Cancer Res Nov. 15, 2011;71(22):6997-7009.

Harlin H, Meng Y, Peterson AC, Zha Y, Tretiakova M, Slingluff C, McKee M, Gajewski TF. "Chemokine expression in melanoma metastases associated with CD8+ T-cell recruitment". Cancer Res Apr. 1, 2009;69(7):3077-85.

Tanese K, Grimm EA, Ekmekcioglu S. "The role of melanoma tumor-derived nitric oxide in the tumor inflammatory microenvironment: its impact on the chemokine expression profile, including suppression of CXCL10". Int J Cancer Aug. 15, 2012;131(4):891-901.

Dufour JH, Dziejman M, Liu MT, Leung JH, Lane TE, Luster AD. "IFN-gamma-inducible protein 10 (IP-10; CXCL10)-deficient mice reveal a role for IP-10 in effector T cell generation and trafficking". J Immunol Apr. 1, 2002;168 (7):3195-204.

Schill T, Schon MP, Pletz N, Emmert S, Schon M. "Stimulation of pulmonary immune responses by the TLR2/6 agonist MALP-2 and effect on melanoma metastasis to the lung". Exp Dermatol Feb. 2012;21(2):91-8.

Oldford SA, Haidl ID, Howatt MA, Leiva CA, Johnston B, Marshall JS. "A critical role for mast cells and mast cell-derived IL-6 in TLR2-mediated inhibition of tumor growth". J Immunol Dec. 1, 2010;185(11):7067-76.

Hasan UA, Caux C, Perrot I, Doffin AC, Menetrier-Caux C, Trinchieri G, Tommasino M, Vlach J. "Cell proliferation and survival induced by Toll-like receptors is antagonized by type I IFNs". Proc Natl Acad Sci U S A May 8, 2007;104 (19):8047-52.

Goto Y, Arigami T, Kitago M, Nguyen SL, Narita N, Ferrone S, Morton DL, Irie RF, Hoon DS. "Activation of Toll-like receptors 2, 3, and 4 on human melanoma cells induces inflammatory factors". Mol Cancer Ther Nov. 2008;7 (11):3642-53.

Moyle, PM, et al., "Modern Subunit Vaccines: Development, Components, and Research Opportunities", Jan. 11, 2013; p. 367, col. 1, paragraph 1.

Vacchelli, Erika, et al., "Trial Watch: Toll-like receptor agonists for cancer therapy", Oncoimmunology, vol. 2, No. 8, E25238, Aug. 1, 2013 (Aug. 1, 2013), pp. 1-13. XP002770173, ISSN: 2162-402X, DOI: 10.4161/ONCI.25238, *the whole document*.

Schmidt, J., et al., Intratumoural injection of the toll-like receptor-2/6 agonist 'macrophage-activating lipopeptide-2' in patients with pancreatic carcinoma: a phase I/II trial:, British Journal of Cancer, vol. 97, No. 5, Sep. 3, 2007 (Sep. 3, 2007), pp. 598-604, XP002770174, ISSN: 0007-0920, *the whole document*.

Hubbell, H.R., "Synergistic antiproliferative Effective of Human Interferons in Combination with Mismatched Double-Stranded RNA on Human Tumor Cells", International Journal of Cancer, vol. 37, No. 3, Mar. 15, 1986 (Mar. 15, 1986), pp. 359-365, XP009063428, John Wiley & Sons, Inc., US, ISSN: 0020-7136, DOI: 10.1002/IJC.2910370306, *the whole document*.

Cox, G.W. et al., "Tumor necrosis factor-alpha-dependent production of reactive nitrogen intermediates mediates I FN-gamma plus IL-2-induced murine macrophage tumoricidal activity", Journal of Immunology, vol. 149, 10, Nov. 15, 1992 (Nov. 15, 1992), pp. 3290-3296, XP002770175, ISSN: 0022-1761, *the whole document*.

Weigt, Henning, et al., "Efficacy of macrophage-activating lipopeptide-2 combined with interferon-gamma in a murine asthma model", American Journal of Respiratory and Critical Care Medicine, vol. 172, No. 5, Sep. 1, 2005 (Sep. 1, 2005), pp. 566-572, XP002770176, ISSN: 1073-449X, *the whole document*.

Carreno, Beatriz, M., et al., "IL-12p70-producing patient DC vaccine elicits Tc1-polarized immunity", The Journal of Clinical Investigation, vol. 123, No. 8, Aug. 2013 (Aug. 2013), pp. 3383-3394, XP002770177, ISSN: 1558-8238, *the whole document*.

Proost, Paul, et al., "Microbial Toll-like receptor ligands differentially regulate CXCL10/IP-10 expression in fibroblasts and mononuclear leukocytes in synergy with IFN-gamma and provide a mechanism for enhanced synovial chemokine levels in septic arthritis", European Journal of Immunology, vol. 33, No. 11, Nov. 2003 (Nov. 2003), pp. 3146-3153, XP002770178, ISSN: 0014-2980, *the whole document*.

Antonicelli, F., et al., "CXCL10 reduces melanoma proliferation and invasiveness in vitro and in vivo", British Journal of Dermatology, vol. 164, No. 4, Mar. 16, 2011 (Mar. 16, 2011), pp. 720-728, XP055330629, UK, ISSN: 0007-0963 DOI: 10.1111/j.1365-2133.2010.10176.x, *the whole document*.

Kittlesen, D., et al., J. Immunol. 1998, 160: 2099-2106.

Cox, A., et al., Science, Apr. 29, 1994; 264 (515): 716-9.

Burdette, D., et al., Nature, 478 (7370); 515-518—STING.

Fu, J., et al., Sci. Transl. Med., Apr. 15, 2015: 7 (283), STING.

Kaczanowska, Sabina, et al., "TLR agonists: our best frenemy in cancer immunotherapy", Journal of Leukocyte Biology, vol. 93, Jun. 2013, 847-863.

Ren, Tao, et al., "TLR9 Signaling Promotes Tumor Progression of Human Lung Cancer Cell in Vivo", Pathology Oncol. Res., 2009, 15:623-630 DOI: 10.1007/s12253-009-9163-0.

Iwasaki et al. "Toll-like receptor control of the adaptive immune responses," Nat Immunol. 5(10), pp. 987-995 (2004).

Kang et al. "Structural Biology of the Toll-Like Receptor Family," Annu Rev Biochem, 80:917-941 (2011).

Lopez et al. "To fight or die—inhibitor of apoptosis proteins at the crossroad of innate immunity and death," Curr Opin Cell Biol, 22(6), pp. 872-881 (2010).

Niebuhr et al. "Intracutaneous injection of the macrophage-activating lipopeptide-2 (MALP-2) which accelerates wound healing in mice—a phase I trial in 12 patients," Exp Dermatol, vol. 17(12), pp. 1052-1056 (2008).

Powderly et al. "Biomarkers and associations with the clinical activity of PD-L1 blockade in a MPDL3280A study," 31(15), Abstract #3001 (2013).

Roth et al. "C-C chemokines, but not the C-X-C chemokines interleukin-8 and interferon-gamma inducible protein-10, stimulate transendothelial chemotaxis of T lymphocytes," Eur J Immunol, 25(12), pp. 3482-3488 (1995).

Saint-Jean et al. "TLR expression in human melanoma cells," Eur J Dermatol, 21(6), pp. 899-905 (2011).

Schroder et al. "Signal integration between IFNgamma and TLR signalling pathways in macrophages," Immunobiology, 211(6-8), pp. 511-524 (2006).

Shapira-Frommer et al. "Adoptive Immunotherapy of Advanced Melanoma," Curr Treat Options Oncol, 13(3), pp. 340-353 (2012).

Weiss et al. "Molecular insights on the Peripheral and Intratumoral Effects of Systemic High-Dose rIL-2 (Aldesleukin) Administration for the Treatment of Metastatic Melanoma," Clin Cancer Res, 17(23), pp. 7440-7450 (2011).

Yamaguchi et al. "Interferon-gamma production by human cord blood monocyte-derived dendritic cells," Ann Hematol, 84(7), pp. 423-428 (2005).

Yu et al. "Cultured human melanocytes express functional toll-like receptors 2-4, 7 and 9," J Dermatol Sci, 56(2), pp. 113-120 (2009).

Zhou "Molecular Mechanisms of IFN-gamma to Up-Regulate MHC Class I Antigen Processing and Presentation," Int Rev Immunol, 28(3-4), pp. 239-260 (2009).

Alexandrescu et al. "Immunotherapy for Melanoma: Current Status and Perspectives," Author manuscript, pp. 1-38, Published in final edited form as: J lmmunother.,33(6):pp. 570-590 (2010).

(56) References Cited

OTHER PUBLICATIONS

Altschul et al. "Gapped BLAST and PSI-BLAST: a new generation of protein database search programs," Nucleic Acids Res. 25(17): pp. 3389-3402 (1997).
Barksby et al. "Differential expression of immunoregulatory genes in monocytes in response to Porphyromonas gingivalis and *Escherichia coli* lipopolysaccharide," Clin Exp Immunol, 156(3):479-487 (2009).
Bleul et al. "A Highly Efficacious Lymphocyte Chemoattractant, Stromal Cell-derived Factor 1 (SDF-1)," J Exp Med,184(3):1101-1109 (1996).
Bohnhorst et al. "Toll-like receptors mediate proliferation and survival of multiple myeloma cells," Leukemia, 20(6), pp. 1138-1144 (2006).
Carlsson et al., "Protein Thiolation and Reversible Protein-Protein Conjugation: N-Succinimidyl 3-(2-pyridyldithio)propionate, A New Heterobifunctional Reagent," Biochem. J., 173(3), pp. 723-737 (1978).
Chou & Fasman, "Prediction of β-turns," Biophys. J., vol. 26, pp. 367-384 (1979).
Communication of European Publication Number corresponding to European Application No. 14860949.8 dated Aug. 18, 2016.
Crittenden et al. "Pharmacologically Regulated Production of Targeted Retrovirus from T Cells for Systemic Antitumor Gene Therapy," Cancer Res, 63(12), pp. 3173-3180 (2003).
European Communication corresponding to European Application No. 14860949.8 dated Dec. 16, 2019.
Extended European Search Report corresponding to European Application No. 14860949.8 dated Jun. 6, 2017.
Franciszkiewicz et al. "Role of Chemokines and Chemokine Receptors in Shaping the Effector Phase of the Antitumor Immune Response," Cancer Res.;72(24), pp. 6325-6332 (2012).
Giroux et al. "IFN-gamma-Induced MHC Class II Expression: Transactivation of Class II Transactivator Promoter IV by IFN Regulatory Factor-1 is Regulated by Protein Kinase C-alpha," J Immunol 15;171(8):4187-4194 (2003).
Gough et al. Gene Therapy to Manipulate Effector T Cell Trafficking to Tumors for Immunotherapy, J Immunol., 174(9):5766-5773 (2005).
Hamid et al. "Safety and Tumor Responses with Lambrolizumab (Anti-PD-1) in Melanoma," N Engl J Med, 369:134-144 (2013).
International Search Report corresponding to International Application No. PCT/US2014/064578 dated Feb. 26, 2015.
IPRP with Written Opinion corresponding to International Application No. PCT/US2014/064578 dated May 10, 2016.
Intent to Grant corresponding to European Patent Application No. 14860949.8 dated Sep. 21, 2020.
Kang et al. Imiquimod, a Toll-Like Receptor 7 Agonist, Inhibits Melanogenesis and Proliferation of Human Melanocytes, J Invest Dermatol, 129(1):243-246 (2009).
Karlin and Altschul "Methods for assessing the statistical significance of molecular sequence features by using general scoring schemes," Proc. Natl. Acad. Sci. USA, vol. 87, pp. 2264-2268 (1990).
Karlin and Altschul, "Applications and statistics for multiple high-scoring segments in molecular sequences," Proc. Natl. Acad. Sci. USA, vol. 90, pp. 5873-5877 (1993).
Korman et al. "Checkpoint Blockade in Cancer Immunotherapy," Author manuscript, pp. 1-32, published in final edited form as: Adv Immunol, vol. 90, pp. 297-339 (2006).
Kyte & Doolittle, "A Simple Method for Displaying the Hydropathic Character of a Protein,", J. Mol. Biol., vol. 157, pp. 105-132 (1982).
Le Poole et al. "Interferon-gamma Reduces Melanosomal Antigen Expression and Recognition of Melanoma Cells by Cytotoxic T Cells," Am J Pathol, 160(2), pp. 521-528 (2002).
Lee et al. "Tumor-infiltrating lymphocytes in melanoma," Author manuscript, pp. 1-10, published in final edited form as: Curr Oncol Rep, 14(5), pp. 468-474 (2012).
Li et al. "Toll-like receptor signaling in cell proliferation and survival," Author manuscript, pp. 1-20, Cytokine, vol. 49(1), pp. 1-9 (2010).
Makela et al. "Multiple signaling pathways contribute to synergistic TLR ligand-dependent cytokine gene expression in human monocyte-derived macrophages and dendritic cells," J Leukoc Biol., 85(4), pp. 664-672 (2009).
Nakao et al. "Surface-Expressed TLR6 Participates in the Recognition of Diacylated Lipopeptide and Peptidoglycan in Human Cells," J Immunol, 174(3), pp. 1566-1573 (2005).
Ochoa et al. "Distribution of Toll-like receptor 1 and Toll-like receptor 2 in human lymphoid tissue," Immunology, vol. 108(1), pp. 10-15 (2003).
Peng et al. "PD-1 Blockade Enhances T-Cell Migration to Tumors by Elevating IFN-gamma Inducible Chemokines," Author manuscript, pp. 1-17, published in final edited form as: Cancer Res., 72(20):5209-5218 (2012).
Tannenbaum et al. "The CXC Chemokines IP-10 and Mig Are Necessary for IL-12-Mediated Regression of the Mouse RENCA Tumor," J Immunol, vol. 161(2), pp. 927-932 (1998).
Topalian et al. "Safety, Activity, and Immune Correlates of Anti-PD-1 Antibody in Cancer," N Engl J Med, 366(26), pp. 2443-2454 (2012).
Wolchok et al. "Nivolumab plus Ipilimumab in Advanced Melanoma," N Engl J Med, 369(2), pp. 122-133 (2013).
Wu et al. "Adoptive T-cell Therapy Using Autologous Tumor-infiltrating Lymphocytes for Metastatic Melanoma: Current Status and Future Outlook," Author manuscript, pp. 1-32, published in final edited form as: Cancer J, 18(2), pp. 160-175 (2012).
Decision to Grant corresponding to European Patent Application No. 14860949.8-1118 dated Apr. 22, 2021.
Kohli et al. "Key chemokines direct migration of immune cells in solid tumors," Cancer Gene Ther., 12 pages, Feb. 18, 2021 (doi: 10.1038/s41417-021-00303-x).
Arenberg et al., "Improved survival in tumor-bearing SCID mice treated with interferon-gamma-inducible protein 10 (IP-10/CXCL10)." Cancer Immunol. Immunother., vol. 50, pp. 533-538 (2001).
Aronica et al., "Antitumor/Antiestrogenic Effect of the Chemokine Interferon Inducible Protein 10 (IP-10) Involves Suppression of VEGF Expression in Mammary Tissue." J. Interferon Ctyokine Res., vol. 29(2), pp. 83-91 (2009).
Barash et al., "Heparanase enhances myeloma progression via CXCL10 down regulation." Leukemia, vol. 28(11), pp. 2178-2187 (2014).
Barreira da Silva et al., "Dipeptidylpeptidase 4 inhibition enhances lymphocyte trafficking, improving both naturally occurring tumor immunity and immunotherapy." Nat. Immunol., vol. 16(8), pp. 850-861 (2015).
Chow et al., "Intratumoral activity of the CXCR3 chemokine system is required for the efficacy of anti-PD-1 therapy." Immunity, vol. 50(6), pp. 1498-1512 (2019).
Cluff, "Monophosphoryl Lipid A (MPL) as an Adjuvant for Anti-Cancer Vaccines: Clinical Results." Adv. Exp. Med. Biol., vol. 667, pp. 111-123 (2010).
Davis et al., "Intratumoral Administration of TLR4 Agonist Absorbed into a Cellular Vector Improves Antitumor Responses." Clin. Cancer Res., vol. 17(12), pp. 3984-3992 (2011).
De Lange et al., "Digital PCR-Based T-cell Quantification-Assisted Deconvolution of the Microenvironment Reveals that Activated Macrophages Drive Tumor Inflammation in Uveal Melanoma." Mol. Cancer Res., vol. 16(12), pp. 1902-1911 (2018).
Enderlin et al., "TNF-alpha and the IFN-gamma-inducible protein 10 (IP-10/CXCL-10) delivered by parvoviral vectors act in synergy to induce antitumor effects in mouse glioblastoma." Cancer Gene Ther., vol. 16, pp. 149-160 (2009).
Flores et al., "A Novel Prognostic Model for Osteosarcoma Utilizing Circulating CXCL10 FLT3LG" Cancer, vol. 123(1), pp. 144-154 (2017).
Fujita et al., "Effective Immunotherapy against Murine Gliomas Using Type 1 Polarizing Dendritic Cells—Significant Roles of CSCL10." Cancer Res., vol. 69(4), pp. 1587-1595 (2009).
Ganju et al., "The alpha-Chemokine, Stromal Cell-derived Factor-1alpha, Binds to the Transmembrane G-protein-coupled CXCR-4 Receptor and Activates Multiple Signal Transduction Pathways." J. Biol. Chem., vol. 273(36), pp. 23169-32175 (1998).

(56) References Cited

OTHER PUBLICATIONS

Han et al., "LPS alters the immune-phenotype of glioma and glioma stem-like cells and induces in vivo antitumor immunity via TLR4." J. Exp. Clin. Cancer Res., vol. 36, Article No. 83 (11 pages) (2017).
Heitmann et al., "A COVID-19 peptide vaccine for the induction of SARS-CoV-2 T cell immunity." Nature, vol. 601, pp. 617-638 (2022).
Jiang et al., "CXCL10 expression and prognostic significance in stage II and III colorectal cancer." Mol. Biol. Rep., vol. 37, pp. 3029-3036 (2010).
Karin, "CXCR3 Ligands in Cancer and Autoimmunity, Chemoattraction of Effector T Cells, and Beyond." Front. Immunol., vol. 11, Article No. 976 (9 pages) (2020).
Karin et al., "Chemokines beyond chemo-attraction: CXCL10 and its significant role in cancer and autoimmunity." Cytokine, vol. 109, pp. 24-28 (2018).
Kunz et al., "Strong Expression of the Lymphoattractant C-X-C Chemokine Mig is Associated with Heavy Infiltration of T Cells in Human Malignant Melanoma." J. Pathol., vol. 189, pp. 552-558 (1999).
Lapteva et al., "Attraction and Activation of Dendritic Cells at the Site of Tumor Elicits Potent Antitumor Immunity." Am. Soc. Gene Cell Ther., vol. 17(9), pp. 1626-1636 (2009).
Li et al., "CXCL10 mRNA expression predicts response to neoadjuvant chemoradiotherapy in rectal cancer patients." Tumor Biol., vol. 35, pp. 9683-9691 (2014).
Liu et al., "The emerging role of CXCL10 in cancer (Review)." Oncol. Lett., vol. 2, pp. 583-589 (2011).
Luster et al., "IP-10 a-C-X-C-Chemokine, Elicits a Potent Thymus-dependent Antitumor Response In Vivo." J. Exp. Med., vol. 178, pp. 1057-1065 (1993).
Mauldin et al., "Topical treatment of melanoma metastases with imiquimod, plus administration of a cancer vaccine, promotes immune signatures in the metastases." Cancer Immunol. Immunother., vol. 65(10), pp. 1201-1212 (2016).
Mei et al., "Antitumor efficacy of combination of interferon-gamma-inducible protein 10 gene with gemcitabine, a study in murine model." J. Exp. Clin. Cancer Res., vol. 27, Article No. 63 (13 pages) (2008).
Meissen et al., "A multipeptide vaccine plus toll-like receptor agonists LPS or polyICLC in combination with incomplete Freund's adjuvant in melanoma patients." J. Immother. Cancer, vol. 7, Article No. 163 (13 pages) (2019).
Mikucki et al., "Non-redundant Requirement for CXCR3 Signaling during Tumoricidal T Cell Trafficking across Tumor Vascular Checkpoints." Nat. Commun., vol. 6, Article No. 7458 (30 pages) (2015).
Nagpal et al., "Overexpression of CXCL10 in human prostate LNCaP cells activates its receptor (CXCR3) expression and inhibits cell proliferation." Biochim. Biophys. Acta, vol. 1762, pp. 811-818 (2006).
Okada, "Brain Tumor Immunotherapy with Type-1 Polarizing Strategies." Cancer Vaccines: Ann. NY Acad. Sci., vol. 1174, pp. 18-23 (2009).
Peng et al., "Epigenetic silencing of Th1 type chemokines shapes tumor immunity and immunotherapy." Nature, vol. 527, pp. 249-253 (2015).
Persano et al., "Anti-angiogenic gene therapy of cancer: Current status and future prospects." Mol. Aspects Med., vol. 28, pp. 87-114 (2007).
Rainczuk et al., "Evidence for the antagonistic form of CXC-motif chemokine CXCL10 in serous epithelial ovarian tumors." Int. J. Cancer, vol. 134, pp. 530-541 (2014).
Reschke et al., J. Immunother. Cancer, vol. 9, Article ID e003521 (8 pages) (2021).
Ribas et al., "SD-101 in Combination with Pembrolizumab in Advanced Melanoma: Results of a Phase Ib, Multicenter Study." Cancer Discov., vol. 8(10), pp. 1250-1257 (2018).
Salazar et al., "Therapeutic In Situ Autovaccination against Solid Cancers with Intratumoral Poly-ICLC: Case Report, Hypothesis, and Clinical Trial." Cancer Immunol. Res., vol. 2(8), pp. 720-724 (2014).
Sato et al., "Expression of Interferon-Gamma-Inducible Protein 10 Related to Angiogenesis in Uterine Endometrial Cancers." Oncol., vol. 73, pp. 246-251 (2007).
Sharma et al., "TLR1/2 ligand enhances antitumor efficacy of CTLA-4 blockade by increasing intratumoral Treg depletion." Proc. Natl. Acad. Sci., USA, vol. 116(21), pp. 10453-10462 (2019).
Slingluff et al., "Intratumoral Immune Therapy for Recurrent Breast Cancer with Polyiclc, and Tremelimumab Combined with Systemic Durvulamab" (abstract). J. Immunother. Cancer, vol. 9(Suppl 2), p. A363, Abstract 337 (2021).
Stone et al., "Nanoparticle-Delivered Multimeric Soluble CD40L DNA Combined with Toll-Like Receptor Agonists as a Treatment for Melanoma." PLoS ONE, vol. 4(1), Article ID e7334 (14 pages) (2009).
Wennerberg et al., "CXCL10-induced migration of adoptively transferred human natural killer cells toward solid tumors causes regression of tumor growth in vivo." vol. 64, pp. 225-235 (2015).
Wenzel et al., "Type I Interferon-Associated Recruitment of Cytotoxic Lymphocytes: A Common Mechanism in Regressive Melanocytic Lesions." Am. J. Clin. Pathol., vol. 124, pp. 37-48 (2005).
Wongthida et al., "VSV Oncolytic Virotherapy in the B16 Model Depends Upon Intact MyD88 Signaling." Amer. Soc. Gene Cell Ther., vol. 19(1), pp. 150-158 (2011).
Yang et al., "CXC-chemokine-ligand-10 gene therapy efficiently inhibits the growth of cervical carcinoma on the basis of its anti-angiogenic and antiviral activity." Biotechnol. Appl. Biochem., vol. 53, pp. 209-216 (2009).
Zhang et al., "Expression and clinical significance of chemokine CXCL10 and its receptor CXCR3 in hepatocellular carcinoma" (translation). J. Peking Univ.(Health Sci.), vol. 51(3) (7 pages) (2019).
Zhao et al., "Combining CXCL10 gene therapy and radiotherapy improved therapeutic efficacy in cervical cancer HeLa cell xenograft tumor models." Oncol. Lett., vol. 10, pp. 768-772 (2015).
Zumwalt et al., "Active secretion of CXCL10 and CCL5 from colorectal cancer microenvironments associates with GranzymeB+ CD8+ T-cell infiltration." Oncotarget, vol. 6(5), pp. 2981-2991 (2014).
Slingluff et al., "Randomized Multicenter Trial of the Effects of Melanoma-Associated Helper Peptides and Cyclophosphamide on the Immunogenicity of a Multipeptide Melanoma Vaccine," Journal of Clinical Oncology, vol. 29, No. 21, pp. 2924-2932 (2011).

* cited by examiner

COMPOSITIONS AND METHODS FOR TREATING MELANOMA

CROSS REFERENCE TO RELATED APPLICATIONS

This application is a national stage filing of International Application No. PCT/US2014/64578, filed Nov. 7, 2014, which claims benefit of priority pursuant to 35 U.S.C. § 119(e) to U.S. provisional patent application No. 61/901,525, filed on Nov. 8, 2013. The entire disclosures of the afore-mentioned patent applications are incorporated herein by reference.

STATEMENT REGARDING FEDERALLY SPONSORED RESEARCH OR DEVELOPMENT

This invention was made with government support under Grant No. CA044579, awarded by The National Institutes of Health. The government has certain rights in the invention.

BACKGROUND

Immune therapies have emerged as the most effective therapies for inducing durable regressions and control of melanoma mediating clinical benefit through inducing, expanding, or re-activating antitumor T-cells (1-8). Tumors infiltrated by T-cells are more likely to respond to immune therapies, while those lacking T-cells commonly fail to respond and are associated with shorter overall patient survival (8-15). Metastases with immune cell infiltrates can be differentiated from those without infiltrates, in part, by their expression of immune cell-attracting chemokines, including CXCL10 (11; 15). High CXCL10 expression in the TME is associated with better T-cell infiltration, tumor control, and disease-free survival (14; 16). CXCL0 has also been implicated mechanistically in T-cell infiltration associated with PD-1 blockade (17). Thus, approaches to increase CXCL10 production in melanoma metastases may improve the overall efficacy of immune therapies.

Toll Like Receptor (TLR) agonists induce expression of cytokines and chemokines from various cells. Also, interferons specifically induce CXCL9, CXCL10, and CXCL11 (18). Thus, both TLR agonists and interferons are candidate agents for inducing chemokines in melanoma metastases. Immune cells are commonly considered the dominant source of chemokines, but others and we have reported that cancer cells including melanoma can produce CXCL10 in response to IFNγ (11; 19). However, it is not known whether TLR agonists induce melanoma cells to produce CXCL10 or other T-cell-attracting chemokines (CCL2-5, CXCL9-10, and CXCL12 (15)).

There is a long felt need in the art for compositions and methods useful for treating melanomas and other cancers. The present invention satisfies these needs.

SUMMARY OF THE INVENTION

It is disclosed herein that a novel synergy exists between IFNγ and agonists of some Toll-Like Receptors (TLR) for inducing CXCL10 production directly from melanoma cells and other cancer cells. That is, when used as a combination therapy the resulting induction of CXCL10 is greater than an additive when comparing the use of IFNγ alone or the agonist alone. In one embodiment, the method is useful for treating cancer.

Because CXCL10 promotes the migration of $CD4^+$ and $CD8^+$ T-cells, these findings suggest a possible new therapeutic approach for enhancing CXCL10 production and thus immune cell migration toward melanoma and other cancer cells. In one aspect, the agonists are agonists of TLR2/6, TLR1/2, and TLR4. For example, it is disclosed herein that a combination therapy of a TLR2/6 agonist and IFNγ significantly enhances CXCL10 production from melanoma cells when compared to IFNγ treatment alone. The invention is based in part on a theory tested herein that TLR ligation would induce T-cell-attracting chemokines, including CXCL10, directly from melanoma cells, alone or in combination with IFNγ.

It is disclosed that melanoma cells produce few immune cell-attracting chemokines constitutively. Melanomas express multiple TLRs; however, it is disclosed herein that stimulation with TLR agonists poly-ICLC (TLR3), LPS (TLR4), MALP-2 (TLR2/6), FSL-1 (TLR2/6), imiquimod (TLR7), resiquimod (TLR7/8), or CpG (TLR9) alone induced little chemokine production. In contrast, treatment with TLR2/6 agonists (MALP-2 or FSL-1) +IFNγ synergistically and selectively increased CXCL10 production, compared to either treatment alone. These findings are corroborated on fresh surgical specimens of human melanoma metastases. TLR2 and TLR6 are expressed by most melanoma lines tested. Furthermore, TLR2/6 agonists +IFNγ treatment does not enhance melanoma proliferation or hinder apoptosis. Collectively, these data support investigation of combined therapy with TLR2/6 agonists plus IFNγ as a novel approach to enhance CXCL10 production directly from melanoma cells, which may facilitate T-cell infiltration into melanoma metastases.

Depending on the tumor being treated and the TLRs expressed by the cells of that tumor, one of ordinary skill in the art can determine which agonist to administer and whether to administer it in combination with IFNγ or other agents, including inducers of IFNγ. The present invention further provides compositions, methods, and assays for detecting various TLRs to aid in developing a treatment regimen. The invention further provides treatment regimens once the specific TLRs being expressed have been determined.

The present application discloses compositions and methods for inducing CXCL10 production in cancer cells. The types of cancer include, for example, melanoma, ovarian, breast, lung, and head and neck cancer. In one embodiment, the present application discloses a synergy between TLR agonists and IFNγ for inducing CXCL10 production. In one aspect, the effect is at least additive. In one aspect, the present application discloses a synergy between TLR2/6 agonists and IFNγ for inducing CXCL10 production. In one aspect, the agonists are MALP-2 and FSL-1. It is further disclosed herein that TLR2/6 agonists and IFNγ induce CCL3 production. LPS and IFNγ are also disclosed herein to induce an increase in the number of melanoma cells producing CXCL10. The treatments described herein do not enhance proliferation, nor do they inhibit apoptosis of treated cells.

In one embodiment, the agonist is selected from the group consisting of macrophage-activating lipopeptide 2 (MALP-2), fibroblast-stimulating lipopeptide-1 (FSL-1), lipopolysaccharide (LPS), and Pam3CysSerLys4 (Pam3).

The present invention provides for administration of a pharmaceutical composition of the invention for treatment of a cancer responsive to a TLR agonist or responsive to a TLR agonist used in combination therapy with IFNγ. In one aspect, additional agents can be used in the combination therapy.

It is further disclosed herein that IFNγ and agonists of a TLR can induce CXCL10 in cancers other than melanoma, including ovarian cancer, breast cancer, lung cancer, and head and neck cancer. It is also disclosed herein that, for some cancers, CXCL10 can be induced with one or more agonists of a TLR without the need to add IFNγ. When two or more compounds are to be administered, they can be administered in the same pharmaceutical composition or in separate pharmaceutical compositions. When administered in separate pharmaceutical compositions, they can be administered simultaneously or one can be administered first. The amount of time between administration of the different compounds can vary and can be determined by one of ordinary skill in the art. In one aspect, one or more of the compounds can be administered more than once. In one aspect, a compound is administered at least twice. In another aspect, a compound is administered at least five times. In one aspect, a compound is administered at least once a day, or at least once a week, or at least once a month. Each different compound being administered does not have to be administered the same number of times as every other compound being administered.

In one embodiment, IFNγ and at least one agonist of a TLR are administered. In one aspect, at least two different agonists are administered. In one aspect, the at least two agonists are agonists of different TLRs. In one aspect, the at least two agonists are agonists of the same TLR. In one aspect, a pharmaceutical composition of the invention comprises IFNγ and at least one agonist of a TLR and optionally comprises an inducer of IFNγ. In one aspect, at least one agonist of a TLR and an inducer of IFNγ are administered.

In one embodiment, an inducer of IFNγ is a STING agonist. In one aspect, the STING agonist is a flavonoid or cyclic diadenylate monophosphate (c-di-AMP). In one aspect, the flavonoid is flavone acetic acid (FAA) or 5,6-dimethylxanthenone-4-acetic acid (DMXAA).

In one embodiment, an agonist of the invention is coupled to a molecule or delivery vehicle to aid in localization at a site of administration. In one aspect the molecule or delivery vehicle is selected from the group consisting of a lipid, polyethylene glycol, or a liposome. In one aspect, the lipid is a fatty acid. In one aspect, the fatty acid is 3M-052. In one aspect, an agonist of the invention is coupled to IFNγ. In one aspect, an agonist of the invention is coupled to an inducer of IFNγ. In one aspect, the agonist or IFNγ are coupled to a lipid.

In one embodiment of the invention, the method comprises administration of a pharmaceutical composition of the invention comprising a pharmaceutically acceptable carrier, IFNγ, at least one agonist of the invention, and optionally an inducer of IFNγ, or administration of at least one agonist of the invention and optionally an inducer of IFNγ.

For some cancers, only a TLR agonist will be administered. In another aspect, at least two different TLR agonists are administered.

In one embodiment, administration of a pharmaceutical composition comprising compounds of the invention induces CXCL10 in tumor cells.

The present application further discloses differential upregulation of genes when using IFNγ alone versus either MALP-2 or FSL-1 (TLR agonists) in combination with IFNγ.

In one aspect, useful TLR agonists of the invention include, but are not limited to, MALP-2, FSL-1, Pam3CSK4, flagellin, poly-ICLC, LPS, imidazoquinolines such as imiquimod (R-837) and resiquimod (R-848), Pam2CSK4, ODN2395, and CpG. In one aspect, more than one agonist can be administered.

In one embodiment, the present invention provides for intratumoral, parenteral, intravenous, topical, or direct administration of compounds of the invention. One of ordinary skill in the art can determine the best route or type of administration depending on, for example, the type of cancer, location of the tumor, and the age and health of the subject being treated.

In one embodiment, the present invention provides for intratumoral administration of at least one agonist of the invention. In one aspect, the agonist is an agonist of a TLR. In one aspect, the TLR is TLR1, TLR2, TLR4, or TLR6. In one aspect, the agonist is a TLR2/6 agonist. In another aspect, the agonist is a TLR1/2 agonist. In a further aspect, the agonist is a TLR4 agonist.

One of ordinary skill in the art can determine which route of administration of a compound or combination of compounds to use when treating a subject.

IFNγ can be administered at a dose determined by one of ordinary skill in the art when used in combination with a TLR agonist. The dose can vary depending on the stage of the cancer, the size of the tumor, the health of the subject, route of administration, etc. In one embodiment, at least about 5 million IU of IFNγ are administered intratumorally. In another embodiment, at least 2 million IU of IFNγ are administered intratumorally. In another embodiment, at least 1 million IU of IFNγ are administered intratumorally. In a further embodiment, at least 500,000 IU of IFNγ are administered intratumorally. In a further embodiment, at least 100,000 IU of IFNγ are administered intratumorally. In another embodiment, at least 50,000 IU of IFNγ are administered intratumorally. In a further embodiment, at least 10,000 IU of IFNγ are administered intratumorally. In a further embodiment, at least 10,000 IU of IFNγ are administered. In one aspect, the dosage ranges from about 5,000 to about 5,000,000 IU of IFNγ. In one aspect, the dosage ranges from about 25,000 to about 2,000,000 IU of IFNγ. In one aspect, the dosage ranges from about 50,000 to about 1,000,000 IU of IFNγ. In one aspect, the dosage ranges from about 75,000 to about 500,000 IU of IFNγ. In one aspect, the dosage ranges from about 100,000 to about 250,000 IU of IFNγ. In one aspect, the dosage is 65,000 IU of IFNγ. In one aspect, it is 65,000 IU per 5 cm of tumor diameter.

For all compounds of the invention, the amount or dose used can be, for example, based on the size of the tumor. That dose may vary depending on whether the compounds are administered intratumorally or by another method such as parenterally. In one aspect, as described herein regarding doses used per 5 cm of tumor diameter, doses can be calculated based on the diameter or volume of the tumor to be treated relative to the 5 cm diameter dose described herein. In another aspect, when administered parenterally, the dose can be based on a unit dose or calculated based on the weight of the subject to be treated. One of ordinary skill in the art can also determine whether to adjust the dose based on criteria such as the stage of the cancer, size of the tumor, and age and health of the subject.

In one embodiment, a dosage ranging from about 0.1 μg to about 1,000 μg of TLR agonist is administered. In one embodiment, a dosage ranging from about 1.0 μg to about 500 μg of TLR agonist is administered. In one embodiment, a dosage ranging from about 10 μg to about 100 μg of TLR agonist is administered.

In one embodiment, an effective amount of MALP-2 is administered. In one embodiment a dosage ranging from about 0.1 µg to about 1,000 µg is administered intratumorally. In one embodiment a dosage ranging from about 1.0 µg to about 500 µg is administered intratumorally. In one aspect, a dosage ranging from about 2.0 µg to about 100 µg is administered intratumorally. In one aspect, a dosage ranging from about 3.0 µg to about 50 µg is administered intratumorally. In one aspect, a dosage ranging from about 4.0 µg to about 25 µg is administered intratumorally. In one aspect, a dosage ranging from about 5.0 µg to about 20 µg is administered intratumorally. In one aspect, a dosage ranging from about 6.0 µg to about 10 µg is administered intratumorally. In one aspect, a dose of about 6.5 µg of MALP-2 is administered intratumorally.

In one embodiment, an effective amount of FSL-1 is administered. In one embodiment a dosage ranging from about 0.1 µg to about 1,000 µg is administered intratumorally. In one aspect, a dosage ranging from about 1.0 µg to about 750 µg is administered intratumorally. In one aspect, a dosage ranging from about 10 µg to about 500 µg is administered intratumorally. In one aspect, a dosage ranging from about 50 µg to about 400 µg is administered intratumorally. In one aspect, a dosage ranging from about 100 µg to about 350 µg is administered intratumorally. In one embodiment, a dose of about 325 µg of FSL-1 is administered intratumorally. Similar doses of Pam3CSK4 can be administered.

One of ordinary skill in the art will appreciate that higher doses may be needed when IFNγ or an agonist of a TLR are administered systemically or parenterally compared to what is administered intratumorally. Doses can be administered as a unit dose or can be based on the weight of the subject.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" unless stated otherwise.

In one embodiment, an agonist of the invention can be administered in conjunction with another therapeutic agent. Additional therapeutic agents include, for example, chemotherapeutic agents, steroids, anti-inflammatories, antimicrobials, inducers of chemokines, etc. In one aspect, more than one therapeutic agent can be administered in conjunction with an agonist of the invention. In one aspect, the agonist and an additional therapeutic agent are coupled to one another. One of ordinary skill in the art can appreciate that multiple methods are available for coupling two or more different molecules to one another. In one aspect, the agonist and at least one therapeutic agent are administered at the same time or within a short time period of one another. In one aspect, the additional therapeutic agent is IFNγ. In one aspect, the agonist is administered in conjunction with an agent that induces IFNγ. In one aspect, the agonist is coupled to a lipid. In one aspect, the lipid is a fatty acid. In one aspect, the fatty acid is 3M-052. In one aspect, the agonist is administered with a molecule or agent that helps to keep the agonist localized to the site of injection. In one aspect, the agonist is coupled to a polyethylene glycol. In another aspect, the agonist is coupled to a liposome. In one aspect, the agonist is coupled to two or more different kinds of molecules, including, for example, a lipid and a molecule that induces IFNγ.

The present invention provides compositions and methods for downregulating Melan-A/MART-1 expression in melanoma cells. In one aspect, ligating TLR2/6 down regulates Melan-A/MART-1 expression. In one aspect, the treatment has no effect on MHC, gp100, apoptosis, or proliferation of cancer cells being treated.

The present invention further provides kits comprising compounds of the invention, an applicator, and an instructional material for the use thereof.

Various aspects and embodiments of the invention are described in further detail below.

BRIEF DESCRIPTION OF THE DRAWINGS

FIG. 1A. Relative expression levels of TLR transcripts represented as normalized hybridization intensity data. FIG. 1B. Relative fold changes in gene expression for the indicated chemokines, TLR stimulated cells were compared to unstimulated cells (mean±SD, pooled data from melanoma cell lines VMM1, DM13, DM93 and DM122). Data in FIG. 1A-1B are from a single array. FIG. 1C. Representative expression of TLRs expressed by melanoma cell lines and PBMC (leukopak); graphed data are the MFI of TLR expression assessed by flow cytometric analysis. FIG. 1D (comprising six graphs). Melanoma cells were analyzed by flow cytometry for chemokine production after overnight stimulation with the indicated TLR agonists. Graph of the percentage of melanoma cells expressing chemokines CCL2-5, CXCL9 or CXCL12 after stimulation with the indicated TLR agonists or media alone (untreated melanoma cells). Data shown are pooled from 4 melanoma cell lines VMM1, DM13, DM93 and DM122 and represent the mean±SD for the percent of melanoma cells that expressed the indicated chemokine. Data in FIG. 1D are from 3 or more independent experiments for each cell line.

FIG. 2A. Graphs (4) of the percentage of cells expressing CXCL10 after stimulation. FIG. 2B. Graphs (2) of the percentage of melanoma cells (mean of the 4 melanoma cell lines ±SD) expressing CXCL10 after stimulation with TLR agonists alone (left) or TLR agonists +IFNγ (right). FIG. 2C. Representative histogram overlays (4) demonstrating the MFI for CXCL10 after TLR stimulation. Data are from 3 independent experiments.

FIG. 3A-FIG. 3B (12 panels/images each). Representative image of immunohistochemistry staining for CXCL10 (FIG. 3A) and CXCL9 (FIG. 3B) in stimulated melanoma cell lines DM13 (top) and VMM1 (bottom) with, left to right, No treatment, MALP-2, FSL-1, IFNγ, MALP-2+IFNγ, and FSL-1+IFNγ. Scale bars represent 100 µm. FIG. 3C. Graphic illustration of ELISA assays to detect CXCL10 from supernatants of stimulated melanoma cells DM13 (left) and VMM1 (right). FIG. 3D. TLR agonist dose response assay. Graph shows the percent of CXCL10 producing DM13 cells after stimulation, as assessed by flow cytometry. Data are from 2 independent experiments.

FIG. 4A. Graph of the percentage of melanoma apoptosis (mean of data from VMM1, DM13, DM93 and DM122 cells ±SD) after stimulation, as assessed by Caspase3/7 and viability staining, and flow cytometry. FIG. 4B. Graphs (two) of the percentage of divided melanoma cells (mean±SD, pooled data from melanoma cell lines VMM1, DM13, DM93 and DM122) assessed by CFSE assay 24 hours (left-open/white bars) and 48 hours (right) post treatment.

FIGS. 5A-5D, 22 panels each. TLR2 and TLR6 are broadly expressed on melanoma. TLR2 and TLR6 expression was assessed on 21 melanoma cell lines by flow cytometry. FIG. 5A-FIG. 5B. The percent of melanoma cells expressing TLR2 (FIG. 5A) or TLR6 (FIG. 5B) are shown for each melanoma cell line. FIG. 5C-FIG. 5D. The MFI for TLR2 (FIG. 5C) and TLR6 (FIG. 5D) for melanoma cell lines, Ramos cells and PBMC (leukopak). Data are representative of 2 experiments.

FIG. 6A. The percent of melanoma cells that are CXCL10$^+$ from patient 1 (top), patient 2 (middle) and patient 3 (bottom) tumors after stimulation with the indicated conditions (left panel). MFI for CXCL10 expression of melanoma cells from patient 1 melanoma (top) and patient 2 melanoma (middle) patient 3 melanoma (bottom) (right panel). FIG. 6B-FIG. 6D. Graph of the percent of CXCL10$^+$ cells from the indicated subsets, patient 1 (FIG. 6B), patient 2 (FIG. 6C), and patient 3 (FIG. 6D) tumor's respectively. FIG. 6E. Graph of CXCL10 measured by ELISA assay, cells are from patient 1 tumor.

FIG. 7A-FIG. 7B. Principal Component Analysis of melanoma cell lines and control cell lines after treatment with TLR agonists, identified by cell lines (FIG. 7A) and TLR stimulation (FIG. 7B). Hierarchical clustering of the chemokine transcript data from GeneChip Analysis to examine associations between TLR stimulation and chemokine expression. FIG. 7C. Non-supervised hierarchical clustering analysis was done on a subset of transcripts that encode chemokines. Gene array data are from one experiment. FIG. 7D-FIG. 7E (each with upper, middle, and lower graphs). Melanoma cell lines derived from patient samples were analyzed for chemokine production induced after overnight stimulation with the indicated TLR agonists +IFNγ (+indicates stimulation with IFNγ). The bars represent the mean percentage of chemokine-producing cells±SD among four melanoma cell lines VMM1, DM13, DM93 and DM122 for CCL2$^+$, CCL3$^+$, CCL4$^+$ (FIG. 7D) and CCL5$^+$, CXCL9$^+$, CXCL12$^+$(FIG. 7E). Chemokine expression data are representative of 3 independent experiments for each cell line.

FIG. 10A (left and right panels of 6 each). Representative image of the expression of MHC Class I (left) and Class II (right) molecules on DM13 cells after treatment. FIG. 10B. Representative image of immunohistochemistry staining for Melan-A/MART-1 (left three images) and gp100 (right three images) in stimulated melanoma cell lines DM13 (top) and VMM1 (bottom). Scale bars represent 100 μm. Data here are representative of at least 2 experiments.

FIG. 11A-Stain 1 (six panels); FIG. 11B-Stain 2 (six panels); FIG. 11C-Stain 3 (six panels).

DETAILED DESCRIPTION

Figure 1A:
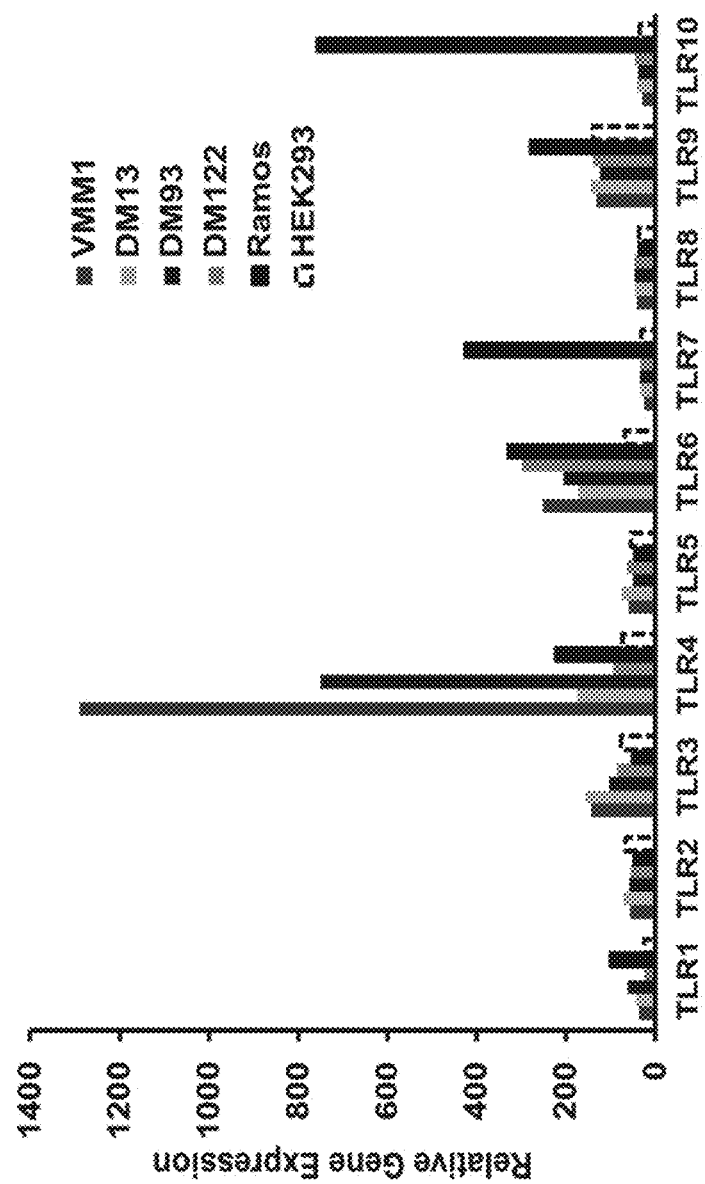
FIGS. 1A-1D. Melanoma cells express several TLRs, but TLR stimulation does not impact CCL2, CCL4, CCL5, CXCL9 and CXCL12 chemokine production from melanoma.

Abbreviations and Acronyms
DC—dendritic cell
FSL-1—fibroblast-stimulating lipopeptide-1
IFNγ—interferon gamma
IPA—Ingenuity Pathway Analysis
IU—international unit
MALP-2—macrophage-activating lipopeptide 2
Pam3—Pam3CysSerLys4, also referred to as Pam3CSK4
PBMC—peripheral blood mononuclear cells/leukocytes
rh—recombinant human
TLR—Toll-like receptor
TME—tumor microenvironment Definitions In describing and claiming the invention, the following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. Therefore, about 50% means in the range of 45%-55%.

A disease or disorder is "alleviated" if the severity of a symptom of the disease, condition, or disorder, or the frequency with which such a symptom is experienced by a subject, or both, are reduced.

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the invention or a prodrug of a compound of the invention to a subject in need of treatment.

As used herein, the term "aerosol" refers to suspension in the air. In particular, aerosol refers to the particlization or atomization of a formulation of the invention and its suspension in the air.

As used herein, an "agonist" is a composition of matter which, when administered to a mammal such as a human, enhances or extends a biological activity attributable to the level or presence of a target compound or molecule of interest in the mammal.

An "agonist of TLR" is one which induces expression, levels, or activity of a TLR as described herein.

An "antagonist" is a composition of matter which when administered to a mammal such as a human, inhibits a biological activity attributable to the level or presence of a compound or molecule of interest in the mammal.

As used herein, an "analog" of a chemical compound is a compound that, by way of example, resembles another in structure but is not necessarily an isomer (e.g., 5-fluorouracil is an analog of thymine).

As used herein, "amino acids" are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

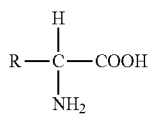

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

Synthetic or non-naturally occurring amino acids refer to amino acids which do not naturally occur in vivo but which, nevertheless, can be incorporated into the peptide structures described herein. The resulting "synthetic peptide" contain amino acids other than the 20 naturally occurring, genetically encoded amino acids at one, two, or more positions of the peptides. For instance, naphthylalanine can be substituted for tryptophan to facilitate synthesis. Other synthetic amino acids that can be substituted into peptides include L-hydroxypropyl, L-3,4-dihydroxyphenylalanyl, alpha-amino acids such as L-alpha-hydroxylysyl and D-alpha-methylalanyl, L-alpha.-methylalanyl, beta.-amino acids, and isoquinolyl. D amino acids and non-naturally occurring synthetic amino acids can also be incorporated into the peptides. Other derivatives include replacement of the naturally occurring side chains of the 20 genetically encoded amino acids (or any L or D amino acid) with other side chains.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys;
IV. Large, aliphatic, nonpolar residues:
Met Leu, Ile, Val, Cys
V. Large, aromatic residues:
Phe, Tyr, Trp The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

The term "aqueous solution" as used herein can include other ingredients commonly used, such as sodium bicarbonate described herein, and further includes any acid or base solution used to adjust the pH of the aqueous solution while solubilizing a peptide.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the peptides encompasses natural or synthetic portions of a longer peptide or protein that are capable of specific binding to their natural ligand or of performing the desired function of the protein, for example, a fragment of a protein of larger peptide which still contains the epitope of interest and is immunogenic.

The term "biological sample," as used herein, refers to samples obtained from a subject, including, but not limited to, skin, hair, tissue, blood, plasma, cells, sweat and urine.

The term "cancer", as used herein, is defined as proliferation of cells whose unique trait-loss of normal controls-results in unregulated growth, lack of differentiation, local tissue invasion, and metastasis. Examples include but are not limited to, melanoma, breast cancer, prostate cancer, ovarian cancer, uterine cancer, cervical cancer, skin cancer, pancreatic cancer, colorectal cancer, renal cancer and lung cancer.

As used herein, the term "carrier molecule" refers to any molecule that is chemically conjugated to the antigen of interest that enables an immune response resulting in antibodies specific to the native antigen.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "compound," as used herein, refers to a polypeptide, an isolated nucleic acid, or other agent used in the method of the invention.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell is a cell being examined.

A "pathoindicative" cell is a cell which, when present in a tissue, is an indication that the animal in which the tissue is located (or from which the tissue was obtained) is afflicted with a disease or disorder.

A "pathogenic" cell is a cell which, when present in a tissue, causes or contributes to a disease or disorder in the animal in which the tissue is located (or from which the tissue was obtained).

A tissue "normally comprises" a cell if one or more of the cell are present in the tissue in an animal not afflicted with a disease or disorder.

As used herein, a "derivative" of a compound refers to a chemical compound that may be produced from another compound of similar structure in one or more steps, as in replacement of H by an alkyl, acyl, or amino group.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

A "fragment" or "segment" is a portion of an amino acid sequence, comprising at least one amino acid, or a portion of a nucleic acid sequence comprising at least one nucleotide.

The terms "fragment" and "segment" are used interchangeably herein.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90%, homology. By way of example, the DNA sequences 3'ATTGCC5' and 3'TATGGC share 50%, homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

By the term "immunizing a subject against an antigen" is meant administering to the subject a composition, a protein complex, a DNA encoding a protein complex, an antibody or a DNA encoding an antibody, which elicits an immune response in the subject, and, for example, provides protection to the subject against a disease caused by the antigen or which prevents the function of the antigen.

The term "immunologically active fragments thereof" will generally be understood in the art to refer to a fragment of a polypeptide antigen comprising at least an epitope, which means that the fragment at least comprises 4 contiguous amino acids from the sequence of the polypeptide antigen.

As used herein the term "induction of CXCL10" refers to the induction or stimulation of synthesis, expression, or increase in levels of CXCL10.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein when referring to a function, refers to the ability of a compound of the invention to reduce or impede a described function. Preferably, inhibition is by at least 10%, more preferably by at least 25%, even more preferably by at least 50%, and most preferably, the function is inhibited by at least 75%. When the term "inhibit" is used more generally, such as "inhibit Factor I", it refers to inhibiting expression, levels, and activity of Factor I.

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

As used herein "injecting, or applying, or administering" includes administration of a compound of the invention by any number of routes and means including, but not limited to, topical, oral, buccal, intravenous, intramuscular, intra arterial, intramedullary, intrathecal, intraventricular, transdermal, subcutaneous, intraperitoneal, intranasal, enteral, topical, sublingual, vaginal, ophthalmic, pulmonary, or rectal means.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

The "level is at least an additive effect", as used herein regarding the induction of CXCL10, means that when at least two different agents are administered, such as IFNγ and MALP-2, the results level of induction is a at least additive when compared to administering IFNγ alone or MALP-2 alone. A "synergistic" effect means that the result is greater than an additive effect.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

A "recombinant polypeptide" is one which is produced upon expression of a recombinant polynucleotide.

A "sample," as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this invention.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present invention.

The term "substantially pure" describes a compound, e.g., a protein or polypeptide which has been separated from components which naturally accompany it. Typically, a compound is substantially pure when at least 10%, more preferably at least 20%0, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

By the term "vaccine," as used herein, is meant a composition which when inoculated into a subject has the effect of stimulating an immune response in the subject, which serves to fully or partially protect the subject against a condition, disease or its symptoms. In one aspect, the condition is cancer. The term vaccine encompasses prophylactic as well as therapeutic vaccines. A combination vaccine is one which combines two or more vaccines, or two or more compounds or agents.

Embodiments

In one embodiment, the invention provides a composition useful as a therapeutic for treating cancer in a subject in need thereof. In one aspect, the cancer is selected from the group consisting of melanoma, ovarian cancer, breast cancer, head and neck cancer, lung cancer, MMMT, bladder cancer, uterine cancer, endometrial cancer, liver cancer, pancreatic cancer, esophageal cancer, stomach cancer, cervical cancer, prostate cancer, adrenal cancer, lymphoma, leukemia, salivary gland cancer, bone cancer, brain cancer, cerebellar cancer, colon cancer, rectal cancer, colorectal cancer, oronasopharyngeal cancer, NPC, kidney cancer, skin cancer, basal cell carcinoma, hard palate carcinoma, squamous cell carcinoma of the tongue, meningioma, pleomorphic adenoma, astrocytoma, chondrosarcoma, cortical adenoma, hepatocellular carcinoma, pancreatic cancer, squamous cell carcinoma, and adenocarcinoma. In one aspect, the cancer is melanoma.

In one embodiment, the treatment encompasses a combination therapy.

The methods and compositions of the invention encompass multiple regimens and dosages for administering the compounds of the invention for use in preventing and treating cancer and for inducing CXCL10 in a cancer cell. For example, a subject can be administered one or more compounds of the invention once or more than once. The frequency and number of doses can vary based on many parameters, including the age, sex, and health of the subject. In one embodiment, up to 50 doses are administered. In another embodiment, up to 40 doses are administered, and in another up to 30 doses are administered. In yet another embodiment, up to 20 doses are administered, and in another up to 10 doses are administered. In one embodiment, 5-10 doses are administered. In one aspect, 5, 6, 7, 8, 9, or 10 doses can be administered.

In one embodiment, the compounds are administered daily, in another weekly, and in another, monthly. Treatment periods may be for a few days, or about a week, or about several weeks, or for several months. Follow-up administration or boosters can be used as well and the timing of that can be varied.

The amount of compound administered per dose can vary as well. For example, in one embodiment the compositions and methods of the invention include a range of compound amounts between about 10 micrograms of each or protein per dose to about 10,000 micrograms of protein per dose. In one aspect, the number of micrograms is the same for each compound. In another aspect, the number of micrograms is not the same for each compound. In another embodiment, the range of amounts of each compound administered per dose is from about 20 micrograms to about 1,000 micrograms. In another aspect, it is from about 50 micrograms to about 500 micrograms. In yet another aspect, it is from about 75 micrograms to about 400 micrograms. In a further aspect, it is from about 100 micrograms to about 300 micrograms, and in another aspect from about 150 micrograms to about 250 micrograms. In one embodiment, about 300 micrograms of each compound is used per dose per treatment.

Subjects can be monitored before and after administration.

Some useful compounds include TLR-agonists:
FSL-1
MALP-2
imiquimod
monophosphoryl lipid A (MPL)
fibroblast-stimulating lipopeptide-1 (FSL-1)
Pam3CSK4 (also referred to as Pam3 and Pam3Cys)
lipolysaccharide (also known as LPS or endotoxin)
peptidoglycan (cell walls)
lipoproteins (bacterial capsules)
hypomethylated DNA (such as CpG found in bacteria and other parasites)
double-stranded DNA as found in viruses
flagellin (bacterial flagella)
PolyI:C
ST-FLA
Gardiquimod
CpG-oligodeoxynucleotide
HKLM
ssRNA40
Pam2CSK4
ODN2395

In various embodiments, at least one TLR ligand or agonist may be selected from the group consisting of a TLR1 ligand, TLR2 ligand, TLR1/2, TLR4 ligand, TLR6, TLR2/6, TLR9 ligand and combinations thereof. In certain embodiments, the at least one TLR ligand may be selected from the group consisting of Pam3cys, PolyI:C, lipopolysaccharide ("LPS"), ST-FLA, Gardiquimod, CpG-oligodeoxynucleotide, TLR1/2 Agonist: Pam3CSK4, TLR2 Agonist: HKLM, TLR3 Agonist: Poly(I:C), TLR4 Agonist: LPS *E. coli*, TLR5 Agonist: Flagellin *S. typhimurium*, TLR6/2 Agonist: FSL-1, TLR7 Agonist: Imiquimod, TLR8 Agonist: ssRNA40, TLR9 Agonist: ODN and combinations thereof. In a particular embodiment, the at least one TLR ligand is a combination of Pam3cys, LPS and CpG ODN.

The present invention encompasses the use of synthetic TLR2/6 lipopeptide agonist $Pam_2CSK_4$ and class C oligodeoxynucleotide TLR9 agonist ODN2395.

In one embodiment, at least one agonist of a TLR is administered as part of a therapy without using IFNγ.

Pattern-recognition receptors (PRRs) recognize and respond to specific microbial components called pathogen-associated molecular patterns (PAMPs) or endogenous molecules produced by injured or dying cells termed danger-associated molecular patterns (DAMPs). Upon recognition of PAMPs or DAMPs, an immune reaction is elicited in order to protect the host from infection. Activation of PRRs has also been implicated in the pathobiology of asthma. Infections of the respiratory tract by bacteria or viruses may act via these receptors to either prevent or exacerbate the clinical presentation of the disease.

The PRR family includes the Toll-like receptors (TLRs), nucleotide-binding oligomerization domain (NOD)-like receptors (NLRs), retinoic acid-inducible gene (RIG)-I-like receptors (RLRs). The most well-known members are the TLRs, a family made up by 10 proteins (TLR1-TLR10) in humans. TLR2 acts as a heterodimer in concert with TLR1 or TLR6, and mediates responses to lipoproteins, lipoteichoic acids, peptidoglycan and zymosan. There are indications that TLR10 also has the ability to form heterodimers with TLR1 and TLR2, but the specific ligand has not yet been identified. TLR3 is involved in the recognition of dsRNA from viruses and the synthetic dsRNA analogue poly(I:C). TLR4 is the main lipopolysaccharide (LPS) receptor, TLR5 recognizes bacterial flagellin, while TLR7 and TLR8 mediate responses to viral ssRNA and imidazoquinolines such as imiquimod (R-837) and resiquimod (R-848). TLR9 responds to bacterial and viral DNA containing unmethylated CpG motifs.

The specificity of TLR2 is fairly broad; some of this breadth derives from its association with either TLR1 or TLR6. Heterodimer TLR2/6 binds bis-acylated lipopeptides such as MALP-2, whereas the TLR1/2 heterodimer binds tris-acylated lipopeptides such as Pam3.

The invention further encompasses the use of IFNγ in a combination therapy with a TLR agonist as well as the use of inducers of IFNγ. In one aspect, the inducer of IFNγ is a STING agonist. In one aspect, the STING agonist is a flavonoid or cyclic diadenylate monophosphate (c-di-AMP). In one aspect, the flavonoid is flavone acetic acid (FAA) or 5,6-dimethylxanthenone-4-acetic acid (DMXAA).

In one embodiment, the agonist of a TLR is coupled to a molecule or delivery vehicle to aid in localization at a site of administration. In one aspect, the molecule or delivery vehicle is a lipid, polyethylene glycol, or a liposome. In one aspect, the lipid is a fatty acid. In one aspect, the fatty acid is 3M-052.

In one embodiment, the agonist of a TLR is coupled to IFNγ. In another embodiment, the agonist coupled to IFNγ is further coupled to a lipid. In one aspect, the agonist is coupled to an inducer of IFNγ.

The present invention encompasses administering the compounds of the invention based on the particular cancer being treated, its location in the subject, etc. In one aspect, a composition is administered by a route selected from the group consisting of intratumoral, parenteral, intravenous, topical, and direct.

Liposomes have certain advantages over the solid core particles previously used, such as the ability to deliver imaging agents or biologically active drugs in their aqueous core or lipid bilayer. Liposomes provide a flexible platform for delivering both hydrophobic and hydrophilic cargo. Liposomes may be useful for both diagnostic imaging and delivery of therapeutic agents to the tumor microenvironment. In one aspect, the compositions and methods of the invention are useful for detecting, identifying, diagnosing, and treating cancer.

In one aspect, a liposome of the invention is about 200 nm in diameter. In one aspect, a liposome of the invention has a diameter ranging from about 100 nm to about 300 nm. In one aspect, a liposome of the invention is about 150 nm in diameter. In one aspect, a liposome of the invention is about 250 nm in diameter.

In one aspect, a liposome of the invention comprises DOTA and optionally at least one other agent or drug. In one embodiment, a liposome of the invention is prepared according to the following method with the following components: 18.8 mg/mL of L-α-Phosphatidylcholine, 4.2 mg/mL of cholesterol, and optionally 0.025 mg/mL of the lipophilic fluorescent probe 3,3'-Dioctadecyloxacarbocyanine Perchlorate. A fluorescent probe is added if there will be fluorescent imaging used later. The liposomes are made using dehydration-rehydration: the lipids and DiO are dissolved in chloroform, the solvent is evaporated, and the resultant thin-film hydrated with a 10 mM solution of chelating agent 1,4,7,10-tetra-azacyclododecane-1,4,7,10-tetraacetic acid (DOTA) in 10 mM 4-(2-Hydroxyethyl)-1-Piperazine-Ethanesulfonic Acid (HEPES) buffer with 150 mM NaCl and a pH of 4 for 2 hours at 37° C. and overnight at 4° C. The liposome solution is freeze-thawed 5 times and then extruded consecutively 20 times through 1 μm, 600 nm, 400 nm and 200 nm polycarbonate membrane filters using a Lipex extruder with high-pressure nitrogen. The non-encapsulated DOTA is removed by dialysis using a Slide-A-Lyzer G2 dialysis cassette with a molecular weight cut-off of 10,000 against five-2 liters of HEPES buffer containing 150 mM NaCl (pH 7.4).

In one aspect, a liposome of the invention can be labeled for imaging. In one aspect, the label is a radiolabel. In one aspect, remote loading is used to radiolabel DOTA-containing liposomes with a useful PET probe, such as $^{64}Cu$ ($t_{1/2}$=12.7 h), by utilizing the lipophilic transporter hydroxyquinoline to ferry $^{64}Cu$ to the liposome interior where it is more tightly chelated by the encapsulated DOTA. Copper loading of the liposomes is confirmed using size exclusion chromatography (SEC) column to determine if the fluorescent dye DiO labeled liposomes eluted in the same fractions as the radioactive $^{64}Cu$. One of ordinary skill in the art will appreciate that the method can be modified as long the result is the same. In one aspect, the radioactive isotope is selected from the group consisting of $^{11}C$, $^{13}N$, $^{15}O$, $^{18}F$, $^{64}Cu$, $^{62}Cu$, $^{124}I$, $^{76}Br$, $^{82}Rb$ and $^{68}Ga$. In one aspect, the chelating agent is selected from the group consisting of DTPA, DO3A, DOTA, EDTA, TETA, EHPG, HBED, NOTA, DOTMA, TETMA, PDTA, TTHA, LICAM, HYNIC, and MECAM.

In one aspect, a liposome of the invention can be labeled with more than one type of imaging agent to allow the liposome, or cells targeted by the liposome, to be imaged or tracked using more than one detection method. For example, both a radiolabel and a fluorescent label can be used at the same time.

The liposomes can be administered to a subject using various techniques. The amount of liposome administered can vary and can depend on the age, sex, and health of the subject, as well as the type of cancer to be imaged. For example, liposomes can be administered at doses from about 0.1 to about 100 µmol total phospholipid. One of ordinary skill in the art can determine a dose to be used. The amount of label can very depending on the label used and the imaging technique used. For example, when using $^{64}$Cu, the present application discloses that the liposome dose was 1.9 µmol total phospholipid labeled with 50-75 µCi (1.85-2.8 MBq) of $^{64}$Cu in a total volume of 160 µL. In one aspect, 100 to 10,000 µCi is used. In another aspect, 500 to 1,000 µCi is used. In one aspect, 400-500 µCi is used.

Useful detectable labels, depending on the technique or combination of imaging techniques used, include, but are not limited to, a radionuclide, a radiological contrast agent, a paramagnetic ion, a metal, a biological tag, a fluorescent label, a chemiluminescent label, an ultrasound contrast agent, and a photoactive agent.

Useful radionuclides of the invention include, but are not limited to, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, 15O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters.

An additional therapeutic agent can include, for example, at least one of a chemotherapeutic agent, an antimicrobial, an anesthetic, an anti-inflammatory, etc.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters. Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide. Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N- and C-termini from "undesirable degradation," a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for homologs of proteins and peptides. Homologs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on protein function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Homologs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein or peptide obtained as described herein may be purified by following known procedures for protein purification, wherein an immunological, enzymatic, or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

In one embodiment typical dosage regimens comprise administering a dosage of 1-1000 μg/kg, more preferably 10-500 μg/kg, still more preferably 10-150 μg/kg, once, twice or three times a week for a period of one, two, three, four or five weeks. According to one embodiment, 10-100 μg/kg is administered once a week for a period of one or two weeks.

The present method, in one aspect, comprises administration of the compounds and compositions comprising them via the injection, transdermal, or oral route. In another, embodiment of the invention, the present method comprises intratumoral administration of the present compounds and compositions comprising them.

Another aspect of the invention relates to a pharmaceutical preparation comprising as the active ingredient the present source of a compound as defined herein before. More particular pharmaceutical preparation comprises as the active ingredient one or more of the aforementioned compounds and biologically active analogs thereof.

The present invention further provides a pharmaceutical preparation comprising one or more of the compounds of the invention. The concentration of said compounds in the pharmaceutical composition can vary widely, i.e., from less than about 0.1% by weight, usually being at least about 1% by weight to as much as 20% by weight or more.

The composition may comprise a pharmaceutically acceptable carrier in addition to the active ingredient. The pharmaceutical carrier can be any compatible, non-toxic substance suitable to deliver the compounds to the subject or to a specific site in the subject. For some compounds, sterile water, alcohol, fats, waxes, and inert solids may be used as the carrier. Pharmaceutically acceptable adjuvants, buffering agents, dispersing agents, and the like, may also be incorporated into the pharmaceutical compositions.

In one embodiment, a composition for intravenous infusion could be made up to contain 10 to 50 ml of sterile 0.9% NaCl or 5% glucose optionally supplemented with a 20% albumin solution and between 10 g and 50 mg, preferably between 50 μg and 10 mg, of the polypeptide. A typical pharmaceutical composition for intramuscular injection would be made up to contain, for example, 1-10 ml of sterile buffered water and between 10 μg and 50 mg, preferably between 50 ug and 10 mg, of the polypeptide of the present invention. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

Amino Acid Substitutions

In certain embodiments, the disclosed methods and compositions may involve preparing peptides with one or more substituted amino acid residues. In various embodiments, the structural, physical and/or therapeutic characteristics of peptide sequences may be optimized by replacing one or more amino acid residues.

In one embodiment, the invention encompasses the substitution of a serine or an alanine residue for a cysteine residue in a peptide of the invention. Support for this includes what is known in the art. For example, see the following citation for justification of such a serine or alanine substitution: Kittlesen et al., 1998 Human melanoma patients recognize an HLA-A-restricted CTL epitope from tyrosinase containing two cysteine residues: implications for tumor vaccine development J Immunol., 60, 2099-2106.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art. For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gin, asn, lys; Asn (N) his, asp, lys, arg, gin; Asp (D) asn, glu; Cys (C) ala, ser; Gin (Q) glu, asn; Glu (E) gin, asp; Gly (G) ala; His (H) asn, gin, lys, arg; Ile (I) val, met, ala, phe, leu; Leu (L) val, met, ala, phe, ile; Lys (K) gin, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gin; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

The invention is also directed to methods of administering the compounds of the invention to a subject.

Pharmaceutical compositions comprising the present compounds are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

The present invention is also directed to pharmaceutical compositions comprising the peptides of the present invention. More particularly, such compounds can be formulated as pharmaceutical compositions using standard pharmaceutically acceptable carriers, fillers, solublizing agents and stabilizers known to those skilled in the art.

The invention also encompasses the use pharmaceutical compositions of an appropriate compound, homolog, fragment, analog, or derivative thereof to practice the methods of the invention, the composition comprising at least one appropriate compound, homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day. Pharmaceutical compositions that are useful in the methods of the invention may be administered systemically in oral solid formulations, ophthalmic, suppository, aerosol, topical or other similar formulations. In addition to the appropriate compound, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound according to the methods of the invention.

Compounds which are identified using any of the methods described herein may be formulated and administered to a subject for treatment of the diseases disclosed herein.

The invention encompasses the preparation and use of pharmaceutical compositions comprising a compound useful for treatment of the conditions, disorders, and diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation.

Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for intratumoral, oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology. A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose.

Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively).

Known emulsifying agents include, but are not limited to, lecithin and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil in water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may also be prepared, packaged, or sold in a formulation suitable for intratumoral administration, direct/topical administration, or parenteral administration The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3 butane diol, for example.

Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self propelling solvent/powder dispensing container such as a device comprising the active ingredient dissolved or suspended in a low-boiling propellant in a sealed container.

Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein. A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference. Typically, dosages of the compound of the invention which may be administered to an animal, preferably a human, range in amount from 1 µg to about 100 g per kilogram of body weight of the subject. While the precise dosage administered will vary depending upon any number of factors, including but not limited to, the type of animal and type of disease state being treated, the age of the animal and the route of administration. In one embodiment, the dosage of the compound will vary from about 10 µg to about 10 g per kilogram of body weight of the animal. In another embodiment, the dosage will vary from about 10 mg to about 1 g per kilogram of body weight of the subject.

The compound may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the subject, etc.

The invention also includes a kit comprising a compound of the invention and an instructional material which describes administering the composition to a cell or a tissue of a subject. In another embodiment, this kit comprises a (preferably sterile) solvent suitable for dissolving or suspending the composition of the invention prior to administering the compound to the subject. The invention also provides an applicator, and an instructional material for the use thereof.

Without further description, it is believed that one of ordinary skill in the art can, using the preceding description and the following illustrative examples, make and utilize the compounds of the present invention and practice the claimed methods. The following examples therefore, specifically point out the preferred embodiments of the present invention, and are not to be construed as limiting in any way the remainder of the disclosure.

EXAMPLES

Cell Lines and Culture.

Melanoma cells lines were obtained from Duke University (DM6, DM13, DM93, DM122) or established from patients at the University of Virginia (VMM1, VMM5A, VMM12, VMM14, VMM15, VMM17, VMM18, VMM39, VMM86, VMM150, VMM273, VMM389) with IRB approval (protocols 5202, 6346, and 10598). Melanoma lines A375, Malme3M, SLM2, SKMEL2, and SKMEL24, and human lymphoma line Ramos were obtained from the American Type Culture Collection (Manassas, Va.); HEK293 (human embryonic kidney cells) parent and TLR7-transfected lines from Imgenex (San Diego, Calif.); and Leukopak human peripheral blood leukocytes (PBMC) from BRT Laboratories Inc. (Baltimore, Md.). Melanoma cells were cultured in RPMI 1640 media supplemented with 5% fetal bovine serum, 1% Pen/Strep and 1% L-glutamine; hereafter referred to as RPMI (Gibco, Grand Island, N.Y.).

Additional cell lines and types of cancer were used and are described in the figures. For example, ovarian cancer cell lines (OVCAR3, CaOV3, SKOV3, OV90, and COV413), breast cancer cell lines (BRC173, MB468, MDAMB453, and MCF7), and lung cancer cell lines (NCIH522, H1299, A549, VBT2, H460, SKLU1, H358, and Calu-1).

TLR Staining.

Melanoma cell lines were seeded into 6-well plates at $1 \times 10^6$ cells/well in RPMI and stimulated overnight in the presence or absence of recombinant human IFNγ (rh-IFNγ, 1000 IU/mL; PeproTech, Rocky Hill, N.J.). After stimulation, cells were detached using Accutase (Millipore, Billerica, Mass.), stained with indicated antibodies and fixed using Cytofix (BD Biosciences, San Jose, Calif.). *Surface staining antibodies*: TLR2-Alexa647, Streptavidin-PE (BD Pharmigen, San Jose, Calif.), TLR6-Biotin (eBioscience, San Diego, Calif.), TLR4-APC (R&D Systems, Minneapolis, Minn.). *Intracellular staining*: cells were fixed and permeabilized using the BD Cytofix/Cytoperm kit (BD Biosciences) and stained with appropriate antibodies: TLR7-CFS, IgG2α-CFS (R&D Systems), TLR3-PE, TLR9-APC (eBioscience), TLR8-Alexa488 (Dendritics, San Diego, Calif.), IgG1-PE, and IgG2α-PE (Caltag, Towcester, UK).

Flow Cytometric Analysis.

Stained cells were collected on the FACSCalibur instrument (BD Biosciences) and analyzed with FlowJo 8.8.6 software (TreeStar, Ashland, Oreg.). Analyses were conducted on live cells (95%) as defined by forward and side-angle scatter. Gates were set based on isotype-matched (ISO) controls or fluorescence-minus-one (FMO) controls.

TLR Stimulation.

For intracellular cytokine staining, melanoma cell lines were seeded into 6-well plates at $1 \times 10^6$ cells/well in RPMI and individually stimulated with TLR agonists or PMA and Ionomycin overnight in the presence of GolgiStop (1 μL/mL, BD Biosciences) at 37° C., at these concentrations: LPS (10 μg/mL), CpG ODN (5 μg/mL), resiquimod (5 μg/mL), imiquimod (25 μg/mL), MALP-2 (100 ng/mL; Imgenex), poly-ICLC (20 μg/mL), FSL-1 (5 μg/mL; InvivoGen, San Diego, Calif.), PMA (60 ng/mL) and Ionomycin (1 mg/mL; Sigma-Aldrich, St. Louis, Mo.). These were used with or without rh-IFNγ (1000 IU/mL; PeproTech). After stimulation, cells were detached using Accutase.

Intracellular Chemokine Staining.

Cells were fixed and permeablilized using the BD Cytofix/Cytoperm kit and then stained with the indicated antibodies. Staining antibodies: CCL2-PE, CCL3-PE, CCL4-PE, CCL5-PE, CXCL10-PE (BD Pharmingen), CXCL9-PE, CXCL12-APC (R&D Systems), IgG1-PE, and IgG2α-PE (Caltag). Flow cytometric analyses were conducted as described.

ELISA Assay.

Melanoma cell lines or cells from patient samples were stimulated with TLR agonists as described, but without GolgiStop. Media containing the cell-secreted chemokines were collected and centrifuged to remove cell debris. CXCL10 was measured using the BD OptEIA human IP-10 ELISA Set with BD OptEIA buffers (BD Biosciences).

CFSE Assay.

Melanoma cells were stained with the CellTrace CFSE Cell proliferation kit 5 m/$1 \times 10^6$ cells (Life Technologies, Carlsbad, Calif.), prior to treatment with TLR agonists and flow cytometric analysis.

Apoptosis Assay.

Melanoma cells were treated with TLR agonists as described then stained with CellEvent Caspase-3/7 Green Flow Cytometry kit according to manufacturer instructions (Life Technologies). Apoptosis was assessed by flow cytometric analysis.

Statistical Analysis.

p values were calculated using the paired Student's t-test. p values less than 0.05 were considered significant.

For analysis of synergy: levels of CXCL10 induced by TLR stimulation alone and IFNγ stimulation alone were added together and compared to the induction of CXCL10 after the combined treatment TLR +IFNγ by the paired student's t-test. p values less than 0.05 were considered significant for synergistic upregulation.

Results

Melanoma Cells Encode TLRs, but Produce Little Chemokine in Response to TLR Agonists.

Figure 7A:
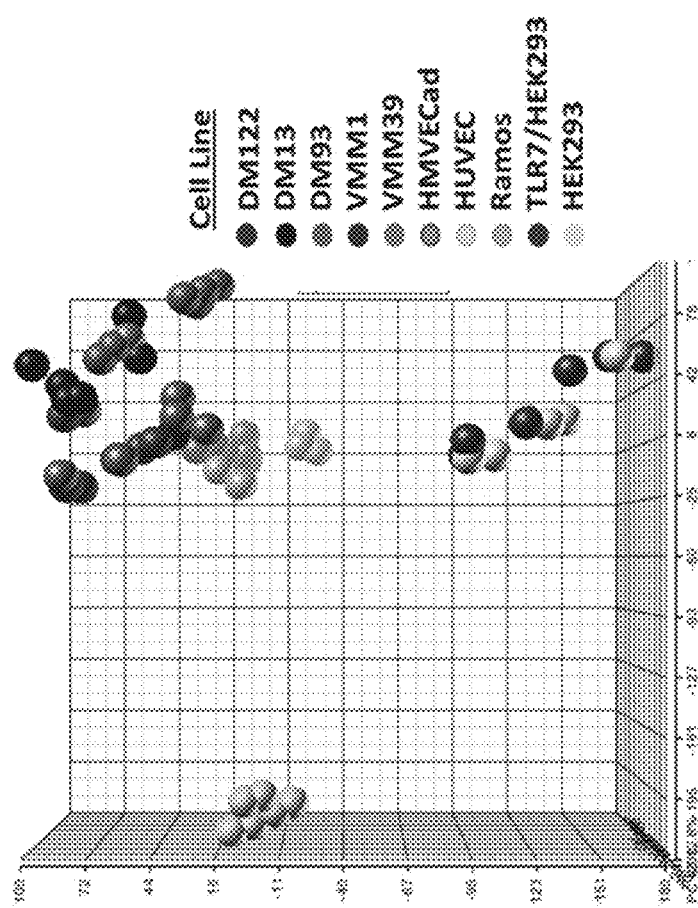
FIGS. 7A-7E. Melanoma cells display minimal changes in gene expression for chemokines CCL2-5 or CXCL9-12 in response to TLR stimulation, or TLR and IFNγ stimulation.
Figure 7B:
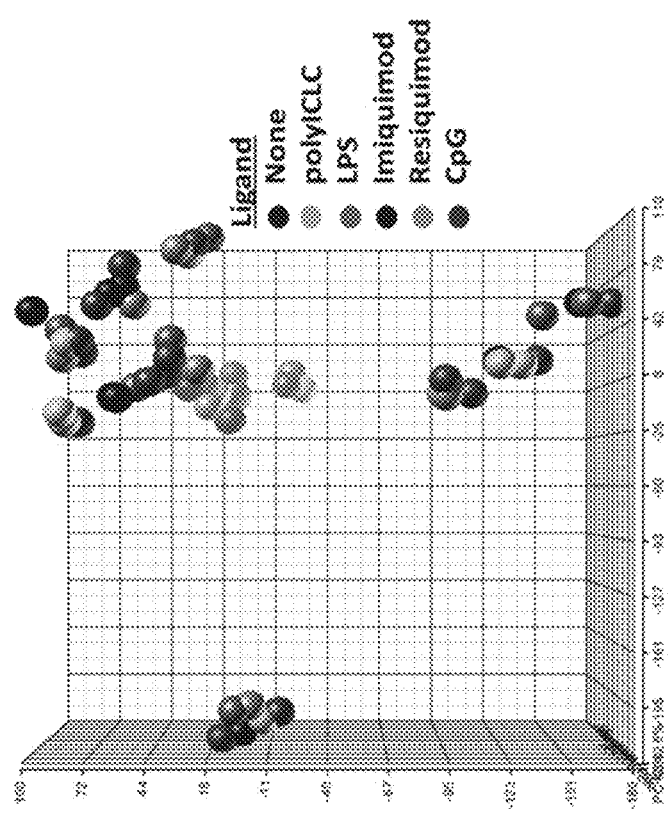
Figure 7C:
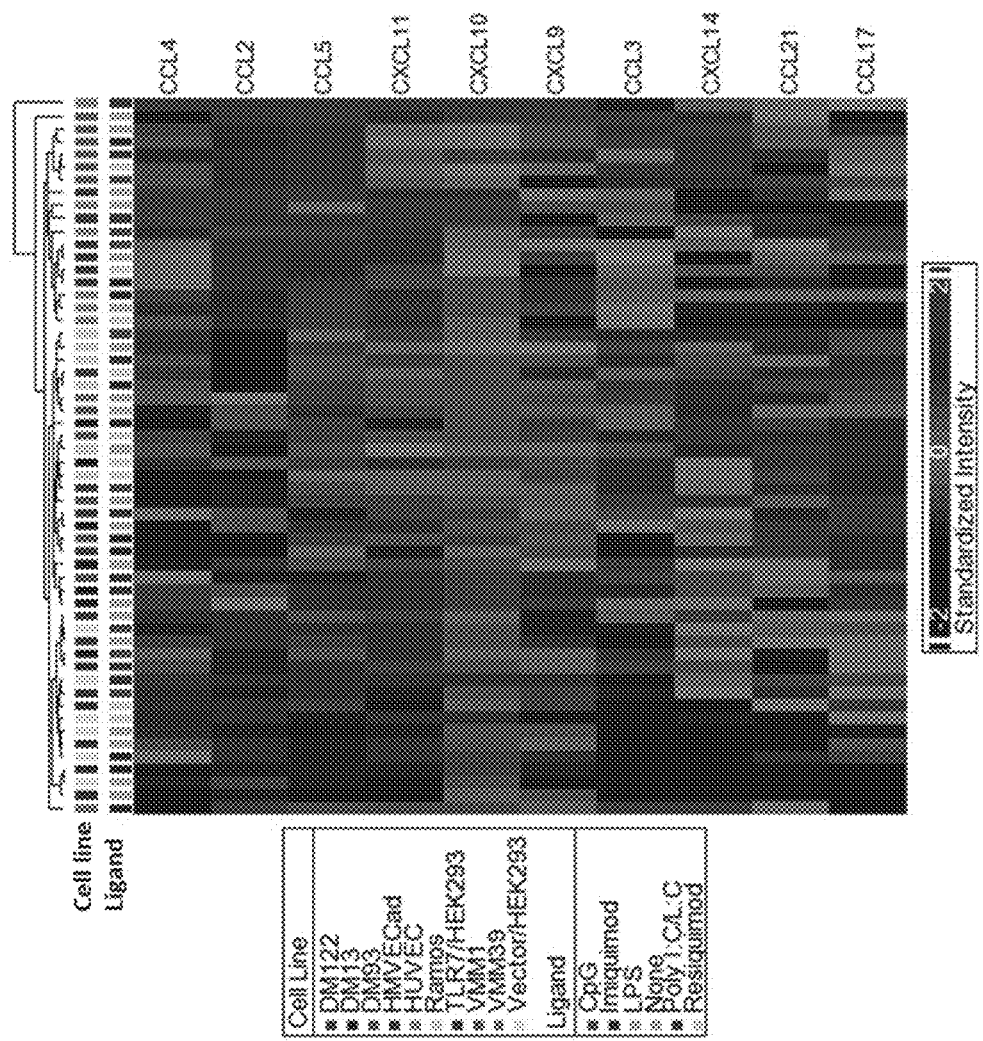

Gene expression profiling of four human melanoma cell lines VMM1, DM13, DM93 and DM122 revealed expression of TLRs 1, 3, 4, and 6, when compared to HEK293 cells which lack TLR expression (FIG. 1A). Effects of TLR agonist stimulation on gene expression profiles were assessed for the following cell lines: the four melanoma cell lines; 3 melanoma metastasis biopsies (TPF 15529, 15100, and 15289); limited assessment of a $5^{th}$ melanoma line (VMM39); HEK293 and TLR7-HEK293 cells; endothelial cell lines (HUVEC and HMVECad) and Ramos cells, which express most TLRs. Principal component analysis indicated that TLR stimulation had only modest effects on each melanoma cell line, and that the melanoma lines clustered together, and separately from endothelial, Ramos, and HEK lines (FIGS. 7A-7B).

Figure 1B:
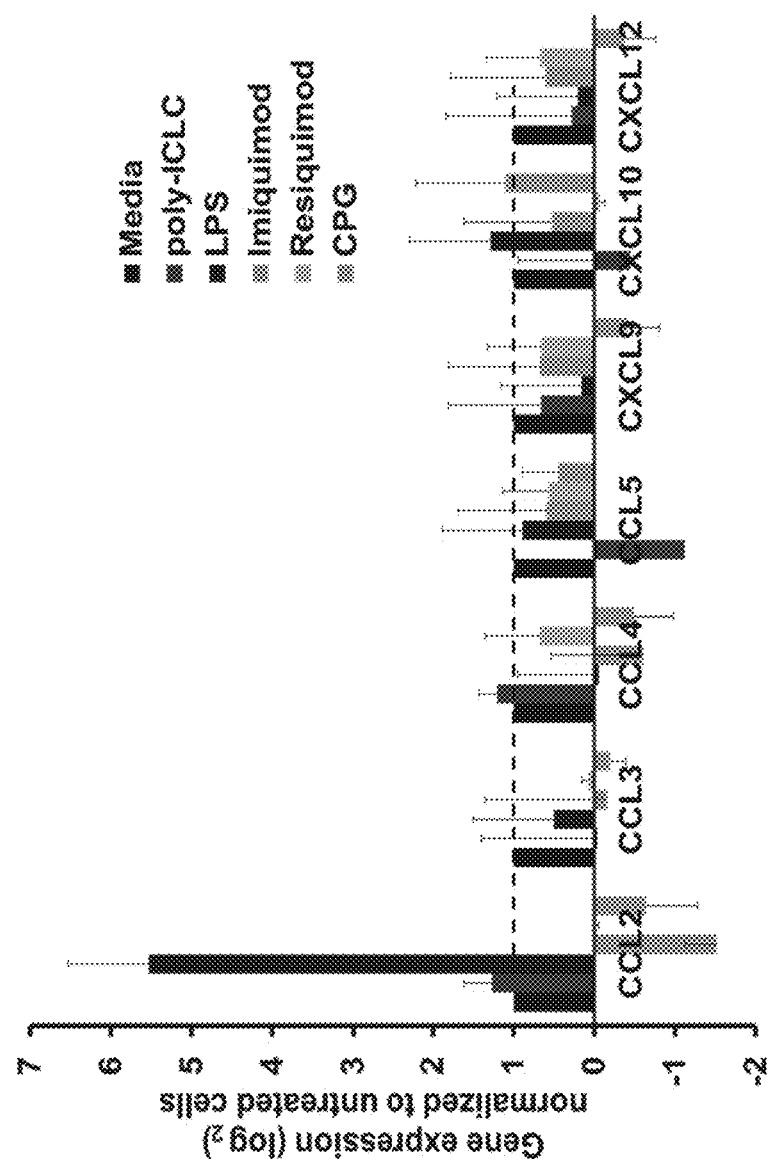

Chemokines CCL2-5, CXCL9-10, and CXCL12 support T-cell recruitment to tissues (15); we assessed whether melanoma cells could produce them constitutively or after TLR stimulation. Changes in expression of those genes encoding chemokines suggested possible effects of TLR3 and TLR4 agonists on individual cell lines (FIGS. 7C, 8, and 9A-9E), but when analyzed across all 4 cell lines, no effects on those chemokine genes were significant (FIG. 1B).

Figure 1C:
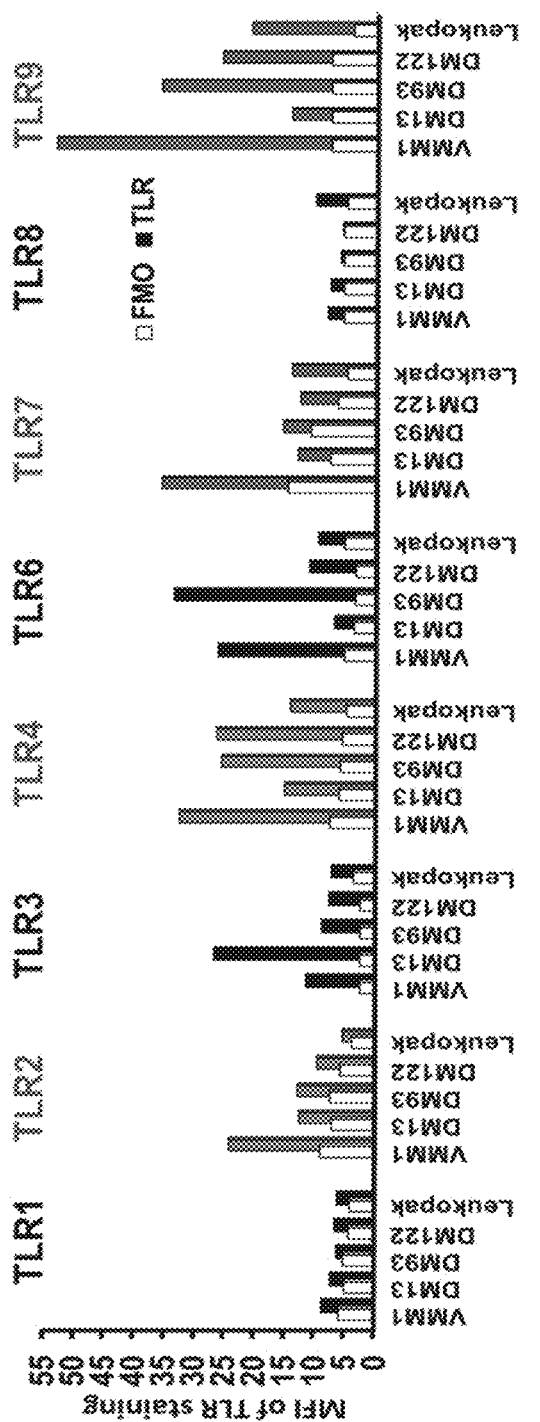
Figure 1D:
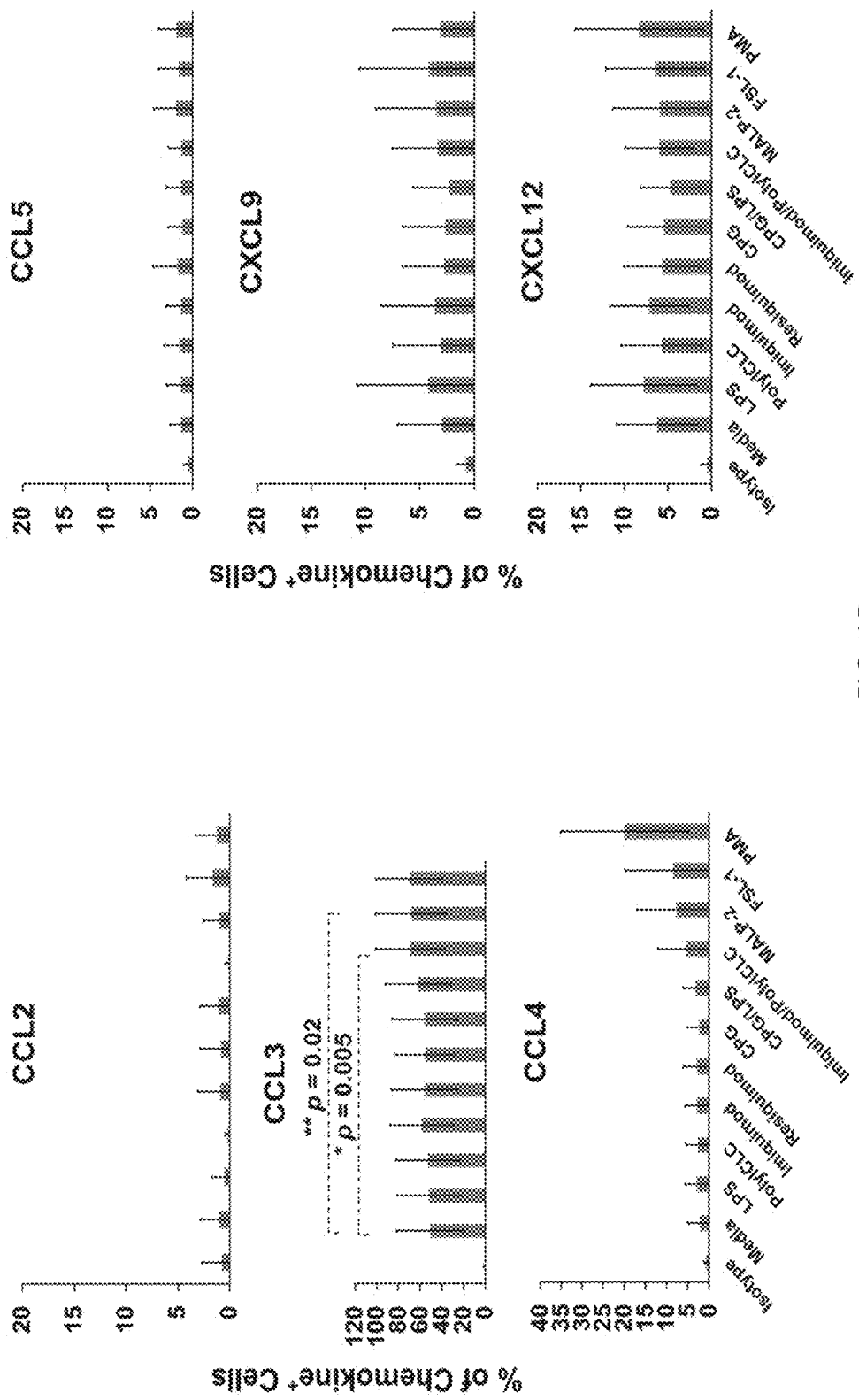

We also examined the four (4) melanoma lines by flow cytometry for TLR expression and production of chemokines after TLR ligation. TLRs 2-4, 6, 7, and 9 were detected on several or all 4 cell lines and on PBMC (FIG. 1C). We tested effects of the same TLR agonists evaluated in the gene array, plus two combinations (imiquimod+poly-ICLC; LPS+CpG). Since melanoma cells expressed TLR6 genes (FIG. 1A), TLR2/6 agonists (MALP-2 and FSL-1) were also tested. TLR6 interacts with TLR2 to form a functional receptor that binds the bacterial lipoprotein MALP-2 and its synthetic homologue FSL-1 (20). Less than 10% of melanoma cells produced CCL2, CCL4-5, CXCL9, and CXCL12, constitutively (FIG. 1D, media only controls); however, greater than 50% produced CCL3 (FIG. 1D). TLR agonists did not significantly alter production of CCL2, CCL4-5, CXCL9, or CXCL12; however TLR2/6 agonists increased CCL3 production, compared to unstimulated cells (FIG. 1D).

Melanoma Cells Upregulate CXCL10 Production Upon Stimulation with TLR2/6 Agonists and IFNγ.

Figure 7D:
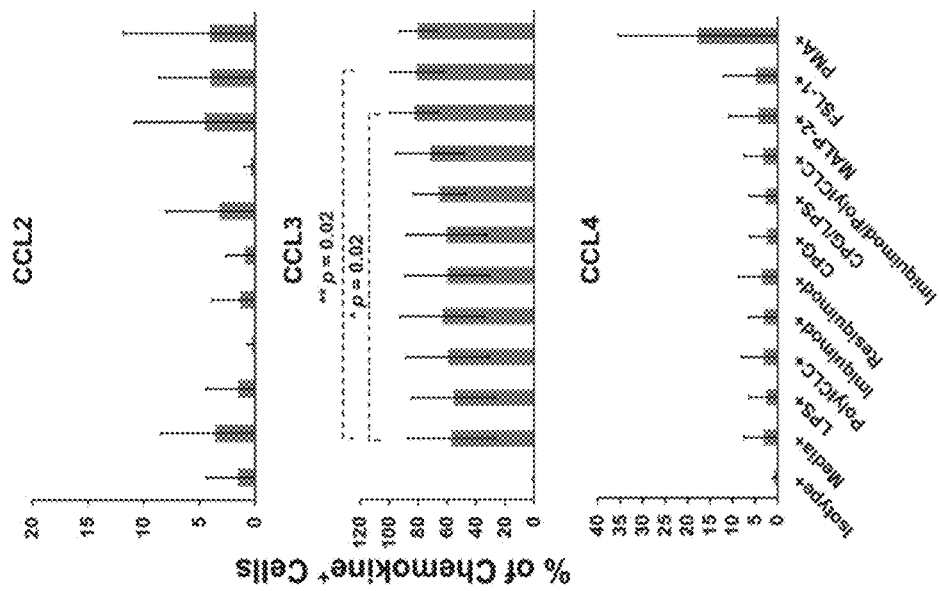
Figure 7E:
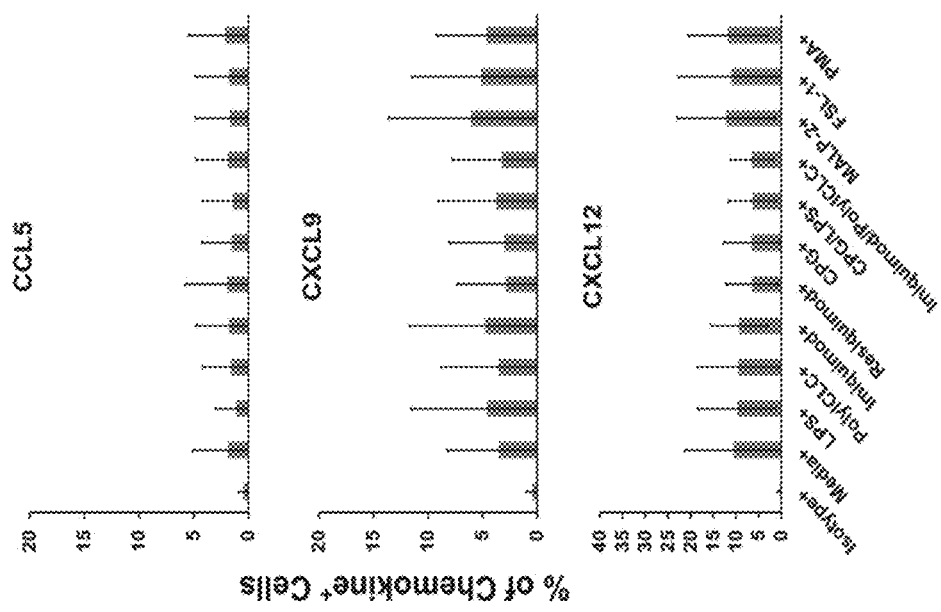
Figure 8:
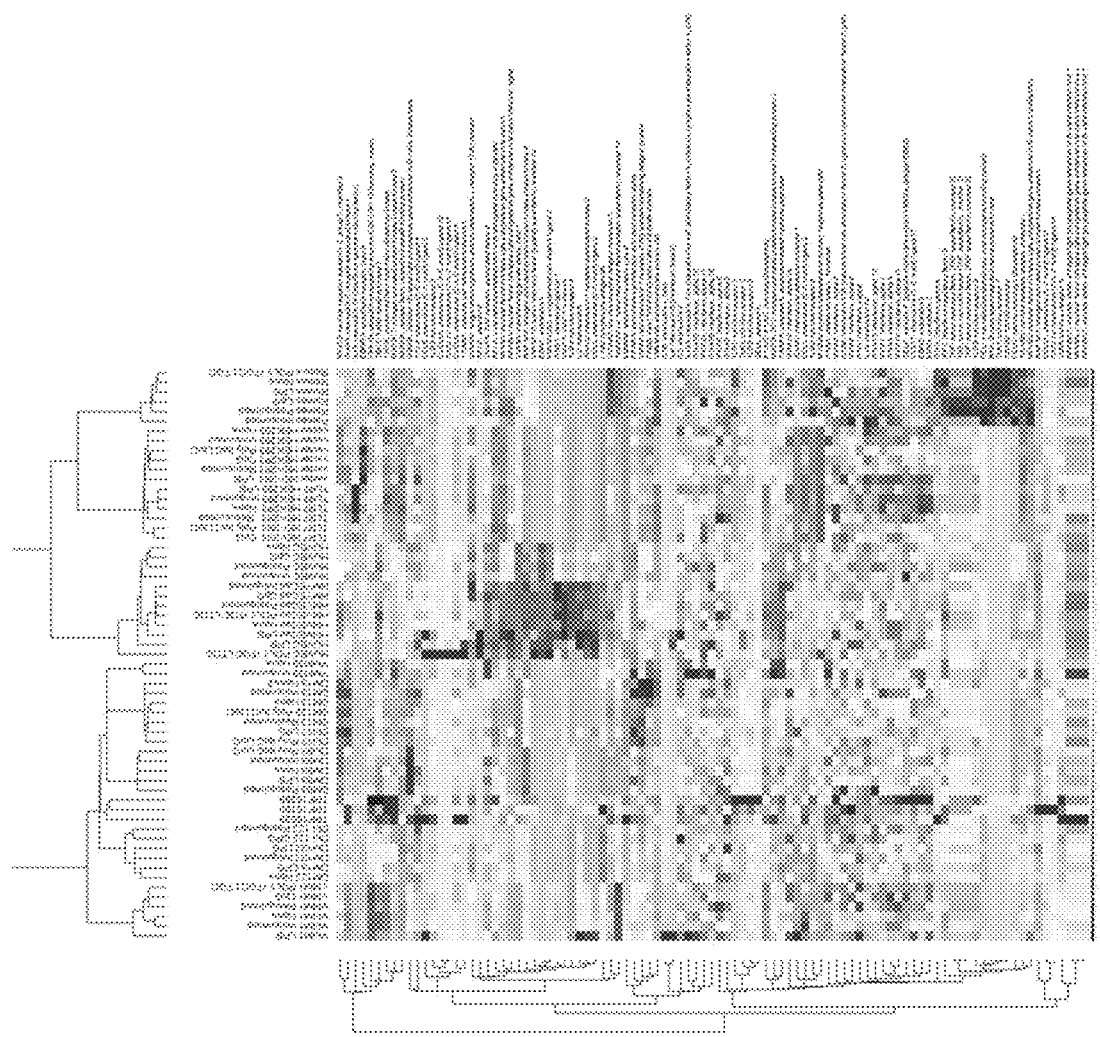
FIG. 8. Heat map of TLR-associated gene expression in melanoma cell lines and controls with and without TLR stimulation. Unsupervised hierarchical clustering of data from GeneChip Analysis to examine associations between TLR stimulation and chemokine expression. A subset of transcripts that encode classical TLR associated genes were used for clustering; data are from one experiment.
Figures 9A, 9B:
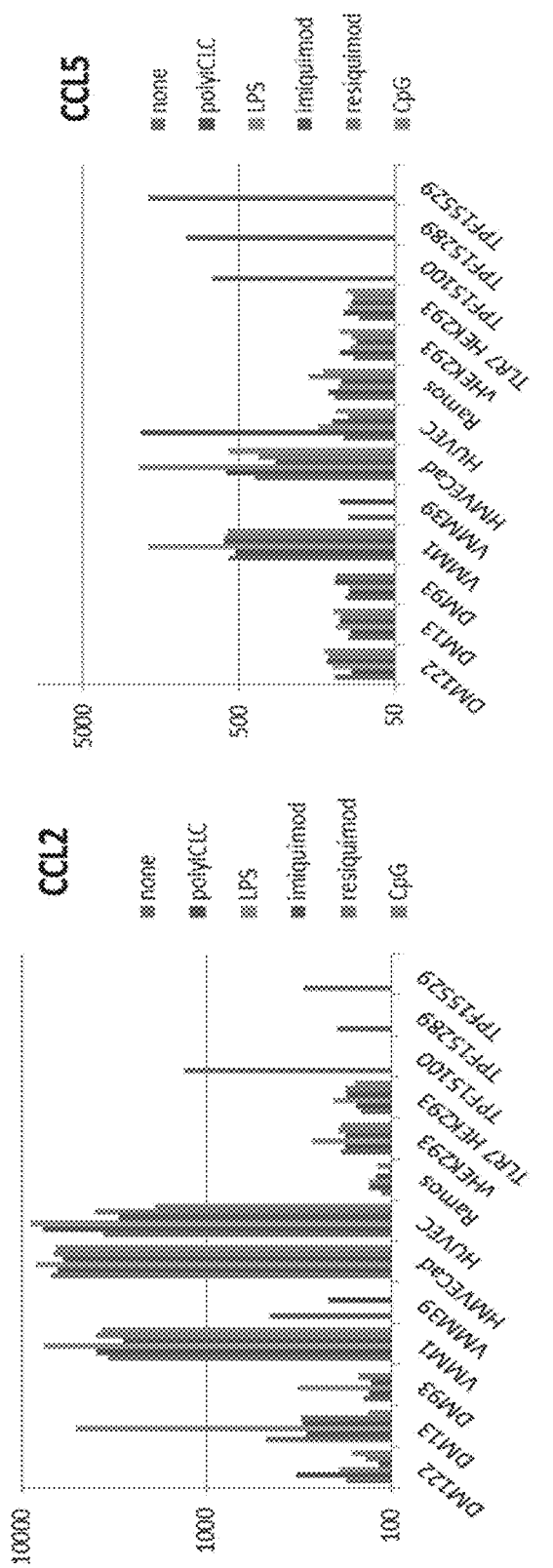
FIGS. 9A-9E. Expression of selected chemokine genes by melanoma cell lines and controls after TLR stimulation. Graphed data are signal intensity values from GeneChip Analysis to examine associations between TLR stimulation and chemokine expression. Signal intensity data for the expression profile of CCL2 (FIG. 9A), CCL5 (FIG. 9B), CXCL9 (FIG. 9C), CXCL10 (FIG. 9D), and CXCL11 (FIG. 9E) are shown; data represent one experiment.
Figures 9C, 9D:
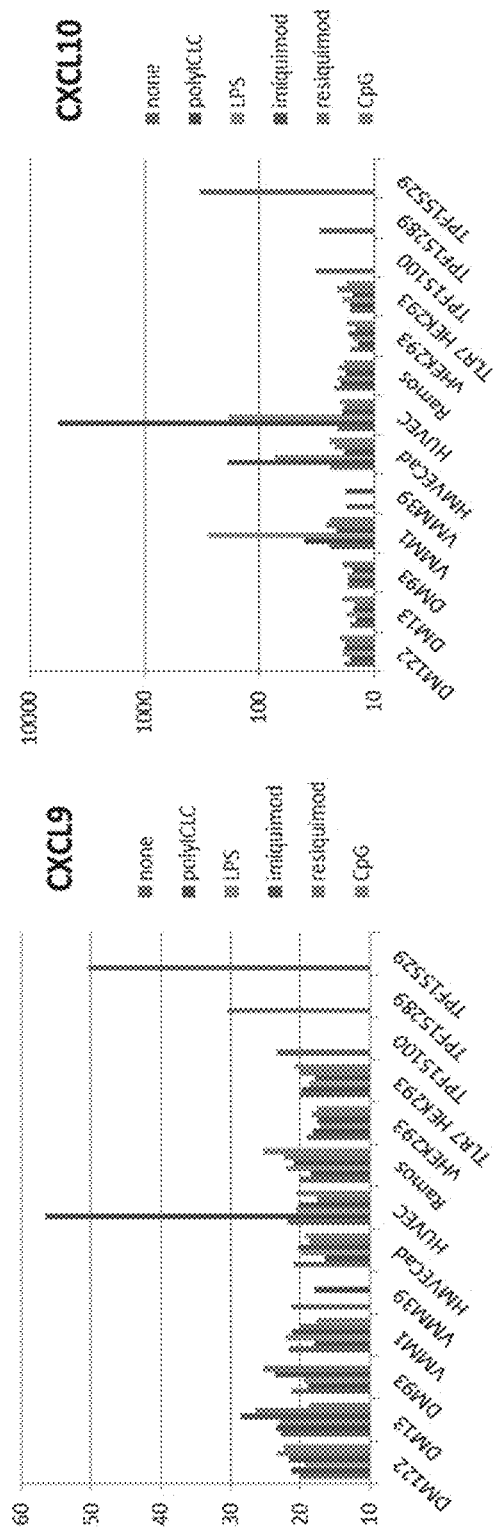
Figure 9E:
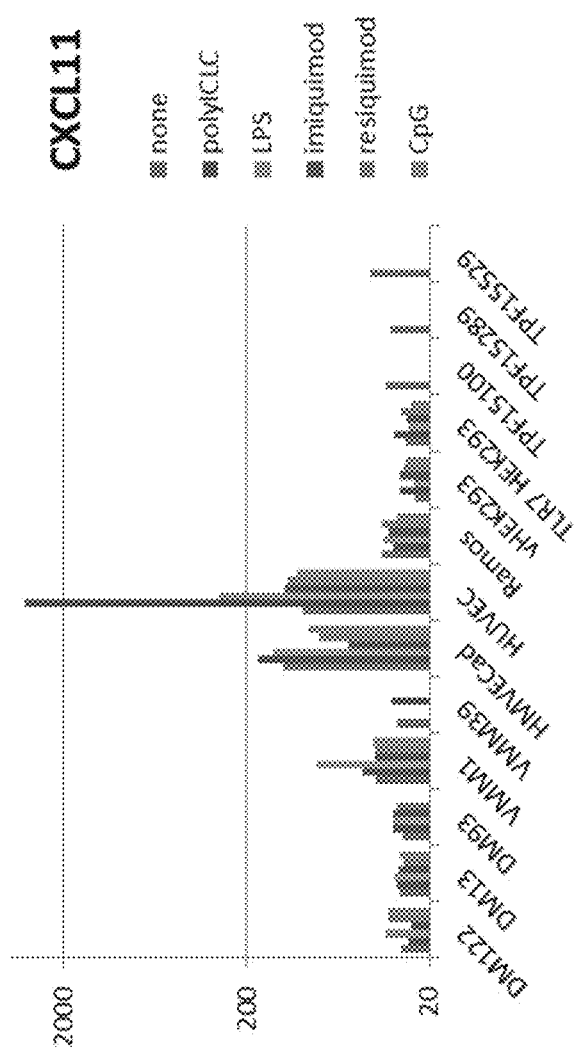

IFNγ stimulation of melanoma cells induces CXCL9 and CXCL10 (11); thus, we tested whether IFNγ combined with TLR ligation may induce chemokine production by melanoma cells (11). We assessed chemokine expression in four human melanoma lines stimulated with TLR agonists and IFNγ. While there was no effect on CCL2, CCL4-5, CXCL9, or CXCL12 (FIGS. 7D-7E), CCL3 production was enhanced from melanoma cells treated with TLR2/6 agonists +IFNγ compared to IFNγ stimulation alone (FIG. 7D), but this effect was similar to that with TLR2/6 agonists alone (FIG. 1D).

Figure 2A:
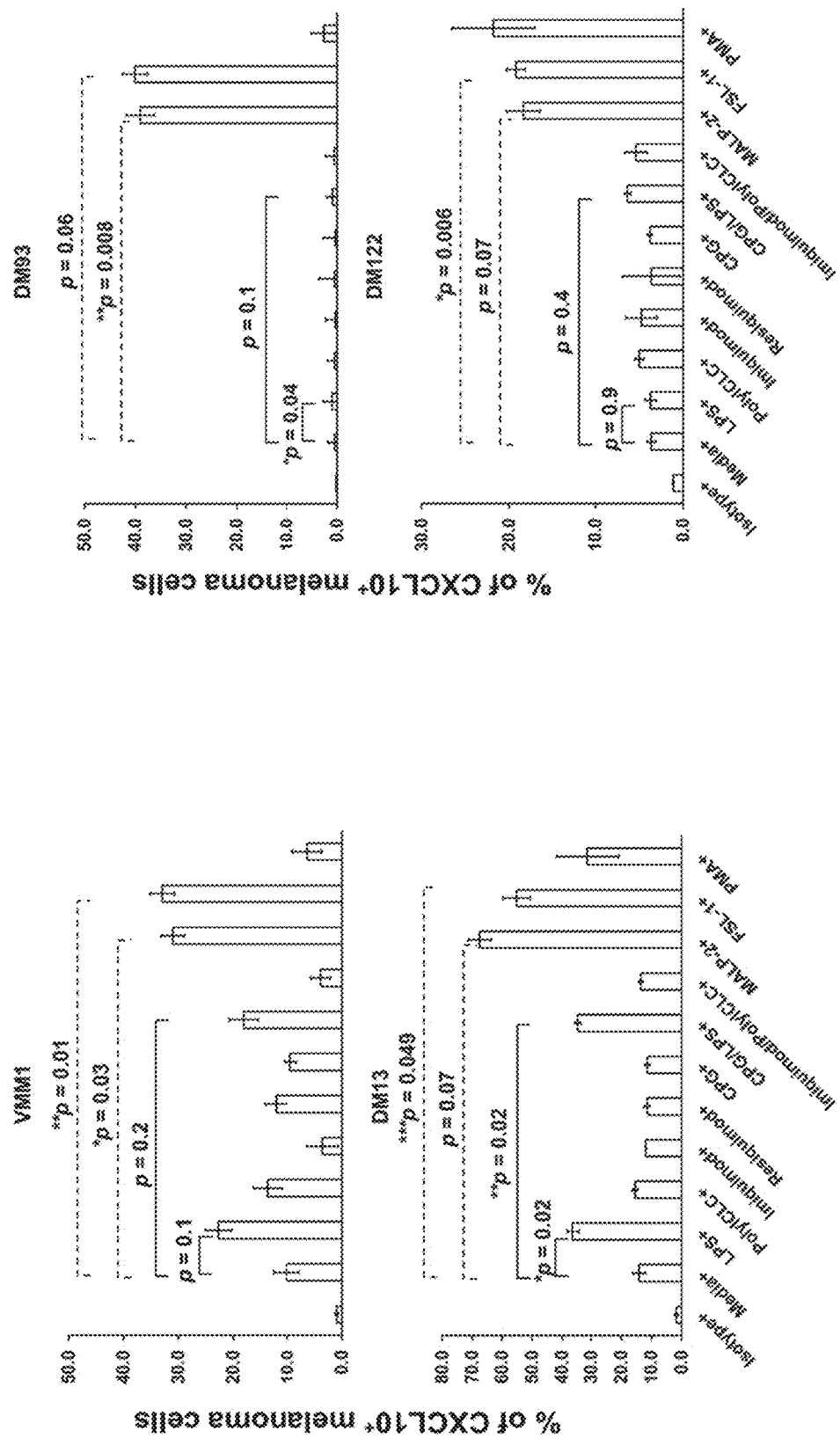
FIGS. 2A-2C. Melanoma cells upregulate CXCL10 production in response to TLR2/6 agonists and IFNγ treatment. VMM1, DM13, DM93, and DM122 melanoma cells were analyzed by flow cytometry for CXCL10 production after overnight stimulation with the indicated TLR agonists with or without IFNγ.
Figure 2B:
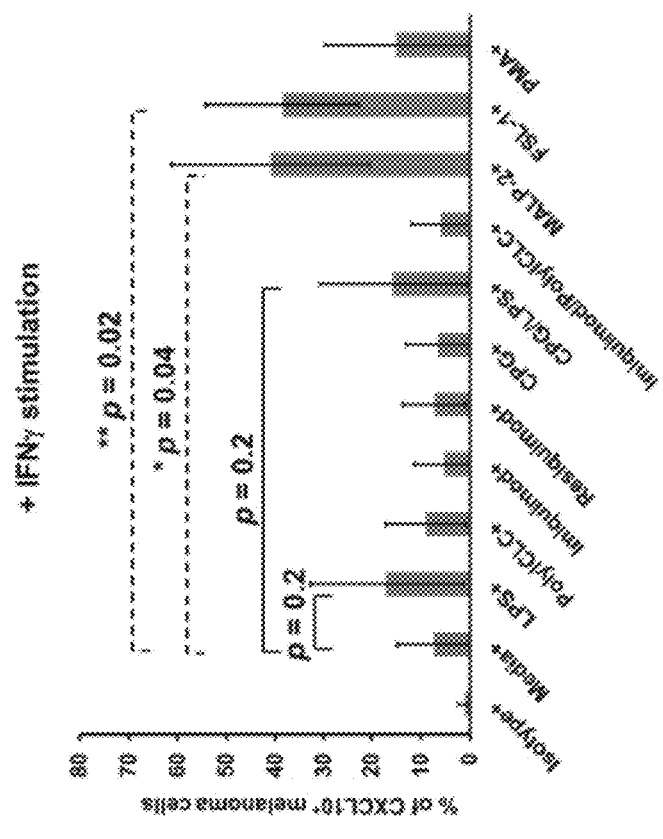
Figure 2B:
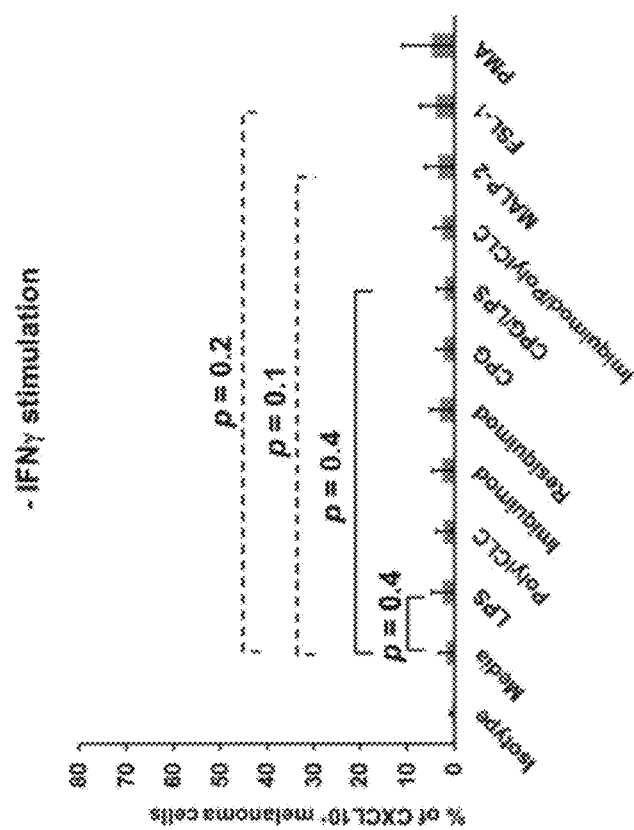
Figure 2C:
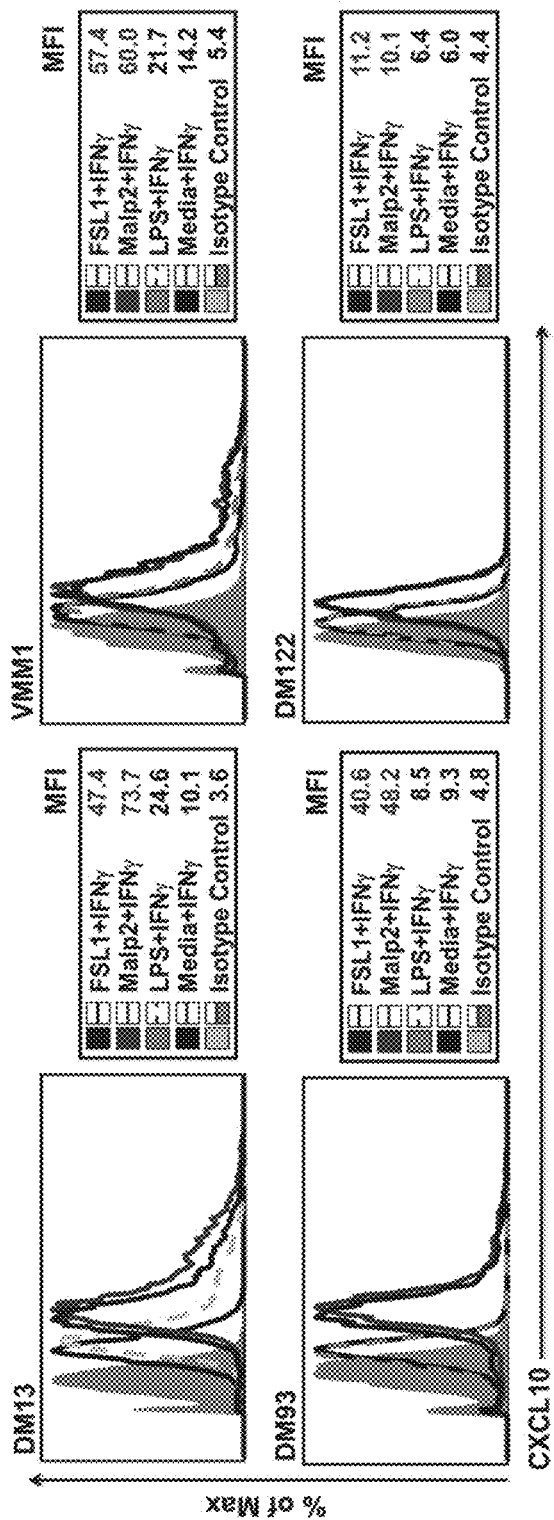

The proportion of melanoma cells producing CXCL10 increased strikingly after stimulation with TLR2/6 agonists +IFNγ in all four melanoma cell lines tested, compared to IFNγ alone (FIG. 2A). LPS +IFNγ treatment also increased the percentage of CXCL10 producing cells in DM13 and DM93 cell lines, however the TLR2/6 agonists +IFNγ induced greater increases in CXCL10 (FIG. 2A). When data were averaged across the four melanoma lines, the percent of cells producing CXCL10 in media alone was only 1.6% and did not increase after TLR stimulation alone (FIG. 2B, left panel). With IFNγ treatment alone, 7% of cells produced CXCL10 (media+control, FIG. 2B, right panel), however TLR2/6 agonists +IFNγ induced CXCL10 production from a significantly higher percentage of melanoma cells (41% MALP-2/IFNγ, and 38% FSL-1/IFNγ) than either agent alone (FIG. 2B). As evidence for greater CXCL10 production on a per-cell basis, the mean fluorescence intensity (MFI) of CXCL10 for melanoma cells treated with TLR2/6 agonists +IFNγ was also increased, compared to TLR agonists or IFNγ alone (FIG. 2C).

Figure 3A:
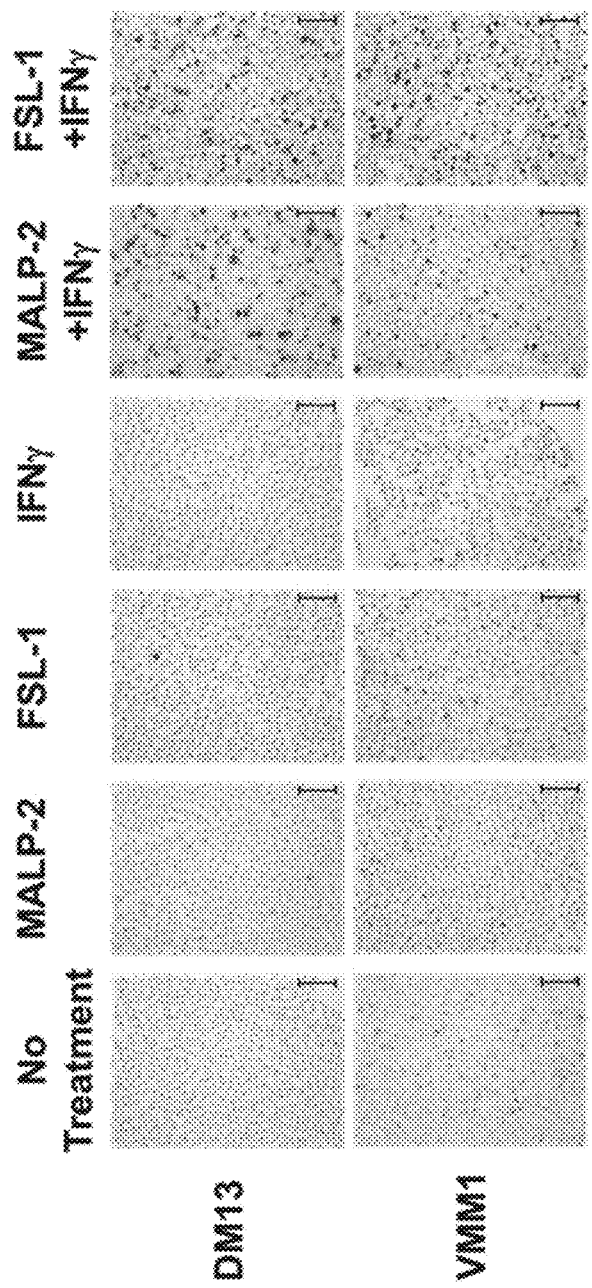
FIGS. 3A-3D. Melanoma cells upregulate CXCL10 production in response to TLR2/6 agonists and IFNγ treatment. Melanoma cells were analyzed for induced chemokine production after overnight stimulation with the indicated TLR agonists with (+) or without (−) IFNγ.
Figure 3B:
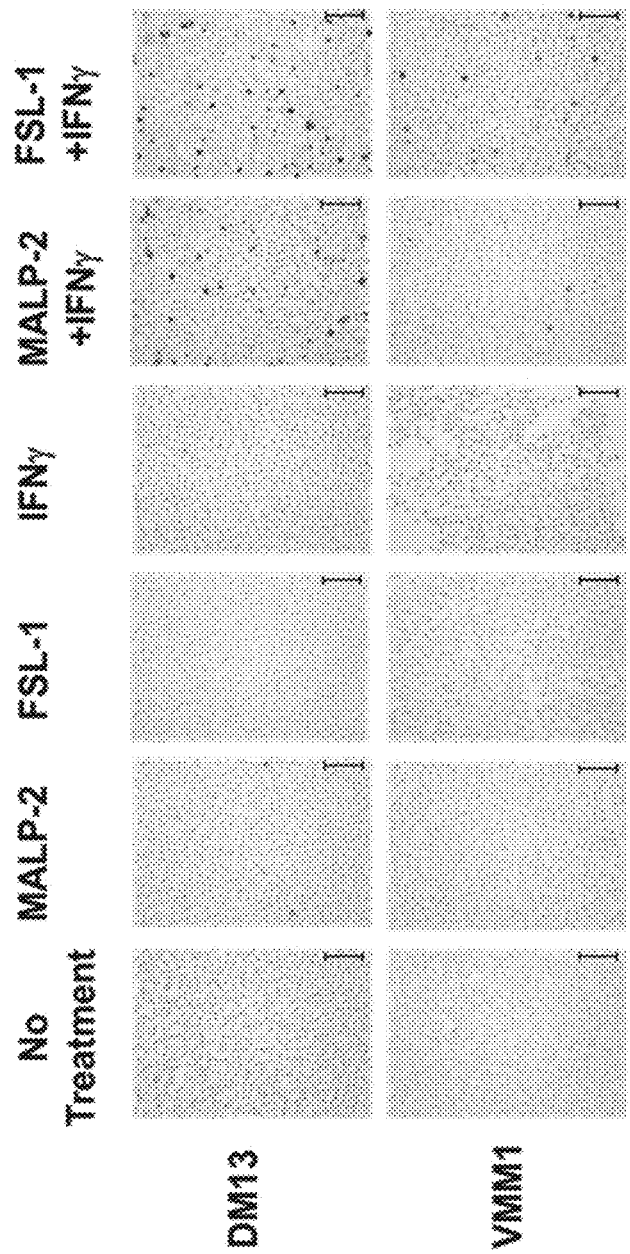
Figure 3C:
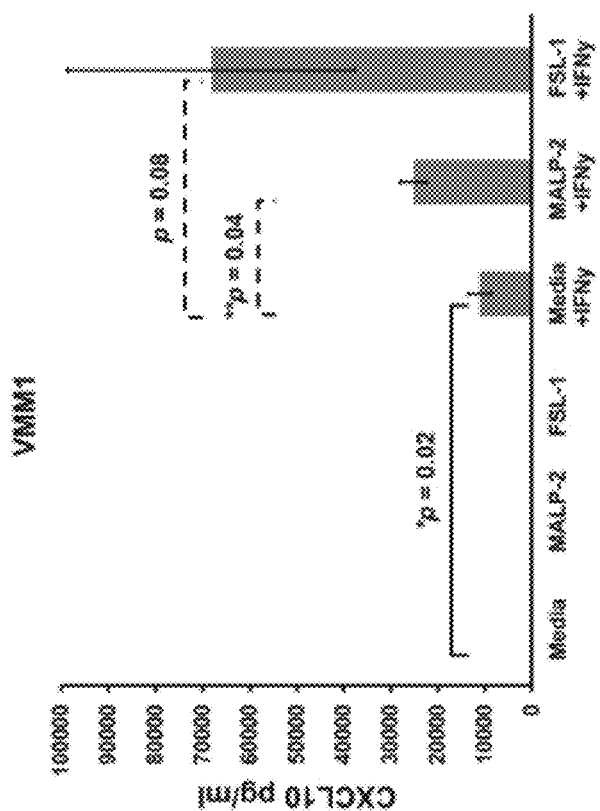
Figure 3C:
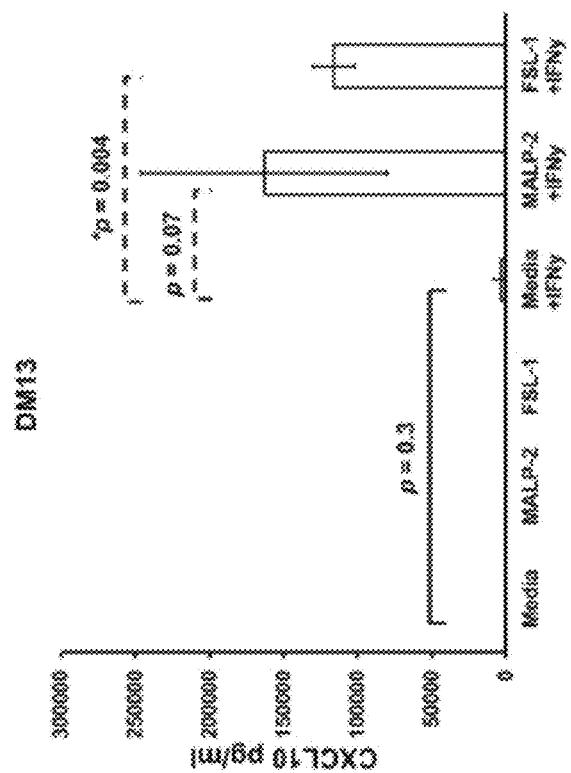

Additionally, there was a robust increase in CXCL10 staining after MALP-2 or FSL-1 +IFNγ treatment (FIG. 3A) and modest induction of CXCL9 (FIG. 3B), as assessed by immunohistochemistry for both cell lines tested. CXCL10 secreted into supernatants by two melanoma lines also increased after stimulation with MALP-2 or FSL-1 and IFNγ compared with unstimulated or IFNγ treated cells (FIG. 3C).

Figure 3D:
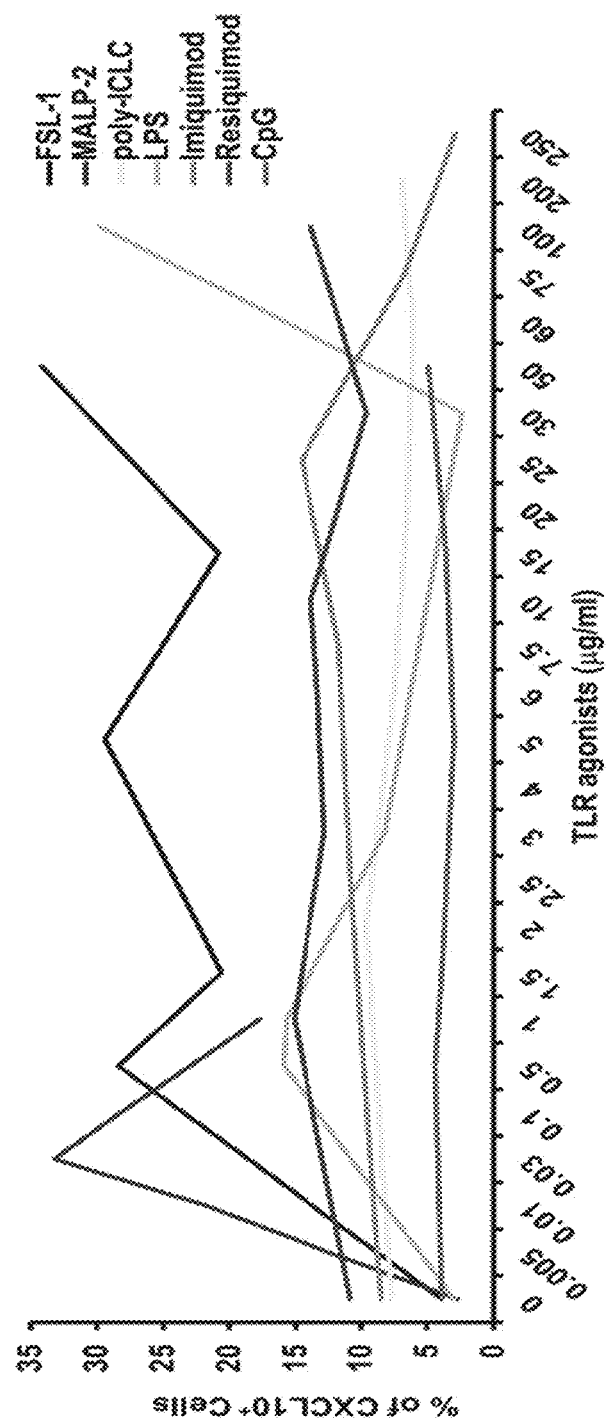

Few studies have evaluated effects of MALP-2 or FSL-1 on melanoma cells (21; 22). Having observed the synergy of combining TLR2/6 agonists +IFNγ, we sought to determine concentrations of TLR2/6 agonists optimal for melanoma cell stimulation in conjunction with IFNγ and to assess whether other TLR agonists may have similar or greater activity. Dose-response assays assessing CXCL10 production induced by a variety of TLR agonists across a range of concentrations, with a constant concentration of IFNγ, showed that MALP-2 at 100 ng/ml and FSL-1 at 5 μg/ml were optimal. On the other hand, TLR agonists CpG, resiquimod, imiquimod, and poly-ICLC, in the presence of IFNγ, had little effect on CXCL10 induction, even at much higher concentrations than we had used in prior experiments. However, very high concentrations of LPS (100 μg/ml) +IFNγ induced CXCL10 at levels comparable to the much lower doses of MALP-2 or FSL-1 and IFNγ (FIG. 3D).

TLR2/6 Ligation does not Impact Melanoma Apoptosis or Proliferation.

Figure 4A:
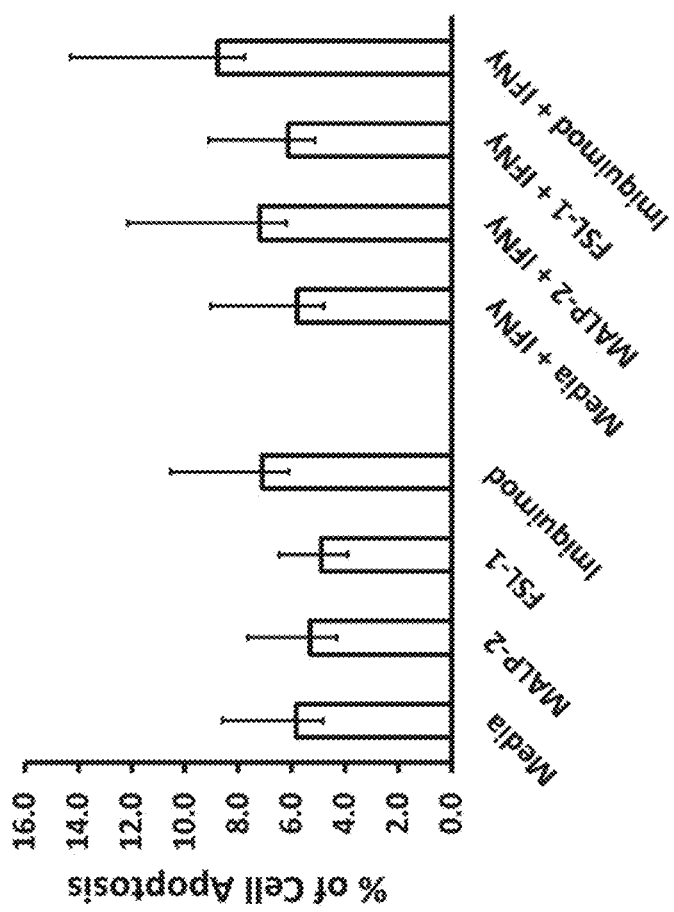
FIGS. 4A and 4B. TLR2/6 ligation does not significantly impact melanoma apoptosis, proliferation, or the expression of common melanoma antigens. Melanoma cells were analyzed after overnight stimulation with TLR2/6 agonists +/−IFNγ.
Figure 4B:
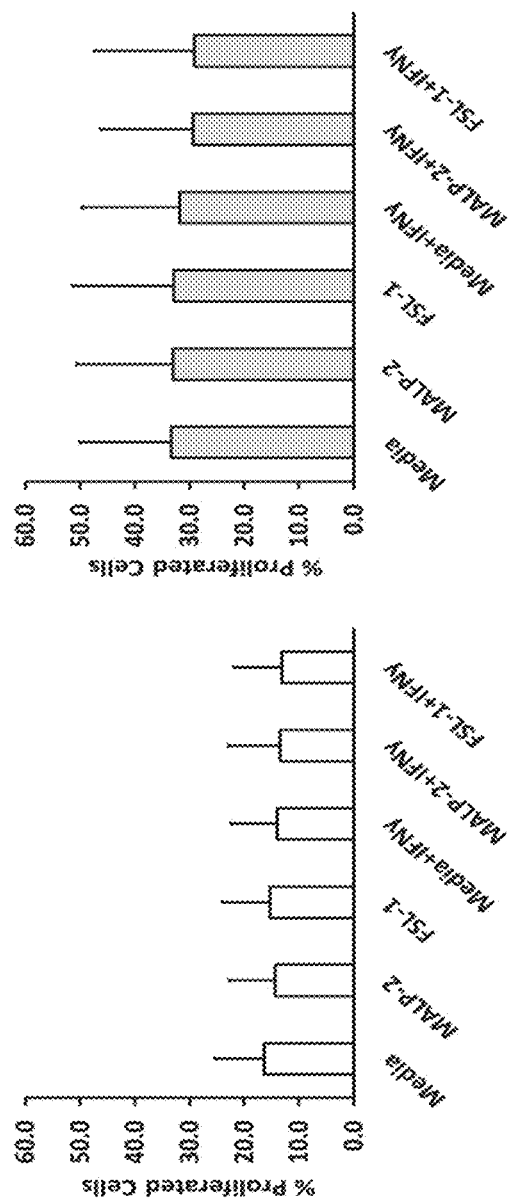

TLRs signal through MAPK, PI3K-Akt, and NF-κB which have key roles in regulating cell proliferation and survival (23; 24). Thus, TLR ligation can impact proliferation or apoptosis of some cell types (23; 25; 26). We asked if TLR2/6 ligation would enhance proliferation or inhibit apoptosis of melanoma cells, which if observed may be deleterious clinically. TLR2/6 ligation, with or without IFNγ, did not hinder melanoma cell death (FIG. 4A). Furthermore, at both 24 and 48 hours post TLR2/6 ligation +IFNγ there was no significant effect on melanoma cell proliferation (FIG. 4B).

TLR2/6 Ligation does not Impact MHC or Gp100 Expression by Melanoma but Downregulates Melan-A/MART-1 Expression.

Figure 10A:
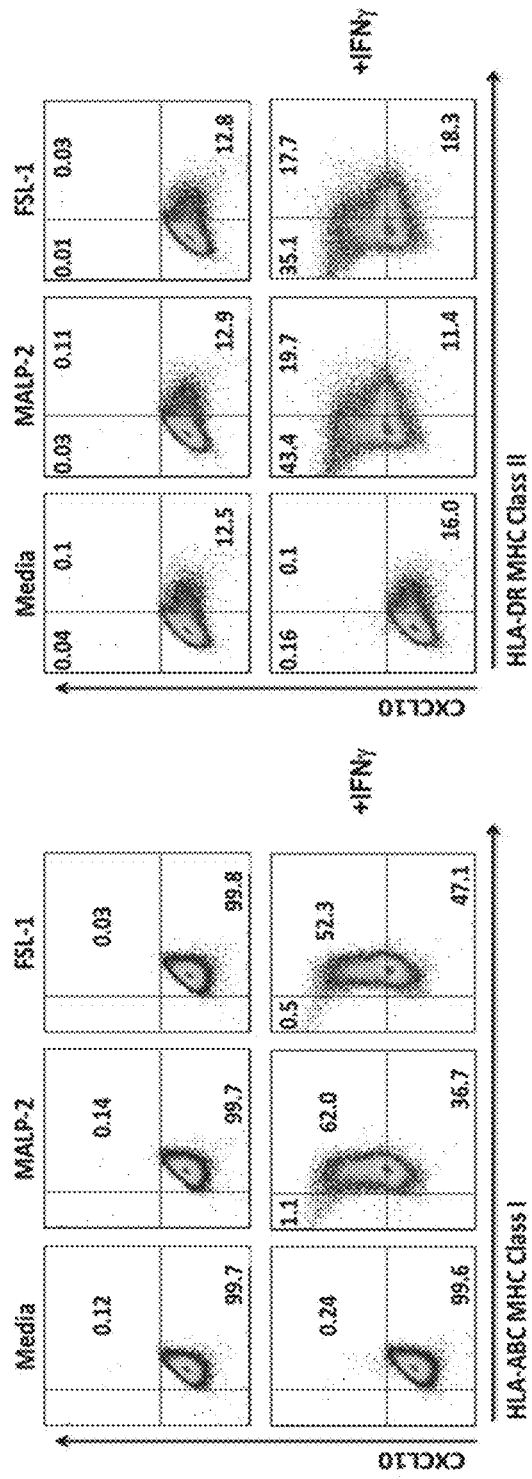
FIGS. 10A and 10B. TLR2/6 ligation does not impact MHC or gp100 expression but downregulates Melan-A/MART-1 expression from melanoma. Melanoma cells were analyzed after overnight stimulation with TLR2/6 agonists+/−IFNγ and compared with untreated cells also denoted here as media alone.
Figure 10B:
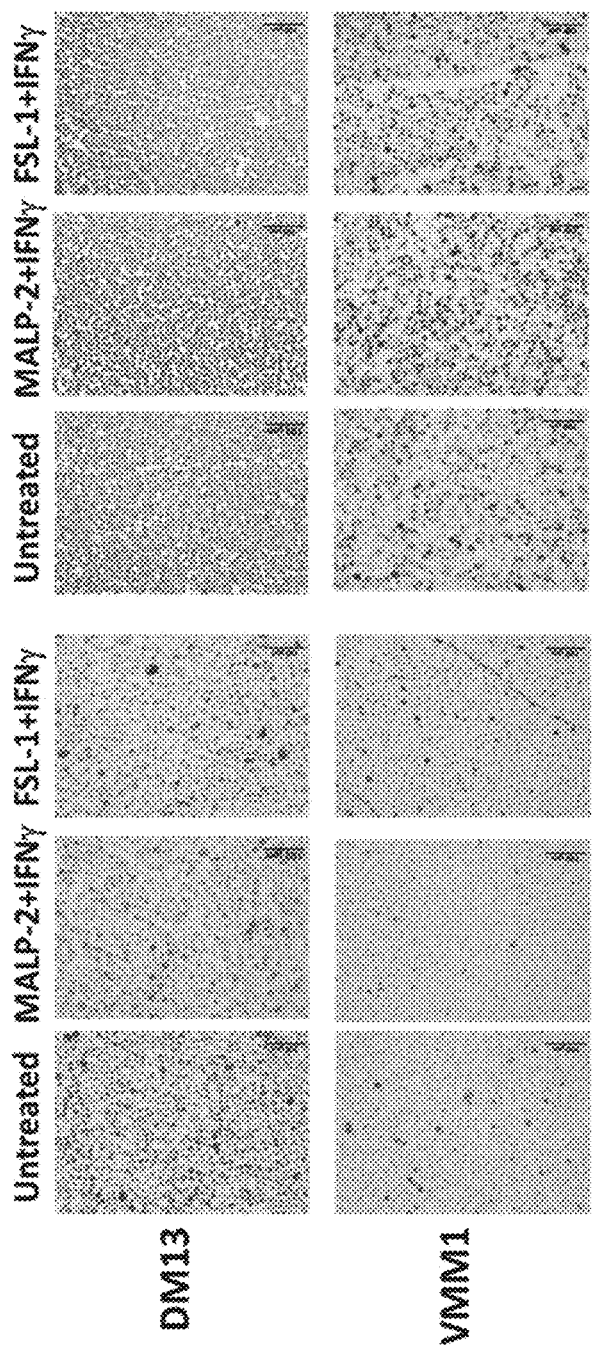

T cell mediated recognition of cancer cells requires expression of MHC and of tumor antigens. Expression of MHC molecules is increased in cells stimulated with IFNγ (27; 28) and the TLR7 agonist imiquimod has been reported to decrease MITF and tyrosinase expression by melanocytes (29). We evaluated whether TLR2/6 agonists and IFNγ impact expression of MHC Class I and II molecules and melanoma antigens gp100, and Melan-A/MART-1. For the 4 melanoma cell lines, we found that TLR2/6 ligation did not decrease MHC expression, and that TLR2/6 +IFNγ stimulation slightly enhanced expression of MHC Class II with no significant change in MHC Class I (FIG. 10A, and data not shown). By immunohistochemistry, we assessed expression of gp100 and Melan-A in VMM1 and DM13 melanoma cells. Melan-A expression was slightly downregulated after TLR2/6 agonists+IFNγ treatment while gp100 expression was unchanged (FIG. 10B).

TLR2 and TLR6 are Widely Expressed Among Melanoma.

Figures 5A, 5B:
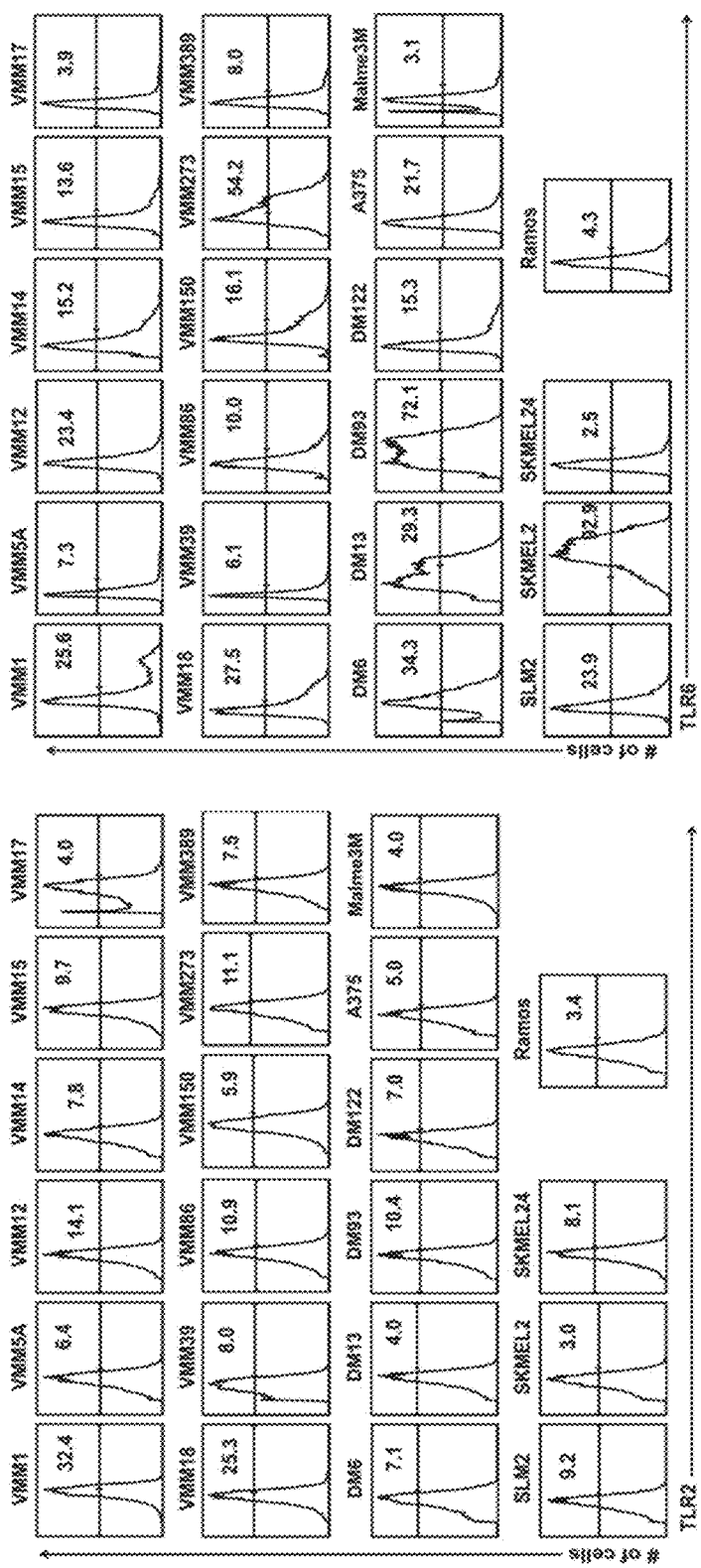
Figure 5C:
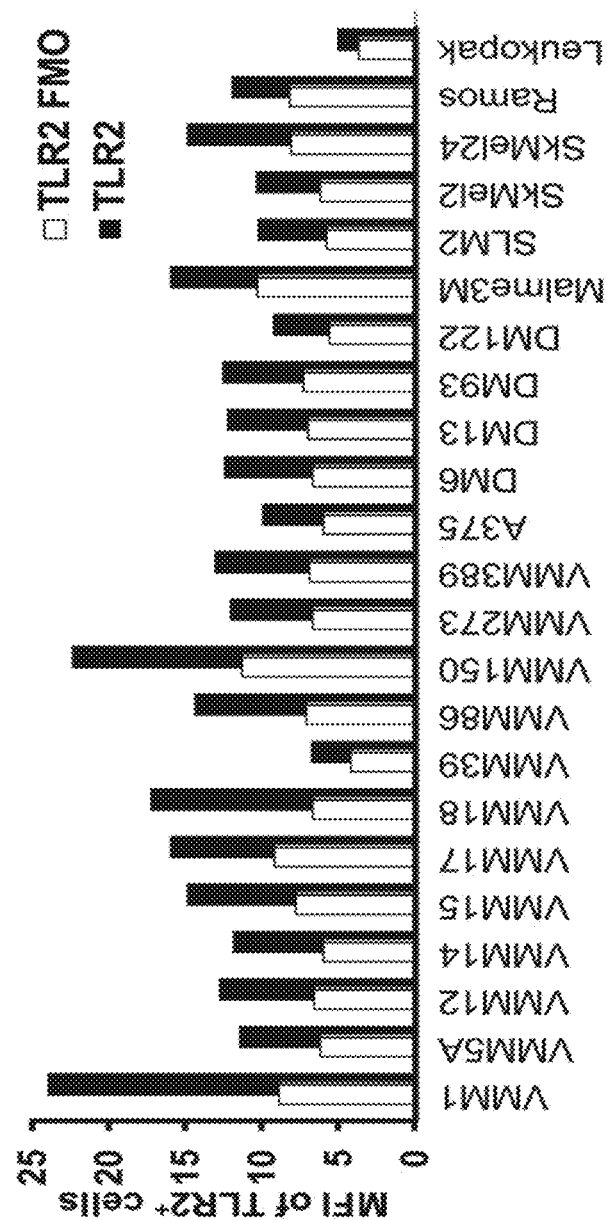
Figure 5D:
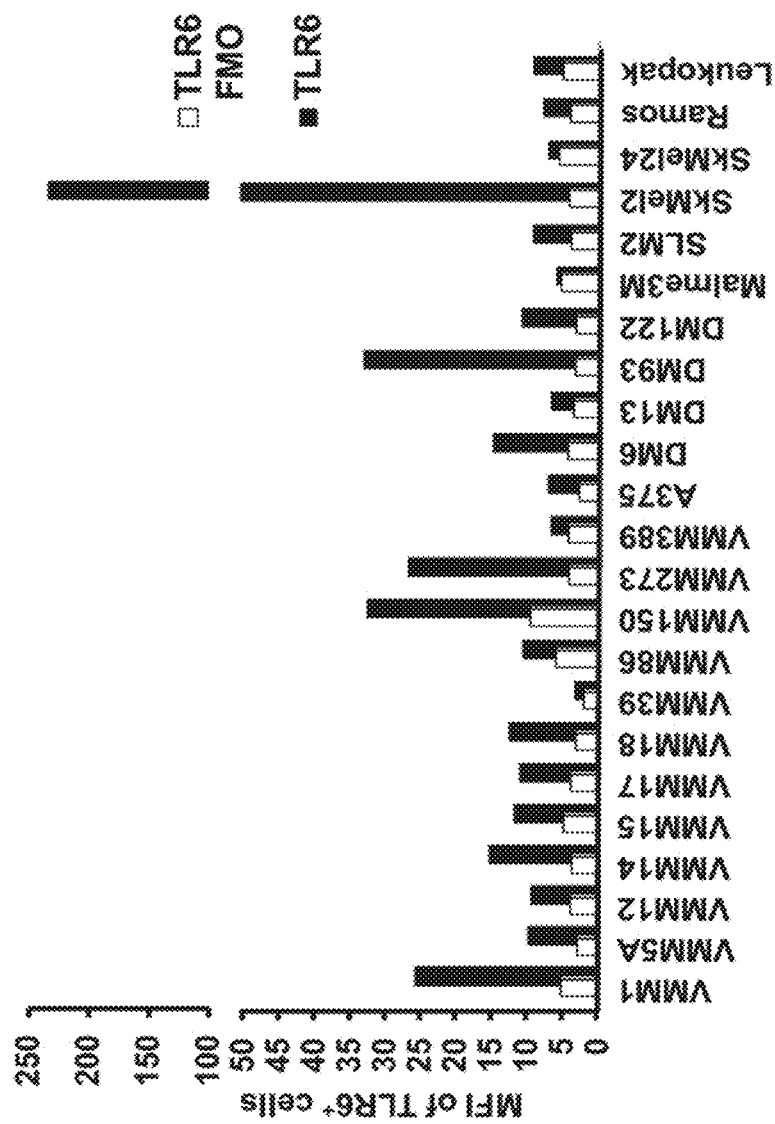

We had found that TLR2 and TLR6 were expressed among 4 melanoma cell lines; however, the potential future clinical application of TLR2/6 agonists depends on broad expression across a larger population. Thus, we assessed TLR2 and TLR6 expression for 21 melanoma cell lines, using Ramos cells and PBMC (Leukopak) as positive controls (FIGS. 5A-5B). Staining intensities (MFI) equal to or greater than those of Ramos cells were considered positive. We found that 20 of the 21 screened melanoma lines expressed TLR2 (FIGS. 5A & 5C), while 17 of the 21 expressed TLR6 at levels comparable to or greater than Ramos cells (FIGS. 5B & 5D). Slightly lower level expression may also be significant; so these serve as minimum estimates. TLR2 and TLR6 were widely expressed amongst the 21 tested melanoma cell lines, with 17 cell lines (81%) expressing both TLRs at levels higher than Ramos cells.

Interferons modulate expression of TLRs on a variety of cells, and have been reported to enhance signaling downstream of TLR ligation (30). Thus, we assessed whether IFNγ modulated expression of TLR2 or TLR6 on the same twenty-one (21) melanoma cell lines, but found that neither was impacted by IFNγ stimulation in these studies (data not shown).

Surgically Excised Human Melanoma Cells Produce CXCL10 in Response to TLR2/6 Agonists and IFNγ Stimulation.

Figure 11A:
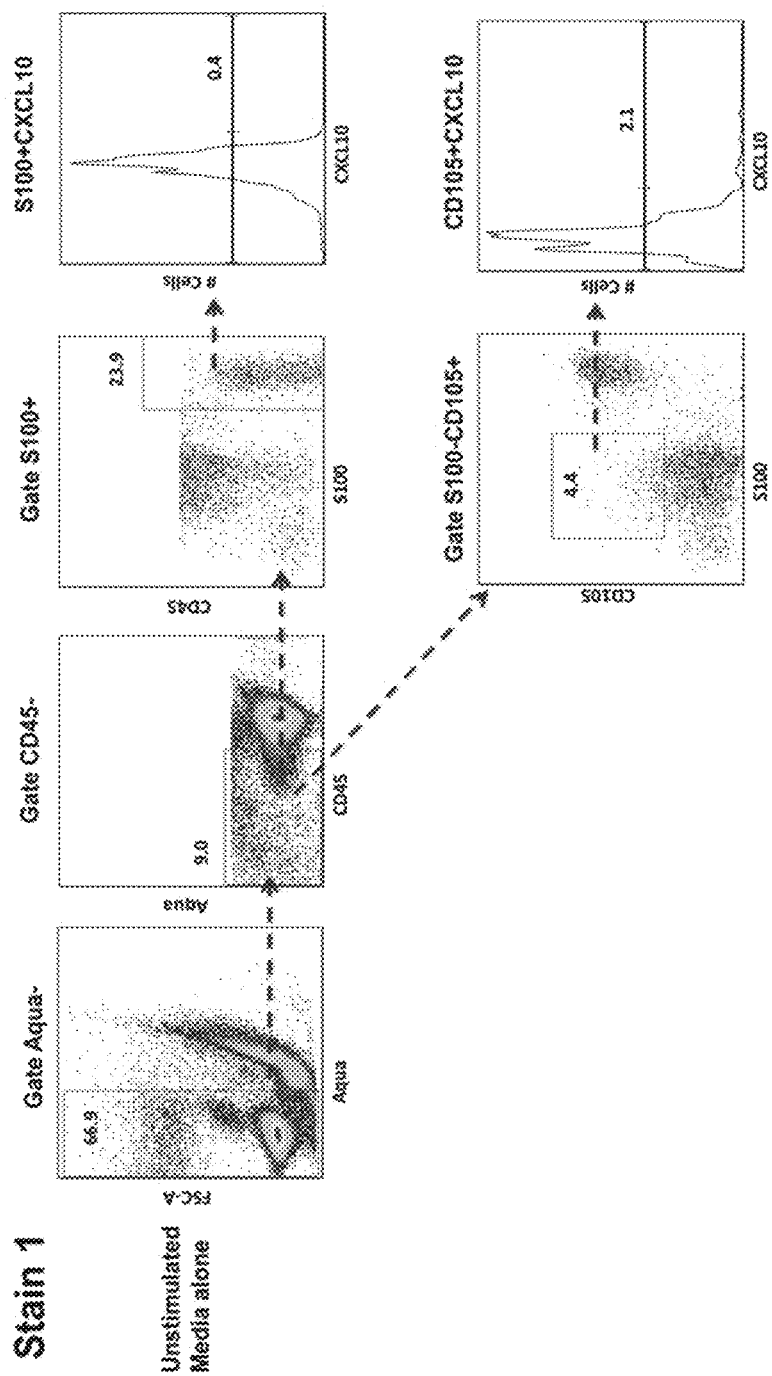
FIGS. 11A-11C. Patient melanomas generate CXCL10 in response to TLR2/6 agonist and IFNγ. Single cell suspensions of freshly resected human melanoma metastases were analyzed for induced CXCL10 production after stimulation with MALP-2 or FSL-1 +/−IFNγ by flow cytometric analysis. Images are representative gating and from Patient 1: melanoma is a metastasis to right axillary node.
Figure 11B:
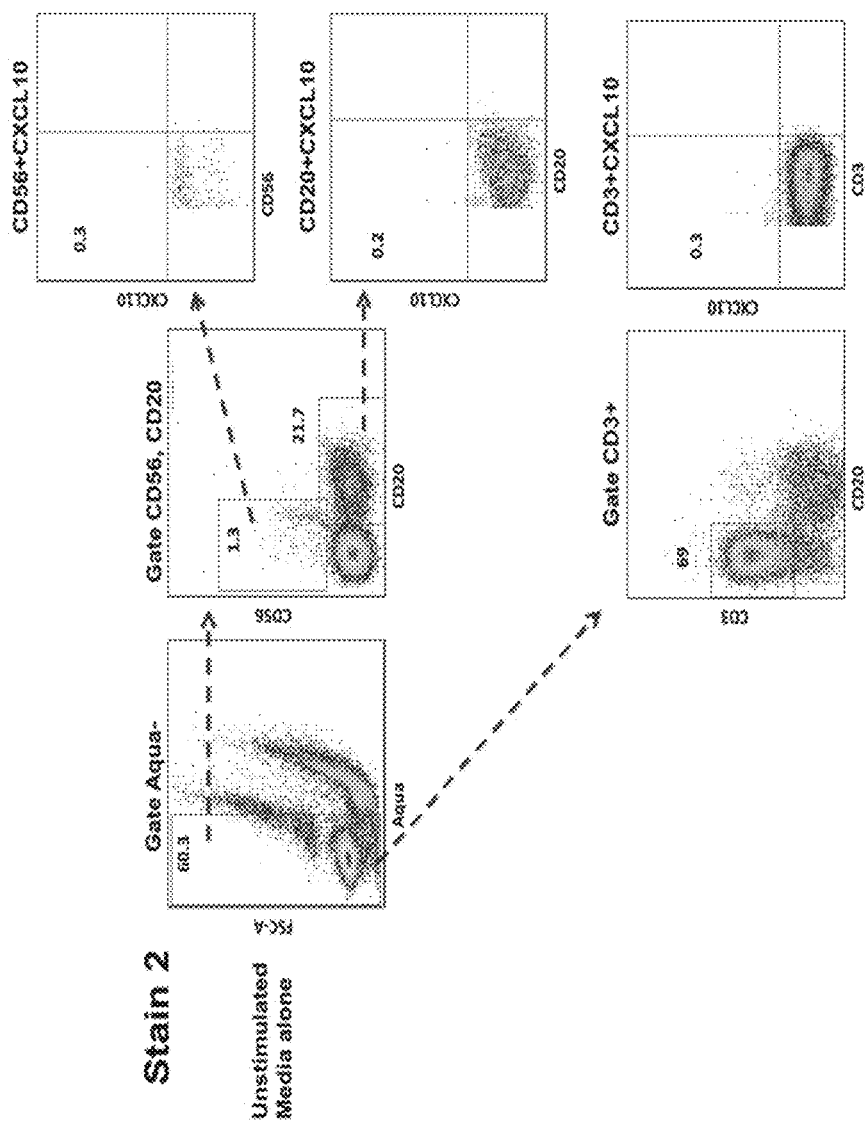
Figure 11C:
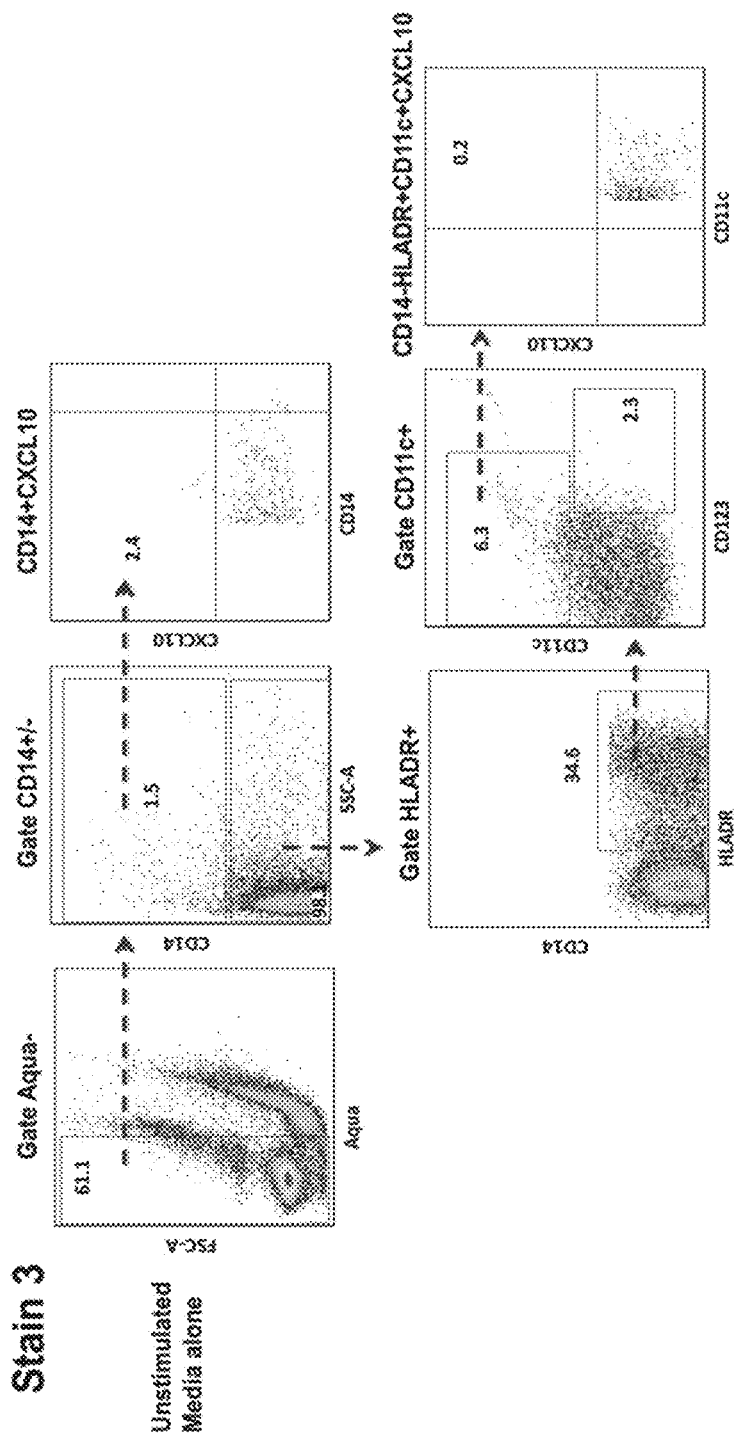

Having observed production of CCL3 and CXCL10 by cultured human melanoma cell lines in vitro, we asked whether the same would be observed with melanoma cells isolated from fresh surgically-excised human metastases. TLR2 and TLR6 are expressed on some immune cell subsets (31; 32), thus we also assessed whether TLR2/6 agonists and IFNγ may impact CXCL10 production from immune cell subsets in patient tumor specimens. Freshly resected melanoma specimens were studied from patients who required surgery for isolated distant melanoma metastases. Patient 1 had metastases to distant axillary nodes which were examined in this study. Patient's 2-4 each had small bowel metastases which were examined. FIGS. 11A-11C provide an example of the flow cytometric gating analyses performed on patient tumor samples. The percentage of live cells from tumor assessed by viability marker were approximately 60%, 50%, 70%, and 40% for patients 1-4 respectively (data not shown).

Figure 6A:
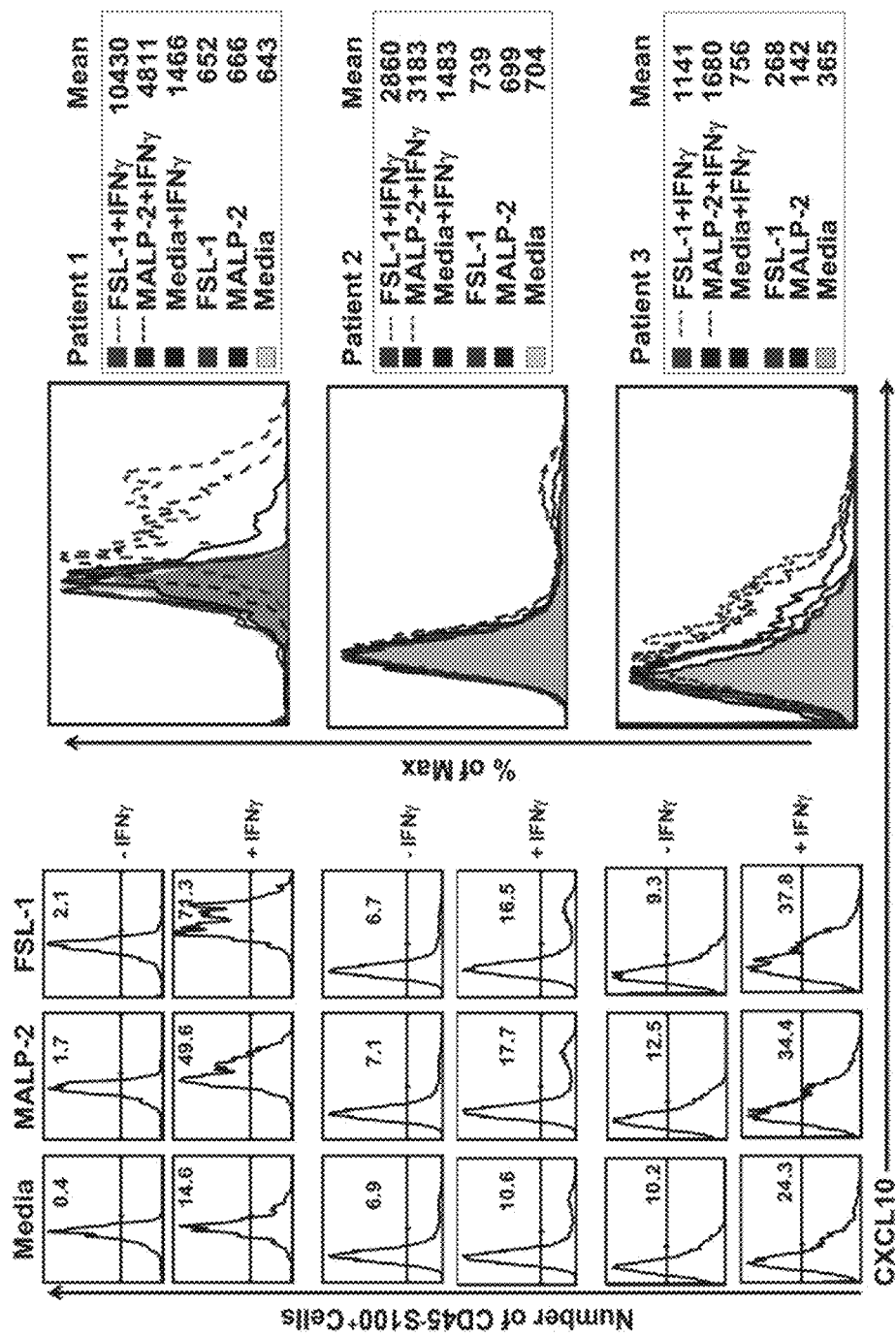
FIGS. 6A-6E. Patient melanomas generate CXCL10 in response to TLR2/6 agonist and IFNγ. Cells from freshly resected human melanoma metastases (Patients 1-3) were analyzed for induced CXCL10 production after stimulation with MALP-2 or FSL-1 +/−IFNγ by flow cytometric analysis. Cell subsets were defined as: melanoma (CD45$^{neg}$S100$^+$), endothelial (S100$^{neg}$CD45$^{neg}$CD105$^+$), B-cell (CD20$^+$), DC (CD11c$^+$HLADR$^+$), macrophage (CD14$^+$), NK-cell (CD56$^+$) and T-cell (CD3$^+$).
Figure 6C:
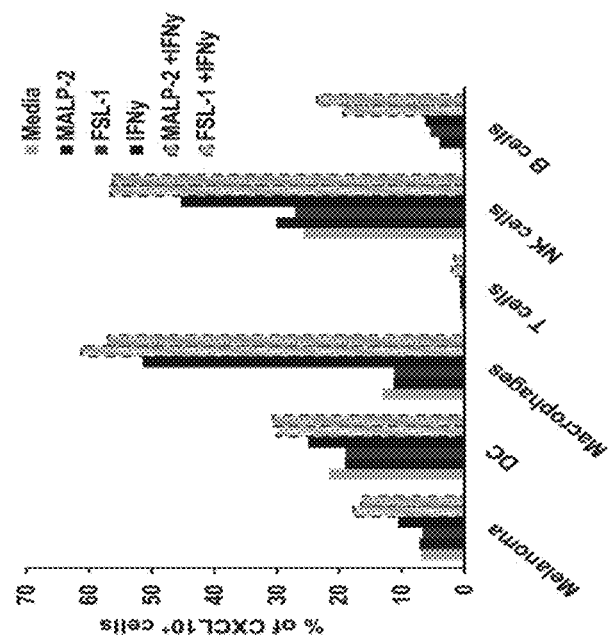
Figure 6B:
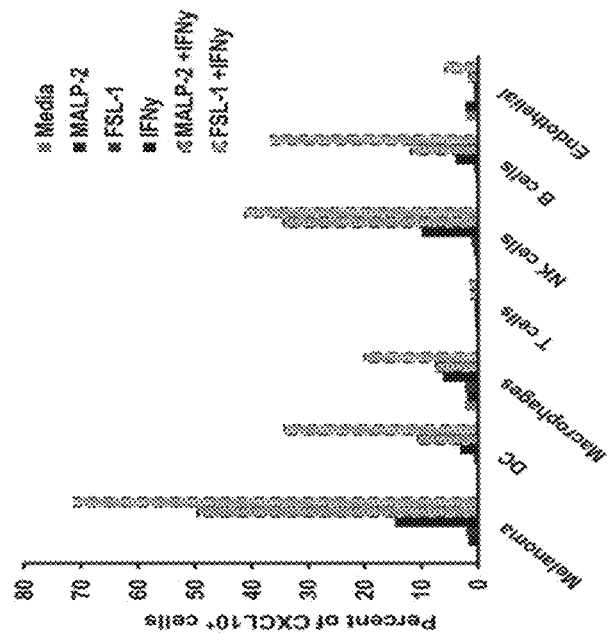
Figure 6E:
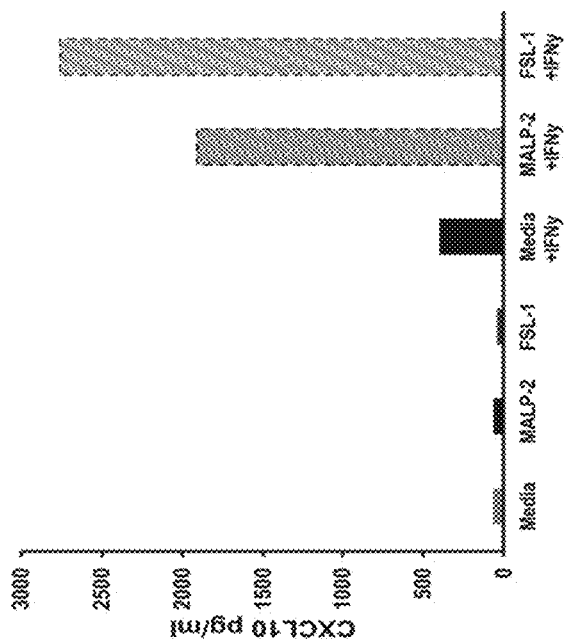
Figure 6D:
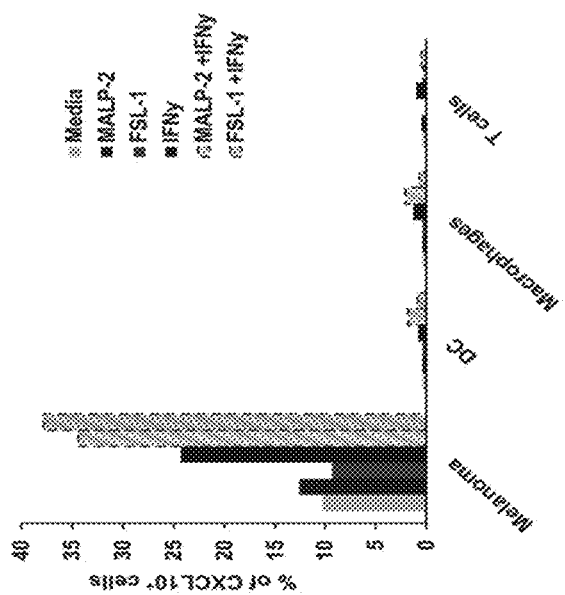

Among cells freshly isolated from tumor tissue, melanoma cells (S100$^+$CD45$^{neg}$) from patients 1-3 produced CXCL10 in response to IFNγ alone, but TLR2/6 agonists alone did not induce CXCL10 above media alone; however, the combination of MALP-2 or FSL-1 and IFNγ markedly enhanced CXCL10 production, in terms of both the percentage of CXCL10$^+$ cells and the MFI of CXCL10 (FIG. 6A). For patients 1-2, CXCL10 was also upregulated among dendritic cells (DC), macrophages, B-cells and natural killer cells (NK) after treatment with TLR2/6 agonists +IFNγ, compared to IFNγ alone or TLR agonist alone (FIGS. 6B-C). However, immune cells from patient 3's tumor did not produce CXCL10 in response to TLR2/6 agonists +IFNγ (FIG. 6D). Interestingly, more than 90% of the melanoma cells from patient 4's tumor produced very high levels of CXCL10 constitutively, a finding that was associated with high numbers of tumor-infiltrating T-cells (data not shown). There was no added effect of the TLR agonists or IFNγ on CXCL10 production in patient 4's cells. CCL3 production was not impacted by TLR2/6 agonists +IFNγ treatment from the melanoma cells in patient tumors; overall CCL3 production was low regardless of treatment, and was much less than what we observed from cultured melanoma cell lines (data not shown).

CXCL10 was also measured from supernatants of stimulated cells from fresh surgically isolated melanoma metastases. Unstimulated cells produced little CXCL10 (~70 pg/ml); IFNγ upregulated CXCL10 production (~400 pg/ml), and cells stimulated with TLR2/6 agonists +IFNγ produced substantially more CXCL10 (~2,000 pg/ml, FIG. 6E).

siRNA Knockdown and Treatment of Additional Cancers

Additional experiments (see FIGS. 12-16) expanded the studies to the use of siRNA knockdown of TLR expression and to other types of cancers. These studies demonstrate the effectiveness of the disclosed combination therapy inducing CXCL10 in cancers other than melanoma.

Figure 12:
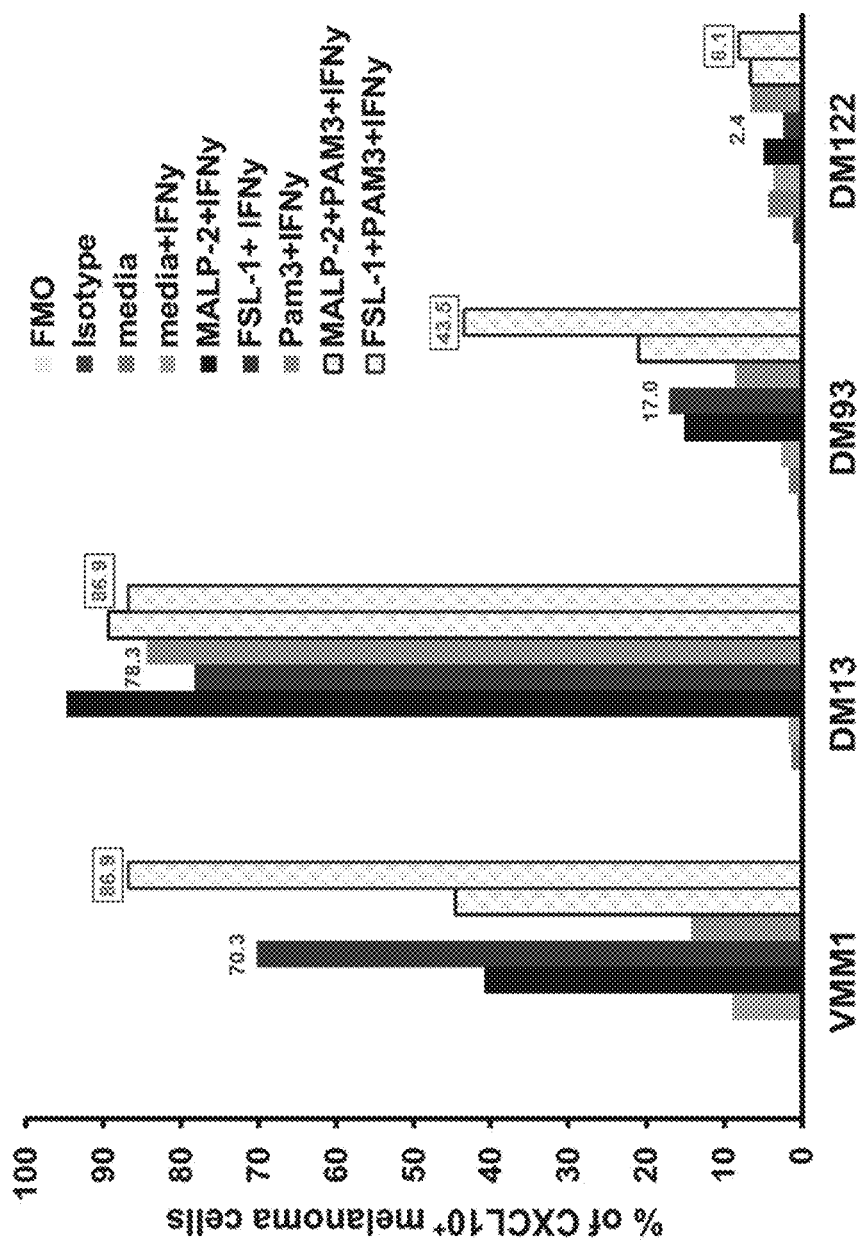
FIG. 12 (bar graph): CXCL10 expression after TLR1/2 agonist (Pam3CSK4) stimulation. Melanoma cells were stimulated with TLR agonists overnight and CXCL10 production from VMM1, DM13, and DM93 cells was assessed by flow cytometry (not shown). Graph demonstrates the percent of CXCL10+cells.

It is shown in FIG. 12 that CXCL10 production is enhanced from melanoma cells stimulated with Pam3CSK4 and IFNγ compared with IFNγ stimulation alone. Additionally, VMM1 and DM93 cells show a further enhancement in CXCL10 production when given a combination of FSL-1 (TLR2/6 agonist), PAM3 (TLR1/2 agonists), and IFNγ. The TLR1/2 agonist tested was Pam3CysSerLys4 (Pam3CSK4) this is a synthetic tripalmitoylated lipopeptide and was used at 5 µg/ml.

Figure 13:
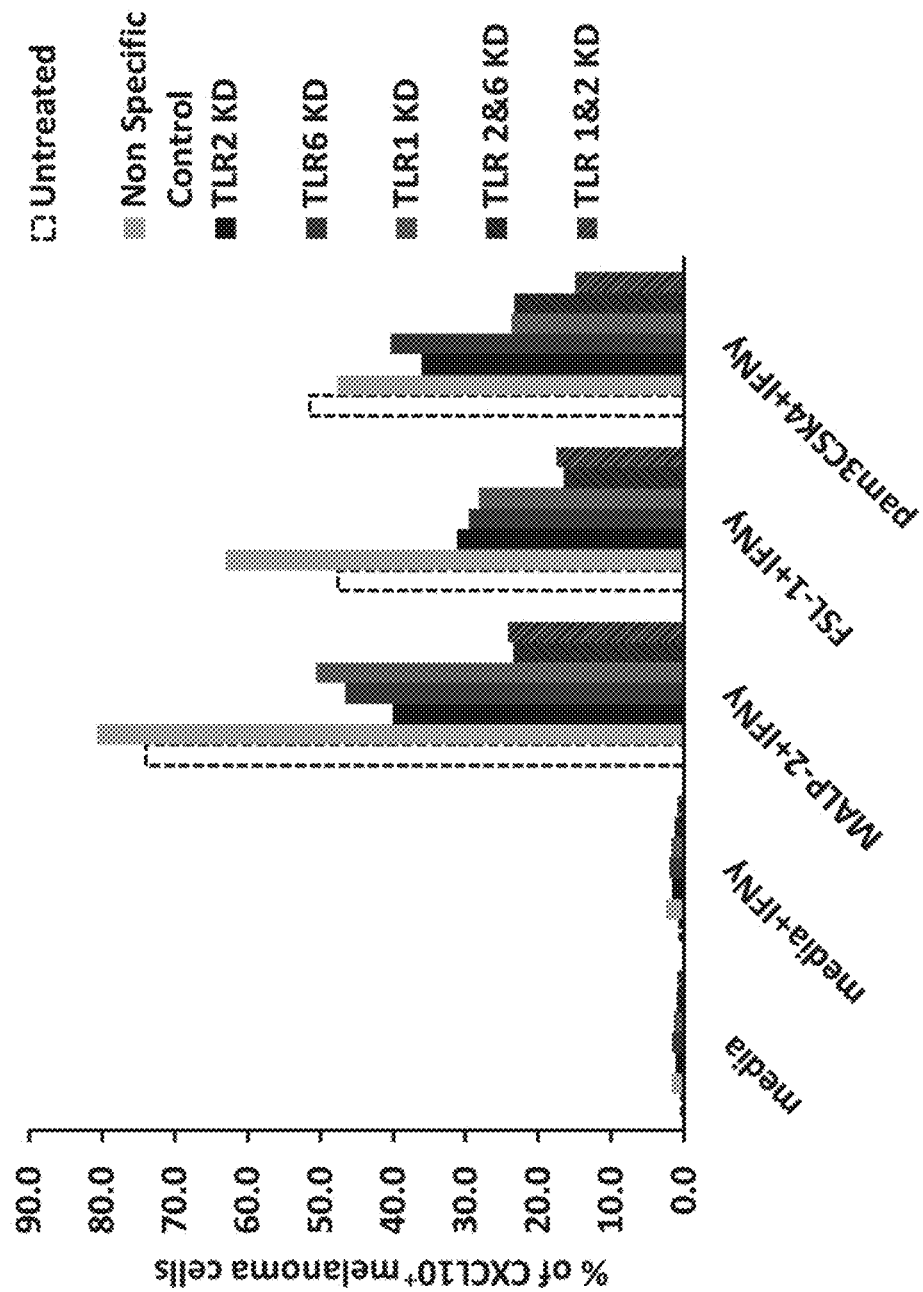
FIG. 13: siRNA to knockdown expression of TLR1, 2, and 6 in DM13 cells; Readout is CXCL10 expression. The TLR1/2 agonist tested was Pam3CysSerLys4 (Pam3CSK4) is a synthetic tripalmitoylated lipopeptide that mimics the acylated amino terminus of bacterial lipoproteins. Graph of the percentage of melanoma cells making CXCL10 after siRNA interference of TLR, 2, or 6 expression and overnight stimulation with the indicated TLR agonists +IFNγ (data are from DM13 cells). These data indicate that TLR2/6 agonists MALP-2 and FSL-1 may also signal through TLR1/2.

FIG. 13 demonstrates that TLR2/6 agonists MALP-2 and FSL-1 may also signal through TLR1/2.

Figure 14:
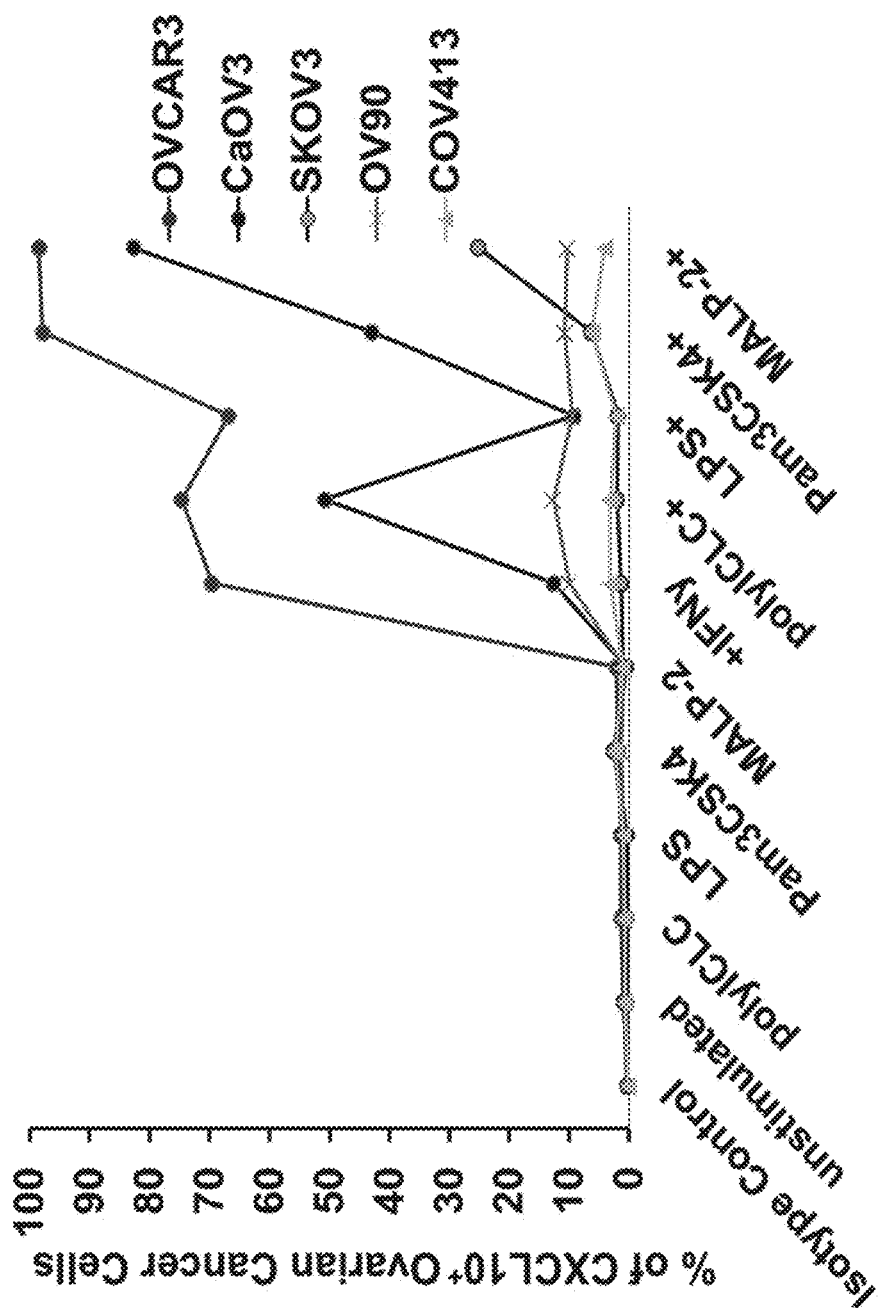
FIG. 14 (line graph): Evidence of TLR2/6 agonists or TLR1/2 agonists working to induce CXCL10 in other cancer cell types besides melanoma-Ovarian Cancer: Ovarian Cancer cell lines: MALP-2+IFNγ increased CXCL10 production in 3/5 cell lines. Ovarian cancer cells were stimulated with TLR agonists overnight alone or in combination with IFNγ (IFNγ stimulation indicated as +). CXCL10 production was assessed by flow cytometry from the indicated ovarian cancer cell lines (n=5). This graph demonstrates the percent of CXCL10+ cells.

FIG. 14 shows that CXCL10 production can be enhanced from some ovarian cancer cell lines (OVCAR, CaOV2 and SKOV3) after simulation with TLR2/6 agonist (MALP-2) or TLR1/2 agonist (Pam3CSK4) and IFNγ compared with IFNγ alone or TLR agonist stimulation alone.

Figure 15:
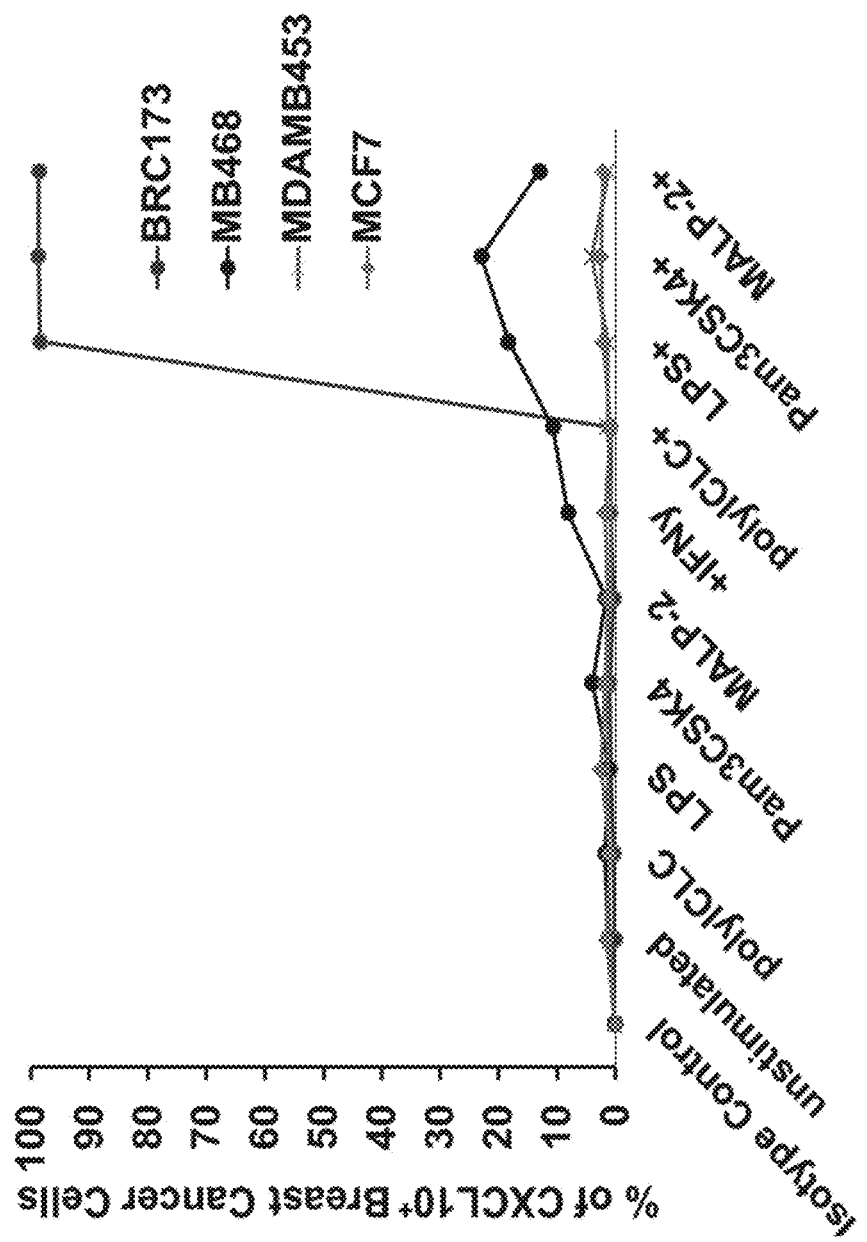
FIG. 15 (line graph): Treatment of Breast Cancer cells. Breast cancer cell lines: LPS, PAM3CSK4, and MALP-2+IFNγ induced CXCL10 production from 2/4 breast cancer cell lines. Breast cancer cells were stimulated with TLR agonists overnight alone or in combination with IFNγ (IFNγ stimulation indicated as +). CXCL10 production was assessed by flow cytometry from the indicated breast cancer cell lines (n=4). This graph demonstrates the percent of CXCL10+ cells.

FIG. 15 shows that that CXCL10 production can be enhanced from some breast cancer cell lines (BRC173, MB468) after simulation with TLR2/6 agonist (MALP-2) or TLR1/2 agonist (Pam3CSK4) and IFNγ compared with IFNγ alone or TLR agonist stimulation alone.

Figure 16:
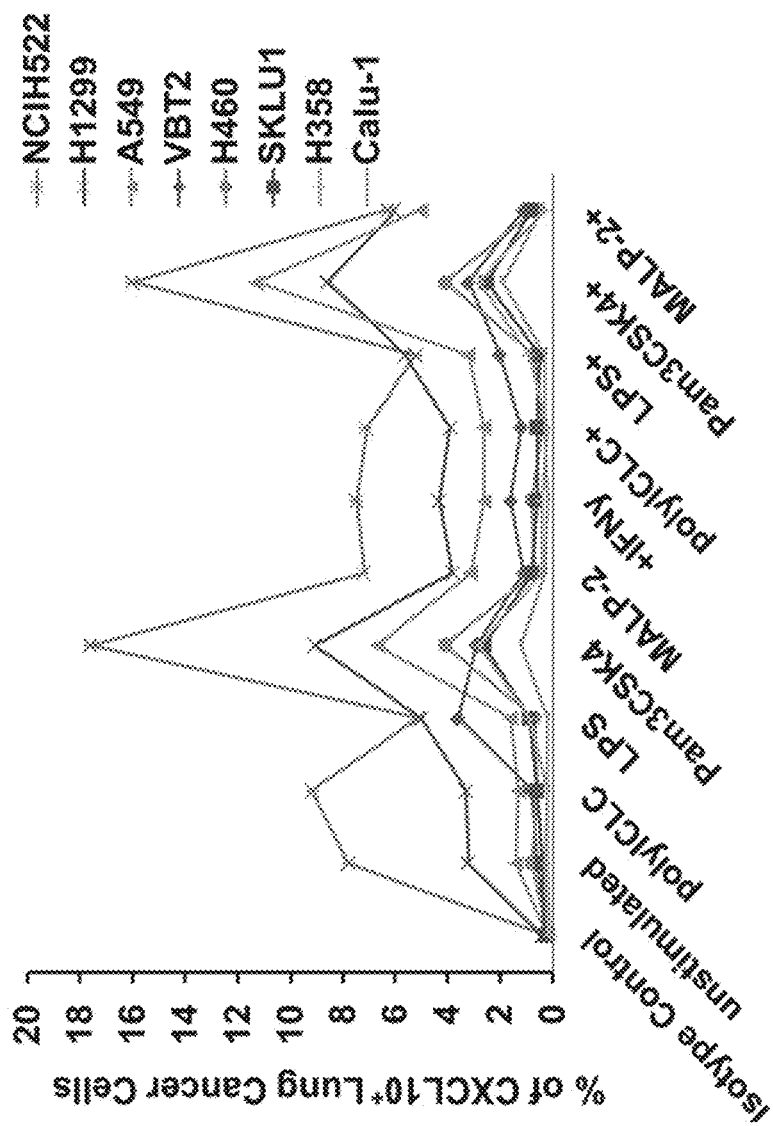
FIG. 16 (line graph): Treatment of Lung Cancer cells with TLR1/2 agonists-TLR1/2 agonists can induce some CXCL10 production from lung cancer cell lines. Lung cancer cells were stimulated with TLR agonists overnight alone or in combination with IFNγ (IFNγ stimulation indicated as +). CXCL10 production was assessed by flow cytometry from the indicated lung cancer cell lines (n=8). This graph demonstrates the percent of CXCL10+ cells.

FIG. 16 shows that that some CXCL10 production can be induced from lung cancer cell lines after simulation with TLR1/2 agonist (Pam3CSK4) alone or in combination with IFNγ.

Figure 17:
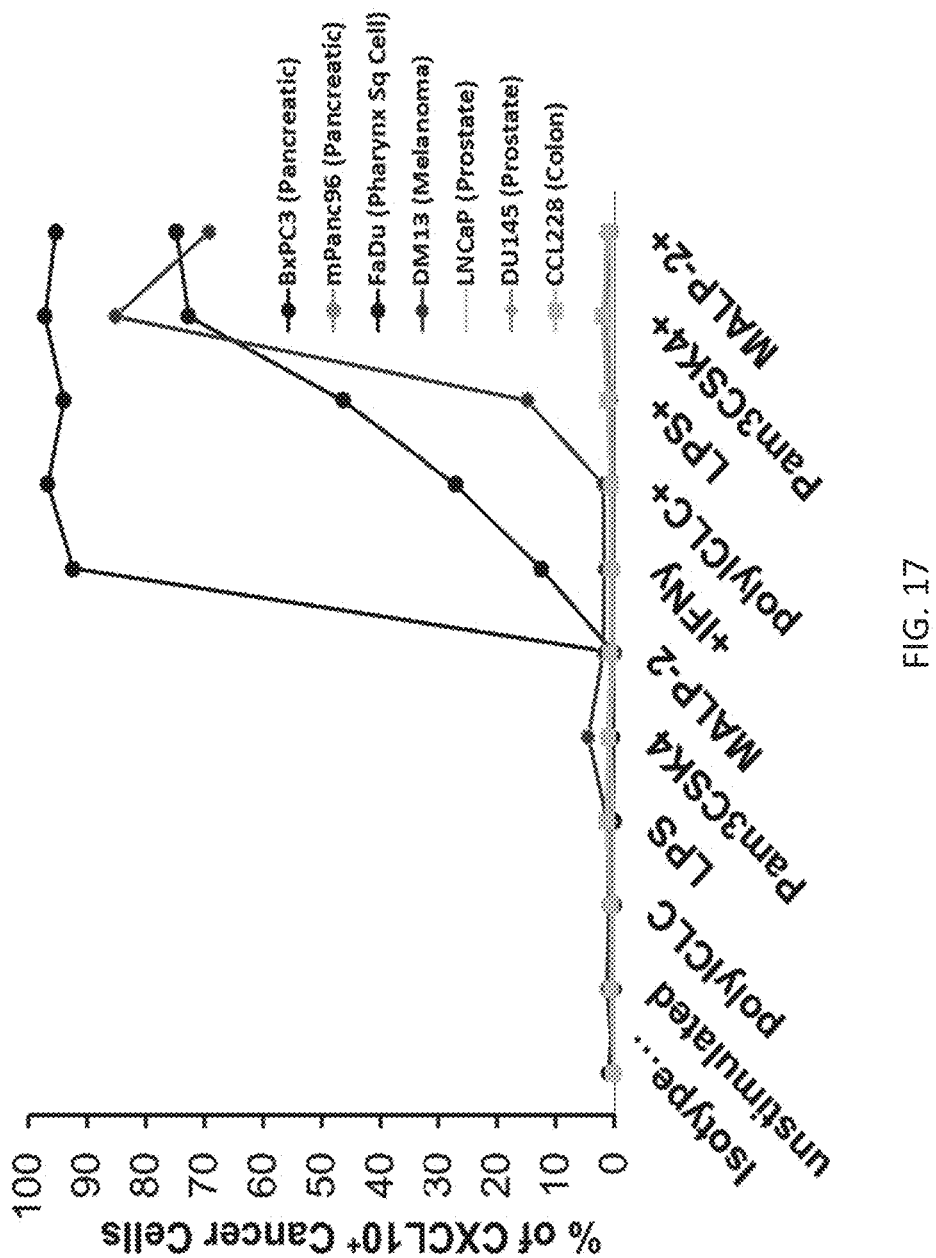
FIG. 17 (line graph): TLR1/2 and TLR2/6 agonists can induce CXCL10 production from a head and neck cancer cell line. Several cancer cell lines including FaDu cancer cells were stimulated individually with TLR agonists overnight alone or in combination with IFNγ (IFNγ stimulation indicated as +). CXCL10 production was assessed by flow cytometry from the indicated lung cancer cell lines. This graph demonstrates the percent of CXCL10+ cells.

FIG. 17 shows that CXCL10 production can be induced from the FaDu cancer cell line after simulation with TLR1/2 agonist (Pam3CSK4) or TLR2/6 agonist (MALP-2) in combination with IFNγ. The FaDu line was established from a hypopharyngeal tumor, a type of squamous cell carcinoma, or head and neck cancer.

Data (not shown) also show that the agonists tested not only increase the percentage of cancer that produce CXCL10, but they also increase the levels of CXCL10 per cell.

Table 1 provides gene array data that demonstrate upregulation of the following genes after treatment with IFNγ alone or MALP-2 or FSL-1 in combination with IFNγ. To assess global effects of TLR2/6 agonists and IFNγ stimulation on melanoma, gene expression profiling of melanoma cell lines was performed. Top upregulated gene lists were made using an Anova cutoff p≤0.005 and Ingenuity Pathway Analysis (IPA), numbers are fold change of gene induction; and the data compare the different treatment conditions for cell lines VMM1, DM13, DM93 & VMM39 in matched comparisons.

TABLE 1

| IFNγ Vs No treatment: | | MALP-2 + IFNγ Vs IFNγ: | | FSL-1 + IFNγ Vs IFNγ: | |
|---|---|---|---|---|---|
| 84.9 | GBP4 | 8.3 | CXCL10 | 21.2 | IL8 |
| 50.6 | GBP1 | 5.7 | CXCL11 | 9.2 | CXCL10 |
| 36.5 | CXCL10 | 5.4 | C3 | 8.9 | CXCL11 |
| 30.2 | IRF1 | 3.4 | TNFAIP3 | 4.7 | C3 |
| 25.7 | TNFSF10 | 3.3 | CCL2 | 4.3 | TNFAIP3 |
| 24.1 | OAS2 | 2.4 | NFKBIA | 3.6 | CCL2 |
| 22.8 | XAF1 | 2.1 | IL32 | 2.3 | IL32 |
| 20.7 | CXCL9 | | | 2.2 | NFKBIA |

TABLE 1-continued

| IFNγ Vs No treatment: | MALP-2 + IFNγ Vs IFNγ: | FSL-1 + IFNγ Vs IFNγ: |
|---|---|---|
| 14.4 | IFI30 | |
| 14.4 | IFITM1 | |

Discussion

Favorable clinical outcomes for melanoma patients, and responses to immune therapy, are closely associated with immune cell infiltration of metastatic lesions (11-14; 33). Gene expression profiling analyses of melanoma metastases containing high numbers of tumor-infiltrating lymphocytes reveal that these tumors express chemokines known to recruit immune cells (CCL2-5, CXCL9-10) (15). However, these studies are limited by their inability to define which cells in melanoma tumors produce the chemokines. Furthermore, most melanomas either have no infiltrating immune cells or contain immune cells limited to perivascular spaces (13). Thus, among aggregates of melanoma cells themselves, immune cells are sparse in most melanoma metastases. To recruit antitumor T-cells to sites where they can mediate tumor clearance, it may be ideal if melanoma cells produced T-cell-attracting chemokines themselves. We have found, that treatment of melanoma cells with TLR2/6 agonists and IFNγ synergistically induces high levels of CXCL10 production directly from melanoma cells, and that the observed effect is much greater than treatment with either agent alone.

Effects of TLR agonists and IFNγ are not expected to be limited to chemokine induction. Other effects that could impact clinical outcomes of cancer patients might include pro-apoptotic or pro-survival signaling downstream of NK-κB, or alterations in expression of tumor antigens or MHC. We found that TLR2/6 agonists +IFNγ did not hinder melanoma cell apoptosis or enhance proliferation (FIGS. 4A-4B). Also, treatment with TLR2/6 agonists +IFNγ did not downregulate expression of MHC Class I or II molecules (FIGS. 10A-10B). Effects on melanocytic antigens were mixed: there was no effect on gp100 expression, but some partial downregulation of Melan-A/MART-1 expression (FIG. 10B). IFNγ has previously been shown to downregulate MART-1/MelanA (34). Overall these effects suggest minor changes in tumor antigen and MHC expression; thus melanoma cells treated with TLR2/6 agonists +IFNγ should remain targets for melanoma-reactive T-cells.

Limited prior data support our finding that melanomas express TLRs-2, -3, -4, -7 and -9 (35-37). However, our study may be the first to report expression of TLR6 by melanoma cells (FIG. 1C & FIGS. 5A-5D). The melanoma cell lines investigated here expressed varied levels of TLR2 and TLR6 (FIGS. 5A-5D). However, our data suggest that low levels of TLR2/6 expression may be sufficient to allow responses to MALP-2 and FSL-1 +IFNγ, since DM13 cells which have relatively low TLR2 expression are responsive to treatment (FIGS. 3A-3B and FIGS. 5A-5D). As our data cannot rule out the possibility that MALP-2 or FSL-1 may be able to signal through additional TLRs, further studies will need to be conducted to determine the specificity of these ligands in melanoma.

The dominance of TLR2/6 agonists +IFNγ in promoting CXCL10 over other TLR agonists was unexpected, as was the striking selectively in the chemokines produced by melanoma cells themselves. Furthermore, we found that even when higher doses of the other TLR agonists were used in combination with IFNγ, TLR2/6 agonists were more potent inducers of CXCL10, with only high concentrations of LPS (≥100 μg) inducing comparable levels of CXCL10. These data suggest that in contrast to immune cells, which produce a wide range of cytokines and chemokines in response to TLR ligation (38; 39), melanoma cells may have altered or mutated signaling pathways which may limit the chemokines they are able to produce, and their responsiveness to TLR stimulation (40). Future studies will need to be performed to determine the mechanism of action of TLR2/6 agonists and IFNγ towards promoting CXCL10 production in melanoma.

In prior studies of melanoma, CXCL10 has reduced tumor cell proliferation, metastasis, and angiogenesis, and has promoted immune cell recruitment and cell-mediated immunity (14; 16). Our data from melanoma cell lines and freshly resected patient metastases reveal that melanoma cells upregulate CXCL10 production upon stimulation with TLR2/6 agonists +IFNγ, when compared to IFNγ alone or TLR agonists alone. However, the levels of CXCL10 upregulation varied among the tested melanoma cell lines and also among the analyzed patient tumors. Furthermore, CXCL10 response to TLR2/6 agonists +IFNγ was evident in melanoma cells, but also was evident in dendritic cells (DC), macrophages, NK cells, and B cells in most tumors (FIGS. 6A-6E). Patient tumors differed in their constitutive CXCL10 expression, in the tumor source (cutaneous vs ocular melanoma), and in the metastatic site (lymph node vs small bowel). The most benefit of TLR2/6 agonists +IFNγ towards CXCL10 enhancement may come from tumors with no basal CXCL10 production, similar to patient 1, or low basal CXCL10 production such as patients 2 and 3 (FIGS. 6A-6E). Interestingly, all three small bowel metastases, from patient's 2-4, had basal CXCL10 production; thus, the location of the metastasis may have an effect on CXCL10 production from the tumor.

Previous studies have shown that IFNγ or IL-12 treatment, through induction of IFNγ from immune cells, can induce CXCL10 production from tumors. We have found that TLR2/6 agonists can dramatically augment that response. CXCL10 promotes migration of CD4$^+$ and CD8$^+$ T-cells (18; 41; 42) these findings therefore suggest that there may be therapeutic value for enhancing T-cell migration. While FSL-1 has not been tested in clinical trials, MALP-2 has been tested for the treatment of pancreatic cancer in phase I/II clinical trials and was administered intratumorally safely up to 20 μg; MALP-2 was also tested in a phase I trial for wound healing (43; 44). IFNγ has been tested as a treatment for melanoma and was administered intratumorally at a dose of 2 million IU of IFNγ (NCT00977145). Extrapolating from our dose response assays, we anticipate that for a 5 cm diameter metastasis, doses of MALP-2, FSL-1, and IFNγ expected to cause CXCL10 production would need to be 6.5 μg, 325 μg, and 65,000 IU, respectively. Since MALP-2 and IFNγ have been administered in clinical trials at doses higher to these, it is possible that these agents may be safely administered at doses expected to induce CXCL10 in the tumor microenvironment (FIG. 4D). Many immune therapies appear to be more effective in tumors that contain CD8$^+$ T-cell infiltrates and have immune signatures, thus it is reasonable to explore the possibility of intratumoral administration of a TLR2/6 agonist and IFNγ, in combination with other immune therapies such as vaccination, adoptive cell transfer, or blockade of CTLA-4 or PD-1 (10-12; 14; 45). Newer approaches to target selective delivery of such agents to tumor after systemic administration may also enable application for patients with disseminated melanoma.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY (1) Alexandrescu D T, Ichim T E, Riordan N H, Marincola F M, Di N A, Kabigting F D, Dasanu C A. Immunotherapy for melanoma: current status and perspectives. J Immunother 2010 July; 33(6):570-90.
(2) Shapira-Frommer R, Schachter J. Adoptive immunotherapy of advanced melanoma. Curr Treat Options Oncol 2012 September; 13(3):340-53.
(3) Lee S, Margolin K. Tumor-infiltrating lymphocytes in melanoma. Curr Oncol Rep 2012 October; 14(5):468-74.
(4) Korman A J, Peggs K S, Allison J P. Checkpoint blockade in cancer immunotherapy. Adv Immunol 2006; 90:297-339.
(5) Menaa F. Latest approved therapies for metastatic melanoma: what comes next? J Skin Cancer 2013; 2013: 735282.
(6) Hamid O, Robert C, Daud A, Hodi F S, Hwu W J. Kefford R, Wolchok J D, Hersey P, Joseph R W, Weber J S, Dronca R, Gangadhar T C, et al. Safety and Tumor Responses with Lambrolizumab (Anti-PD-1) in Melanoma. N Engl J Med 2013 Jun. 2.
(7) Wolchok J D, Kluger H, Callahan M K, Postow M A, Rizvi N A, Lesokhin A M, Segal N H, Ariyan C E, Gordon R A, Reed K, Burke M M, Caldwell A, et al. Nivolumab plus Ipilimumab in Advanced Melanoma. N Engl J Med 2013 Jun. 2.
(8) Powderly J D, Koeppen H, Hodi F S, Sosman J A, Gettinger S N, Desai R, Tabernero J, Soria J-C, Hamid O, Fine G D, Xiao Y, Mokatrin A, et al. Biomarkers and associations with the clinical activity of PD-L1 blockade in a MPDL3280A study., 31 ed 2013. p. Abstract #3001.
(9) Weiss G R, Grosh W W, Chianese-Bullock K A, Zhao Y, Liu H, Slingluff C L, Jr., Marincola F M, Wang E. Molecular insights on the peripheral and intratumoral effects of systemic high-dose rIL-2 (aldesleukin) administration for the treatment of metastatic melanoma. Clin Cancer Res 2011 Dec. 1; 17(23):7440-50.
(10) Gough M, Crittenden M, Thanarajasingam U, Sanchez-Perez L, Thompson J, Jevremovic D, Vile R. Gene therapy to manipulate effector T cell trafficking to tumors for immunotherapy. J Immunol 2005 May 1; 174(9): 5766-73.
(11) Dengel L T, Norrod A G, Gregory B L, Clancy-Thompson E, Burdick M D, Strieter R M, Slingluff C L, Jr., Mullins D W. Interferons induce CXCR3-cognate chemokine production by human metastatic melanoma. J Immunother 2010 November; 33(9):965-74.
(12) Wu R, Forget M A, Chacon J, Bernatchez C, Haymaker C, Chen J Q, Hwu P, Radvanyi L G. Adoptive T-cell therapy using autologous tumor-infiltrating lymphocytes for metastatic melanoma: current status and future outlook. Cancer J 2012 March; 18(2):160-75.
(13) Erdag G, Schaefer J T, Smolkin M E, Deacon D H, Shea S M, Dengel L T, Patterson J W, Slingluff C L, Jr. Immunotype and immunohistologic characteristics of tumor-infiltrating immune cells are associated with clinical outcome in metastatic melanoma. Cancer Res 2012 Mar. 1;72(5): 1070-80.
(14) Hong M, Puaux A L, Huang C, Loumagne L, Tow C, Mackay C, Kato M, Prevost-Blondel A, Avril M F, Nardin A, Abastado J P. Chemotherapy induces intratumoral expression of chemokines in cutaneous melanoma, favoring T-cell infiltration and tumor control. Cancer Res 2011 Nov. 15; 71(22):6997-7009.
(15) Harlin H, Meng Y, Peterson A C, Zha Y, Tretiakova M, Slingluff C, McKee M, Gajewski T F. Chemokine expression in melanoma metastases associated with CD8+ T-cell recruitment. Cancer Res 2009 Apr. 1; 69(7):3077-85.
(16) Tanese K, Grimm E A, Ekmekcioglu S. The role of melanoma tumor-derived nitric oxide in the tumor inflammatory microenvironment: its impact on the chemokine expression profile, including suppression of CXCL10. Int J Cancer 2012 Aug. 15; 131(4):891-901.
(17) Peng W, Liu C, Xu C, Lou Y, Chen J, Yang Y, Yagita H, Overwijk W W, Lizee G, Radvanyi L, Hwu P. PD-1 blockade enhances T-cell migration to tumors by elevating IFN-gamma inducible chemokines. Cancer Res 2012 Oct. 15; 72(20):5209-18.
(18) Dufour J H, Dziejman M, Liu M T, Leung J H, Lane T E, Luster A D. IFN-gamma-inducible protein 10 (IP-10; CXCL10)-deficient mice reveal a role for IP-10 in effector T cell generation and trafficking. J Immunol 2002 Apr. 1; 168(7):3195-204.
(19) Tannenbaum C S, Tubbs R, Armstrong D, Finke J H, Bukowski R M, Hamilton T A. The CXC chemokines IP-10 and Mig are necessary for IL-12-mediated regression of the mouse RENCA tumor. J Immunol 1998 Jul. 15; 161(2):927-32.
(20) Kang J Y, Lee J O. Structural biology of the Toll-like receptor family. Annu Rev Biochem 2011 Jun. 7; 80:917-41.
(21) Schill T, Schon M P, Pletz N, Emmert S, Schon M. Stimulation of pulmonary immune responses by the TLR2/6 agonist MALP-2 and effect on melanoma metastasis to the lung. Exp Dermatol 2012 February; 21(2):91-8.
(22) Oldford S A, Haidl I D, Howatt M A, Leiva C A, Johnston B, Marshall J S. A critical role for mast cells and mast cell-derived IL-6 in TLR2-mediated inhibition of tumor growth. J Immunol 2010 Dec. 1; 185(11):7067-76.
(23) Li X, Jiang S, Tapping R I. Toll-like receptor signaling in cell proliferation and survival. Cytokine 2010 January; 49(1):1-9.
(24) Lopez J, Meier P. To fight or die—inhibitor of apoptosis proteins at the crossroad of innate immunity and death. Curr Opin Cell Biol 2010 December; 22(6):872-81.
(25) Hasan U A, Caux C, Perrot I, Doffin A C, Menetrier-Caux C, Trinchieri G, Tommasino M, Vlach J. Cell proliferation and survival induced by Toll-like receptors is antagonized by type I IFNs. Proc Natl Acad Sci USA 2007 May 8; 104(19):8047-52.
(26) Bohnhorst J, Rasmussen T, Moen S H, Flottum M, Knudsen L, Borset M, Espevik T, Sundan A. Toll-like receptors mediate proliferation and survival of multiple myeloma cells. Leukemia 2006 June; 20(6): 1138-44.
(27) Giroux M, Schmidt M, Descoteaux A. IFN-gamma-induced MHC class II expression: transactivation of class

(28) Zhou F. Molecular mechanisms of IFN-gamma to up-regulate MHC class I antigen processing and presentation. Int Rev Immunol 2009; 28(3-4):239-60.

(29) Kang H Y, Park T J, Jin S H. Imiquimod, a Toll-like receptor 7 agonist, inhibits melanogenesis and proliferation of human melanocytes. J Invest Dermatol 2009 January; 129(1):243-6.

(30) Schroder K, Sweet M J, Hume D A. Signal integration between IFNgamma and TLR signalling pathways in macrophages. Immunobiology 2006; 211(6-8):511-24.

(31) Nakao Y, Funami K, Kikkawa S, Taniguchi M, Nishiguchi M, Fukumori Y, Seya T, Matsumoto M. Surface-expressed TLR6 participates in the recognition of diacylated lipopeptide and peptidoglycan in human cells. J Immunol 2005 Feb. 1; 174(3):1566-73.

(32) Ochoa M T, Legaspi A J, Hatziris Z, Godowski P J, Modlin R L, Sieling P A. Distribution of Toll-like receptor 1 and Toll-like receptor 2 in human lymphoid tissue. Immunology 2003 January; 108(1):10-5.

(33) Crittenden M, Gough M, Chester J, Kottke T, Thompson J, Ruchatz A, Clackson T, Cosset F L, Chong H, Diaz R M, Harrington K, Alvarez V L, et al. Pharmacologically regulated production of targeted retrovirus from T cells for systemic antitumor gene therapy. Cancer Res 2003 Jun. 15; 63(12):3173-80.

(34 Le Poole I C, Riker A I, Quevedo M E, Stennett L S, Wang E, Marincola F M, Kast W M, Robinson J K, Nickoloff B J. Interferon-gamma reduces melanosomal antigen expression and recognition of melanoma cells by cytotoxic T cells. Am J Pathol 2002 February; 160(2): 521-8.

(35) Goto Y, Arigami T, Kitago M, Nguyen S L, Narita N, Ferrone S, Morton D L, Irie R F, Hoon D S. Activation of Toll-like receptors 2, 3, and 4 on human melanoma cells induces inflammatory factors. Mol Cancer Ther 2008 November; 7(11):3642-53.

(36) Saint-Jean M, Knol A C, Nguyen J M, Khammari A, Dreno B. TLR expression in human melanoma cells. Eur J Dermatol 2011 November; 21(6):899-905.

(37) Yu N, Zhang S, Zuo F, Kang K, Guan M, Xiang L. Cultured human melanocytes express functional toll-like receptors 2-4, 7 and 9. J Dermatol Sci 2009 November; 56(2): 113-20.

(38) Makela S M, Strengell M, Pietila T E, Osterlund P, Julkunen I. Multiple signaling pathways contribute to synergistic TLR ligand-dependent cytokine gene expression in human monocyte-derived macrophages and dendritic cells. J Leukoc Biol 2009 April; 85(4):664-72.

(39) Barksby H E, Nile C J, Jaedicke K M, Taylor J J, Preshaw P M. Differential expression of immunoregulatory genes in monocytes in response to *Porphyromonas gingivalis* and *Escherichia coli* lipopolysaccharide. Clin Exp Immunol 2009 June; 156(3):479-87.

(40) Iwasaki A, Medzhitov R. Toll-like receptor control of the adaptive immune responses. Nat Immunol 2004 October; 5(10):987-95.

(41) Roth S J, Carr M W, Springer T A. C—C chemokines, but not the C—X—C chemokines interleukin-8 and interferon-gamma inducible protein-10, stimulate transendothelial chemotaxis of T lymphocytes. Eur J Immunol 1995 December; 25(12):3482-8.

(42) Franciszkiewicz K, Boissonnas A, Boutet M, Combadiere C, Mami-Chouaib F. Role of chemokines and chemokine receptors in shaping the effector phase of the antitumor immune response. Cancer Res 2012 Dec. 15; 72(24):6325-32.

(43) Schmidt J, Welsch T, Jager D, Muhlradt P F, Buchler M W, Marten A. Intratumoural injection of the toll-like receptor-2/6 agonist 'macrophage-activating lipopeptide-2' in patients with pancreatic carcinoma: a phase I/II trial. Br J Cancer 2007 Sep. 3; 97(5):598-604.

(44) Niebuhr M, Muhlradt P F, Wittmann M, Kapp A, Werfel T. Intracutaneous injection of the macrophage-activating lipopeptide-2 (MALP-2) which accelerates wound healing in mice—a phase 1 trial in 12 patients. Exp Dermatol 2008 December; 17(12): 1052-6.

(45) Topalian S L, Hodi F S, Brahmer J R, Gettinger S N, Smith D C, McDermott D F, Powderly J D, Carvajal R D, Sosman J A, Atkins M B, Leming P D, Spigel D R, et al. Safety, activity, and immune correlates of anti-PD-1 antibody in cancer. N Engl J Med 2012 Jun. 28; 366(26): 2443-54.

What is claimed is:

1. A method of inducing CXCL10 in a cancer cell and treating a subject in need thereof for cancer, wherein said method induces CXCL10 in cancer cells from said cancer, wherein said cancer is selected from the group consisting of melanoma, ovarian cancer, breast cancer, and head and neck cancer, said method comprising administering to a subject in need thereof a pharmaceutical composition consisting of an effective amount of interferon-gamma (IFNγ) and an effective amount of at least one agonist of a Toll-Like Receptor (TLR), and optionally an inducer of IFNγ, wherein said TLR is selected from the group consisting of TLR1, 2, 4, and 6, and wherein said at least one agonist is selected from the group consisting of a TLR1/2, a TLR2/6, and a TLR4 agonist, wherein said administering induces CXCL10 in a cancer cell at a synergistic level compared to a level induced when administering just said IFNγ or a level induced when administering just said at least one agonist of TLR, thereby treating a cancer selected from the group consisting of melanoma, ovarian cancer, breast cancer, and head and neck cancer.

2. The method of claim 1, wherein said at least one agonist is selected from the group consisting of macrophage-activating lipopeptide 2 (MALP-2), fibroblast-stimulating lipopeptide-1 (FSL-1), lipopolysaccharide (LPS), and Pam3CysSerLys4 (Pam3).

3. The method of claim 2, wherein said at least one agonist is MALP-2 or FSL-1.

4. The method of claim 3, wherein said at least one agonist is FSL-1.

5. The method of claim 2, wherein said MALP-2 is administered at a dose of about 0.1 μg to about 1,000 μg.

6. The method of claim 5, wherein said MALP-2 is administered intratumorally at a dose of about 6.5 μg.

7. The method of claim 2, wherein said agonist is FSL-1 and said FSL-1 is administered intratumorally at a dose of about 0.1 μg to about 1,000 μg.

8. The method of claim 7, wherein said FSL-1 is administered intratumorally at a dose of about 325 μg.

9. The method of claim 2, wherein said IFNγ is administered at a dose of about 5,000 international units (IU) to about 1,000,000 IU.

10. The method of claim 9, wherein said IFNγ is administered intratumorally at a dose of about 65,000 IU.

11. The method of claim 2, wherein said cancer is melanoma, said agonist is FSL-1 and said inducer of IFNγ is a STING agonist.

12. The method of claim 1, wherein said inducer of IFNγ is a stimulator of interferon genes (STING) agonist.

13. The method of claim 1, wherein said agonist is coupled to a molecule or delivery vehicle to aid in localization at a site of administration.

14. The method of claim 1, wherein said at least one agonist is coupled to IFNγ.

15. The method of claim 14, wherein said at least one agonist coupled to IFNγ is further coupled to a lipid.

16. The method of claim 1, wherein said composition is administered by a route selected from the group consisting of intratumoral, parenteral, intravenous, topical, and direct.

17. The method of claim 1, wherein said cancer is melanoma.

18. The method of claim 1, wherein an inducer of IFNγ is not administered.

19. The method of claim 18, wherein said at least one agonist is FSL-1.

20. The method of claim 1, wherein said method induces infiltration of T cells into said cancer.

21. The method of claim 1, wherein said cancer has no infiltrating T cells.

22. The method of claim 1, wherein the cancer is melanoma and wherein the at least one agonist is MALP-2 or FSL-1.

23. The method of claim 22, wherein an inducer of IFNγ is not administered.

* * * * *